United States Patent
Fuchs et al.

(10) Patent No.: US 12,148,073 B2
(45) Date of Patent: Nov. 19, 2024

(54) DEEP ENCODER-DECODER MODELS FOR RECONSTRUCTING BIOMEDICAL IMAGES

(71) Applicant: MEMORIAL SLOAN KETTERING CANCER CENTER, New York, NY (US)

(72) Inventors: Thomas C. Fuchs, New York, NY (US); Ida Häggström, New York, NY (US); Charles Ross Schmidtlein, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 315 days.

(21) Appl. No.: 17/040,416

(22) PCT Filed: Mar. 22, 2019

(86) PCT No.: PCT/US2019/023733
§ 371 (c)(1),
(2) Date: Sep. 22, 2020

(87) PCT Pub. No.: WO2019/183584
PCT Pub. Date: Sep. 26, 2019

(65) Prior Publication Data
US 2021/0074036 A1     Mar. 11, 2021

Related U.S. Application Data

(60) Provisional application No. 62/647,190, filed on Mar. 23, 2018, provisional application No. 62/734,038, filed on Sep. 20, 2018.

(51) Int. Cl.
*G06T 11/00* (2006.01)
*A61B 6/03* (2006.01)
(Continued)

(52) U.S. Cl.
CPC ............ *G06T 11/006* (2013.01); *A61B 6/032* (2013.01); *A61B 6/037* (2013.01); *G06T 7/0012* (2013.01);
(Continued)

(58) Field of Classification Search
CPC ............ G06T 2207/10104; G06T 2207/20084
See application file for complete search history.

(56) References Cited

U.S. PATENT DOCUMENTS 8,917,925 B1    12/2014  Grady et al.
10,475,214 B2 *  11/2019  Fu ........................ G06V 30/194
(Continued)

FOREIGN PATENT DOCUMENTS

WO     WO-2017223560 A1 *  12/2017 ............... A61B 5/00

OTHER PUBLICATIONS

Bi, L., Kim, J., Kumar, A., Feng, D., Fulham, M. (2017). Synthesis of Positron Emission Tomography (PET) Images via Multi-channel Generative Adversarial Networks (GANs). In: , et al. Molecular Imaging, Reconstruction and Analysis of Moving Body Organs . . . RAMBO CMMI Switch 2017 2017 2017. (Year: 2017).*
(Continued)

*Primary Examiner* — Gandhi Thirugnanam
(74) *Attorney, Agent, or Firm* — Foley & Lardner LLP

(57) ABSTRACT

The present disclosure is directed to systems and methods for reconstructing biomedical images. A projection preparer may identify a projection dataset derived from a tomographic biomedical imaging scan. An encoder-decoder model may reconstruct reconstructing tomographic biomedical images from projection data. The encoder-decoder model may include an encoder. The encoder may include a first series of transform layers to generate first feature maps using the projection dataset. The encoder-decoder may include a decoder. The decoder may include a second series (Continued)

of transform layers to generate second features maps using the first feature maps from the encoder. The system may include a reconstruction engine executable on the one or more processors. The reconstruction engine may apply the encoder-decoder model to the projection dataset to generate a reconstructed tomographic biomedical image based on the second feature maps generated by the decoder of the encoder-decoder model.

20 Claims, 32 Drawing Sheets

(51) Int. Cl.
    *G06T 7/00*       (2017.01)
    *G06T 9/00*       (2006.01)
(52) U.S. Cl.
    CPC .... *G06T 9/002* (2013.01); *G06T 2207/10104* (2013.01); *G06T 2207/20081* (2013.01); *G06T 2207/20084* (2013.01); *G06T 2207/30004* (2013.01)

(56) References Cited

U.S. PATENT DOCUMENTS

| | | | | |
|---|---|---|---|---|
| 2016/0093048 | A1* | 3/2016 | Cheng | G06V 30/194 382/131 |
| 2019/0028637 | A1* | 1/2019 | Kolesov | G06T 17/00 |
| 2019/0035117 | A1* | 1/2019 | Xing | G06T 11/006 |
| 2019/0266728 | A1* | 8/2019 | Lee | A61B 6/037 |
| 2019/0340793 | A1* | 11/2019 | Jin | G06K 9/6256 |
| 2020/0342637 | A1* | 10/2020 | Zhang | G06T 5/70 |
| 2020/0380673 | A1* | 12/2020 | Wang | G06T 7/0012 |
| 2021/0012541 | A1* | 1/2021 | Lee | G01N 23/046 |
| 2021/0019924 | A1* | 1/2021 | Moriyasu | A61B 6/0407 |
| 2021/0074036 | A1* | 3/2021 | Fuchs | G06N 3/0454 |

OTHER PUBLICATIONS

Häggström I, Schmidtlein CR, Campanella G, Fuchs TJ. DeepPET: A deep encoder decoder network for directly solving the PET image reconstruction inverse problem. Med Image Anal. May 2019;54:253-262. doi: 10.1016/j.media.2019.03.013. Epub Mar. 30, 2019. (Year: 2019).*

Author Unknown, "Selecting examples for training", 2016, https://www.websense.com/content/support/library/data/v82/machine_learning/ml_select_examples.aspx (Year: 2016).*

Author Unknown, "AlphaDropout layer", 2017, https://keras.io/api/layers/regularization_layers/alpha_dropout/ (Year: 2017).*

Amar Budhiraja, "Dropout in (Deep) Machine learning", 2016, https://medium.com/@amarbudhiraja/https-medium-com-amarbudhiraja-learning-less-to-learn-better-dropout-in-deep-machine-learning-74334da4bfc5 (Year: 2016).*

Author Unknown, "Is the Keras implementation of dropout correct?", 2016, https://stackoverflow.com/questions/38592943/is-the-keras-implementation-of-dropout-correct (Year: 2016).*

Chris Albon, "Adding Dropout", 2017, https://chrisalbon.com/code/deep_learning/keras/adding_dropout/ (Year: 2017).*

Chen et al. "Low-Dose CT with a Residual Encoder-Decoder Convolutional Neural Network (RED-CNN)." In: Cornell University Library/Physics/Medical Physics, [online] [retrieved on May 29, 2019 (May 29, 2019)] Retrieved from the Internet <URL: https://arxiv.org/abs/1702.00288>, entire document, especially Abstract.

Cui et al. "Deep reconstruction model for dynamic PET images." In: IEEE Trans Med Imaging. Dec. 2017, [online] [retrieved on May 29, 2019 (May 29, 2019)1 Retrieved from the Internet <URL: https://www.ncbi.nlm.nih.gov/pmc/articles/PMC5608245/>, entire document, especially Abstract.

International Search Report and Written Opinion on PCT PCT/US2019/023733 DTD Jul. 5, 2019.

Mao et al. "Image Restoration Using Very Deep Convolutional Encoder-Decoder Networks with 1-20 Symmetric Skip Connections." In: Cornell University Library/Computer Science/ Computer Vision and Pattern Recognition., [online] [retrieved on May 29, 2019 (May 29, 2019)] Retrieved from the Internet <URL: https://arxiv.org/abs/1603.09056v2>, entire document, especially Abstract; p. 2-6.

Jieqing Jiao et al: "Fast PET reconstruction using Multi-scale Fully Convolutional Neural Network", Arxiv.Org, Cornell University Library, 201 Olin Library Cornell University Ithaca, NY 14853, Apr. 24, 2017 (Apr. 24, 2017), XP080765058, p. 2-p. 4.

Kyong Hwan Jin et al: "Deep Convolutional Neural Network for Inverse Problems in Imaging", Arxiv.Org, Cornell University Library, 201 Olin Library Cornell University Ithaca, NY 14853, Nov. 11, 2016 (Nov. 11, 2016), XP081396772, DOI: 10.1109/TIP.2017.2713099 p. 7-p. 8.

* cited by examiner

DEEP ENCODER-DECODER MODELS FOR RECONSTRUCTING BIOMEDICAL IMAGES

CROSS REFERENCES TO RELATED PATENT APPLICATIONS

The present application is a U.S. National Stage Application of PCT/US2019/023733, filed on Mar. 22, 2019, which claims the benefit of priority to U.S. Provisional Patent Application No. 62/647,190, titled "DEEPREC: A DEEP ENCODER-DECODER NETWORK FOR DIRECTLY SOLVING THE PET RECONSTRUCTION INVERSE PROBLEM," filed Mar. 23, 2018, and to U.S. Provisional Patent Application No. 62/734,038, titled "DEEP ENCODER-DECODER NETWORKS FOR RECONSTRUCTING BIOMEDICAL IMAGES," filed Sep. 20, 2018, the contents of each of which are incorporated by reference herein in their entireties.

TECHNICAL FIELD

The present application relates generally to reconstructing biomedical images.

BACKGROUND

Various biomedical imaging techniques may be used to reveal an internal anatomical and physiological structure of a body hidden by an outer layer. Reconstruction of such images may consume a significant amount of computing resources and time, taking as long as several hours to reconstruct from a single scan.

SUMMARY

The internal anatomical and physiological structure of a body may be acquired using biomedical imaging techniques of various modalities, such as radiography (e.g., X-rays and fluoroscopy), magnetic resonance imaging (MRI), ultrasonography, tactile imaging (elastography), photoacoustic imaging, functional near-infrared spectroscopy, and nuclear medicine functional imaging (e.g., positron emission tomography and single-photo emission computed tomography (SPECT)), among others. Using the internal structure ascertained from biomedical imaging, medical diagnosis and treatment management may be performed. In general, the different modalities of biomedical imaging may include scanning and then reconstructing the image from the scan. The scanning of a subject may take several minutes, sometimes hours. Moreover, the reconstruction process itself may also consume several hours for a single scan. In addition, the whole process may be excessively burdensome for the subject and the medical practitioners administering the scan.

To reduce the amount of time in reconstruction, the present systems and methods are directed to training an encoder-decoder model and using the model for reconstruction of biomedical images. The encoder-decoder model may include an encoder and a decoder. The encoder-decoder model may take a projection dataset from a biomedical imaging scan or training data at an input. The projection dataset may be of a predefined size, and may be defined in three-dimensional. Prior to feeding the projection dataset into the model, the projection dataset may be sliced into two-dimensional subsets. Interpolation procedures (e.g., Fourier rebinning) can be used to extract two-dimensional slices from the projection dataset. By taking two-dimensional slices of the projection data, the amount of data inputted into the encoder-decoder model may be reduced, allowing the application of the model to be computationally tractable.

With the project dataset as the input, the encoder may generate a set of feature maps. The encoder may include a series of transform layers. For example, the transform layers of the encoder layer may be a set of convolutional neural networks (CNNs). Each CNN may include a convolutional layer, a batch normalization layer, and a rectifier linear layer. The convolutional layer may include a predefined number of filters. Each filter may be of a predefined size (e.g., 3×3). The number of filters across the convolutional layers may increase at each successive CNN, thereby increasing the number of feature maps. The encoder may apply the set of CNNs in series to the projection dataset. Each CNN may output a predefined number of feature maps as an input for the subsequent CNN. The number of feature maps may depend on the number of filters at the corresponding CNN. Furthermore, the size of each feature map may depend on the size of the filter at the corresponding CNN. At each CNN of the encoder, the number of feature maps may double at each CNN and the size of each individual feature map may be halved (e.g., 288×269×1 to 144×192×1 and so forth).

Using the set of feature maps outputted by the encoder, the decoder may generate a reconstructed image. The decoder may include another series of transform layers. For example, the decoder may include another set of CNNs along with a corresponding upsampler layer. Prior to application of the CNN layer to the set of features maps, the upsampler layer may upsample each feature to increase the size (e.g., double). Each CNN may include a convolutional layer, a batch normalization layer, and a rectifier linear layer. The convolutional layer at the decoder may include a predefined number of filters. Each filter may be of a predefined size (e.g., 3×3). The number of filters across the convolutional layers may decrease at each successive CNN, thereby decreasing the number of feature maps. The decoder may apply the set of CNNs in series onto the set of feature maps. Each CNN may output a predefined number of feature maps as an input for the subsequent CNN. At each CNN of the decoder, the number of feature maps may halve at each CNN and the size of each individual feature map may be doubled (e.g. from 18×24×1 to 37×46×1). The resultant feature map may be used to generate the reconstructed image of the original projection dataset.

Based on the reconstructed image, the encoder-decoder model may be modified to improve performance of the reconstruction. The training data may include simulated reconstructed images using other techniques applied onto the projection dataset. By comparing between the reconstructed image from the encoder-decoder model and the reconstructed image from the training data, an error measure between the two images may be calculated. The error measure may be indicative of any deviation from the reconstructed image of the training data present in the reconstructed image from the encoder-decoder model. The error measure may be used to adjust various parameters of the encoder-decoder model to improve the accuracy and quality of the reconstruction. For example, the filters of the convolutional layers at the encoder or decoder may be set based on the error measure.

One aspect of the present disclosure is directed to a method of reconstructing biomedical images. An image reconstructor executing on one or more processors may identify a projection dataset derived from a tomographic biomedical imaging scan. The image reconstructor may apply, to the projection dataset an encoder-decoder model for reconstructing tomographic biomedical images from projection data. The encoder-decoder model may include an encoder. The encoder may include a first series of transform layers to generate a first plurality of feature maps using the projection dataset. The encoder-decoder may include a decoder. The decoder may include a second series of transform layers to generate a second plurality of features maps using the first plurality of feature maps from the encoder. The image reconstructor may generate a reconstructed tomographic biomedical image based on the second plurality of feature maps generated by the decoder of the encoder-decoder model.

In some embodiments, identifying the projection dataset may include identifying the projection dataset by acquiring two-dimensional slices of a second projection dataset generated from the tomographic biomedical imaging scan. The projection dataset may have a first plurality of data counts defined in two-dimensions. The second projection dataset may have a second plurality of data counts defined in three-dimensions. The second plurality of data counts may number greater than the first plurality of data counts.

In some embodiments, identifying the projection dataset may include applying an interpolation procedure onto a second projection dataset having a plurality of data counts generated from the tomographic biomedical imaging scan to generate the projection dataset corresponding to a subset of the plurality of data counts. In some embodiments, identifying the projection dataset may include identifying a second projection dataset generated from the tomographic biomedical imaging scan. The second projection dataset may include a plurality of data counts defined in three-dimensions. In some embodiments, identifying the projection dataset may include identifying, in accordance with an interpolation procedure, a data plane from the second projection dataset corresponding to one dimension of the plurality of data counts as the projection dataset.

In some embodiments, applying the encoder-decoder model further comprises may include the encoder-decoder model to the first projection dataset. The encoder-decoder model may include the encoder. The encoder may include the first series of transform layers. Each transform layer may include a convolutional layer. Each convolutional layer of the first series may have a size less than or equal to a size of a previous convolutional layer in the first series of transform layers to generate the first plurality of feature maps. The encode-decoder model may include the decoder. The decoder may include the second series of transform layers. Each transform layer may have a convolutional layer. Each convolutional layer of the second series may have a size greater than or equal to a size of a previous convolutional layer in the second series of transform layers to generate the second plurality of features maps.

In some embodiments, applying the encoder-decoder model further comprises may include the encoder-decoder model to the first projection dataset. The encoder-decoder model may include the encoder. The encoder may include the first series of transform layers. At least one transform layer of the first series may have a non-linear input-to-output characteristic. The decoder may include the second series of transform layers. At least one transform layer of the second series having a non-linear input-to-output characteristic to generate the reconstructed image in a single application of the encoder-decoder model.

In some embodiments, the image reconstructor may train the encoder-decoder model using training data. The training may include a sample projection dataset and a sample reconstructed tomographic image derived from the sample projection dataset to compare with the reconstructed tomographic biomedical image generated based on the second plurality of feature maps generated by the decoder of the encoder-decoder model.

Another aspect of the present disclosure is direct to a method of training models to reconstruct biomedical images. An image reconstructor executing on one or more processors may identify training data. The training data may include a projection dataset and a first reconstructed tomographic image derived from the projection dataset. The image reconstructor may apply, to the projection dataset an encoder-decoder model for reconstructing tomographic biomedical images from projection data. The encoder-decoder model may include an encoder. The encoder may include a first series of transform layers to generate a first plurality of feature maps using the projection dataset. The encoder-decoder may include a decoder. The decoder may include a second series of transform layers to generate a second plurality of features maps using the first plurality of feature maps from the encoder. The image reconstructor may generate a second reconstructed tomographic biomedical image based on the second plurality of feature maps generated by the decoder of the encoder-decoder model. The image reconstructor may determine an error measure between the first reconstructed tomographic biomedical image from the training data and the second reconstructed tomographic biomedical image generated from the encoder-decoder model. The error measure may indicate at least one difference between the first reconstructed tomographic biomedical image and the second reconstructed tomographic biomedical image. The image reconstructor may modify at least one parameter of the encoder-decoder model based on the error measure between the first reconstructed tomographic biomedical image and the second reconstructed tomographic biomedical image.

In some embodiments, identifying the projection dataset may include identifying the projection dataset by acquiring two-dimensional slices of a second projection dataset generated from the tomographic biomedical imaging scan. The projection dataset may have a first plurality of data counts defined in two-dimensions. The second projection dataset may have a second plurality of data counts defined in three-dimensions. The second plurality of data counts may number greater than the first plurality of data counts. In some embodiments, identifying the projection dataset may include applying an interpolation procedure onto a second projection dataset having a plurality of data counts generated from the tomographic biomedical imaging scan to generate the projection dataset corresponding to a subset of the plurality of data counts.

In some embodiments, determining the error measure may include calculating the error measure including at least one of a mean squared error, a mean integrated squared error, a quadratic loss, a relative entropy measure, and a norm between the first reconstructed tomographic biomedical image and the second reconstructed tomographic biomedical image. In some embodiments, modifying the at least one parameter of the encoder-decoder model may include reducing a number of connections between at least one of the first series of transform layers in the encoder and the second series of transform layers in the decoder based on the error measure between the first reconstructed tomographic biomedical image and the second reconstructed tomographic biomedical image. In some embodiments, the image reconstructor may modify at least one parameter of the encoder-decoder model based on a second error measure between a first reconstructed image derived from second training data and a second reconstructed image generated by the encoder-decoder model using the second training data. The second training data may exclude tomographic biomedical images.

In some embodiments, applying the encoder-decoder model further comprises may include the encoder-decoder model to the first projection dataset. The encoder-decoder model may include the encoder. The encoder may include the first series of transform layers. Each transform layer may include a convolutional layer. Each convolutional layer of the first series may have a size less than or equal to a size of a previous convolutional layer in the first series of transform layers to generate the first plurality of feature maps. The encode-decoder model may include the decoder. The decoder may include the second series of transform layers. Each transform layer may have a convolutional layer. Each convolutional layer of the second series may have a size greater than or equal to a size of a previous convolutional layer in the second series of transform layers to generate the second plurality of features maps.

Another aspect of the present disclosure is directed to a system for reconstructing biomedical images. The system may include a projection preparer executable on one or more processors. The projection preparer may identify a projection dataset derived from a tomographic biomedical imaging scan. The system may include an encoder-decoder model executable on the one or more processors. The encoder-decoder model may reconstruct reconstructing tomographic biomedical images from projection data. The encoder-decoder model may include an encoder. The encoder may include a first series of transform layers to generate a first plurality of feature maps using the projection dataset. The encoder-decoder may include a decoder. The decoder may include a second series of transform layers to generate a second plurality of features maps using the first plurality of feature maps from the encoder. The system may include a reconstruction engine executable on the one or more processors. The reconstruction engine may apply the encoder-decoder model to the projection dataset to generate a reconstructed tomographic biomedical image based on the second plurality of feature maps generated by the decoder of the encoder-decoder model.

In some embodiments, the projection preparer may identify the projection dataset by acquiring two-dimensional slices of a second projection dataset generated from the tomographic biomedical imaging scan. The projection dataset may have a first plurality of data counts defined in two-dimensions. The second projection dataset may have a second plurality of data counts defined in three-dimensions. The second plurality of data counts may number greater than the first plurality of data counts.

In some embodiments, the projection preparer may apply an interpolation procedure onto a second projection dataset having a plurality of data counts generated from the tomographic biomedical imaging scan to generate the projection dataset corresponding to a subset of the plurality of data counts.

In some embodiments, each transform layer of first series in the encoder may have a convolutional layer. Each convolutional layer of the first series may have a size less than or equal to a size of a previous convolutional layer in the first series of transform layers to generate the first plurality of feature maps. In some embodiments, each transform layer of the second series in the decoder may have a convolutional layer. Each convolutional layer of the second series may have a size greater than a size of a previous convolutional layer in the second series of transform layers to generate the second plurality of features maps. In some embodiments, the reconstructor engine may apply the encoder-decoder model with a single operation to the projection dataset to generate the reconstructed tomographic biomedical image.

In some embodiments, the system may include a model trainer executable on the one or more processors. The model trainer may train the encoder-decoder model using training data. The training data may include a sample projection dataset and a sample reconstructed tomographic image derived from the sample projection dataset to compare with the reconstructed tomographic biomedical image generated based on the second plurality of feature maps generated by the decoder of the encoder-decoder model.

BRIEF DESCRIPTION OF THE FIGURES

The foregoing and other objects, aspects, features, and advantages of the disclosure will become more apparent and better understood by referring to the following description taken in conjunction with the accompanying drawings, in which.

DETAILED DESCRIPTION

Figure 1A:
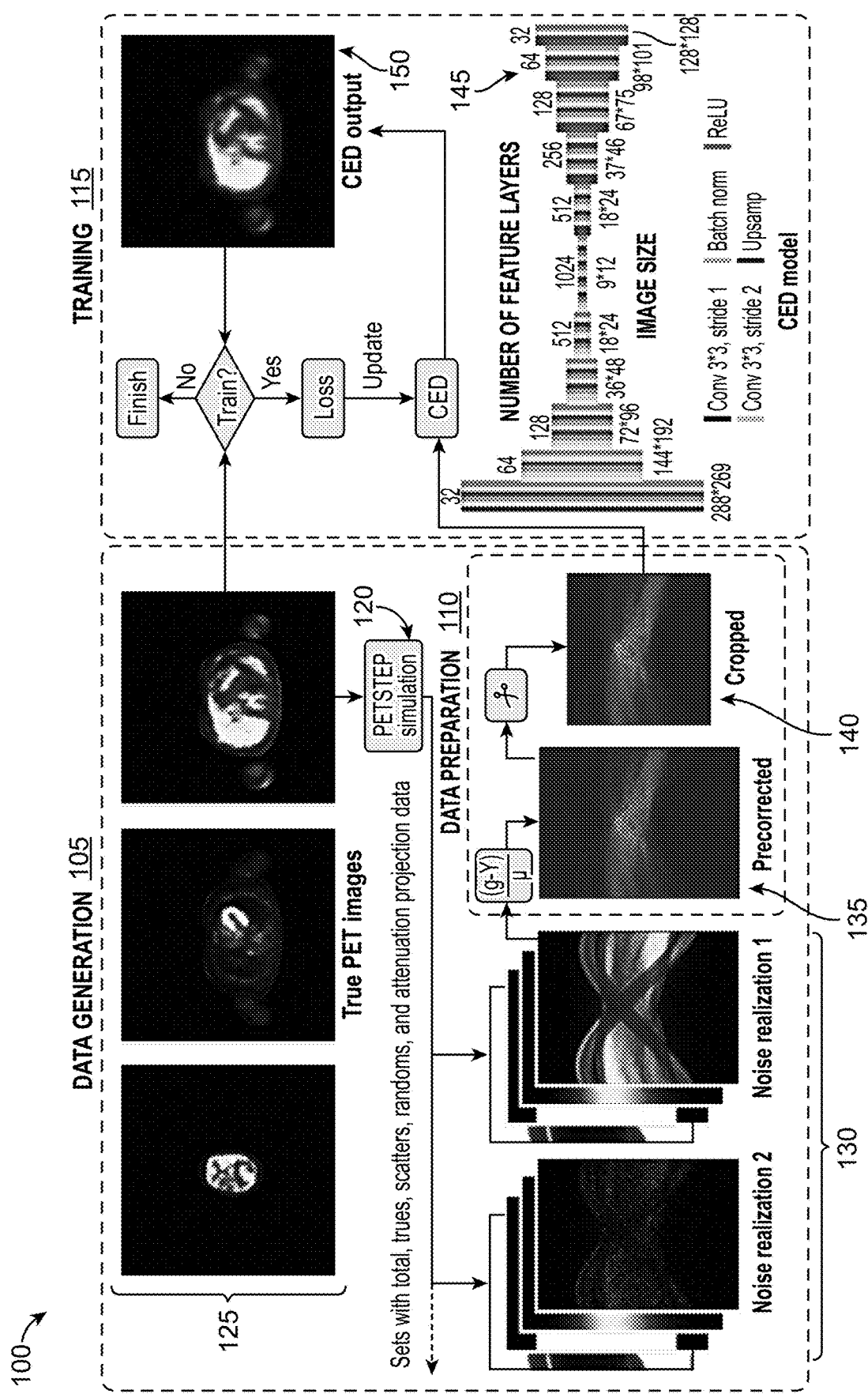
FIG. 1A depicts a schematic of a reconstruction pipeline and the convolutional encoder-decoder (CED) architecture.

Following below are more detailed descriptions of various concepts related to, and embodiments of, inventive systems and methods for processing immobilization molds. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

Section A describes embodiments of systems and methods of training an encoder-decoder model for reconstructing biomedical images and applying the encoder-decoder model for reconstructing biomedical images.

Section B describes systems and methods of using two-dimensional slicing in training an encoder-decoder model for reconstructing biomedical images and applying the encoder-decoder model to reconstruct biomedical images.

Section C describes a network environment and computing environment which may be useful for practicing various computing related embodiments described herein.

It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

A. Systems and Methods of Reconstructing Biomedical Images

The internal anatomical and physiological structure of a body may be acquired using biomedical imaging techniques of various modalities, such as radiography (e.g., X-rays and fluoroscopy), magnetic resonance imaging (MRI), ultrasonography, tactile imaging (elastography), photoacoustic imaging, functional near-infrared spectroscopy, and nuclear medicine functional imaging (e.g., positron emission tomography (PET) and single-photo emission computed tomography (SPECT)), among others.

One modality of biomedical imaging may include PET, widely used for numerous clinical, research, and industrial applications, due to ability to image functional and biological processes in vivo. PET is a cornerstone of modern radiology. Of all these applications, PET's integral role in cancer diagnosis and treatment is perhaps its most important. PET is able to detect in vivo radiotracer concentrations as low as picomolar. The ability to detect cancer and metastases in whole body scans fundamentally changed cancer diagnosis and treatment. This extreme sensitivity enables earlier and more precise diagnosis and staging. The early diagnosis of cancer is strongly correlated with outcome, as is early intervention in treatment management, where ineffective treatments can be stopped and more effective ones substituted in their place. All the benefits of PET in cancer care strongly relies on PET image quality however, making it a necessity with reliable, high quality, and quantitative images.

One of the main bottlenecks in the clinical application is the time it takes to reconstruct the anatomical image from the deluge of data in PET imaging. State-of-the art methods based on expectation maximization can take hours for a single patient and depend on manual fine-tuning by medical physicists. This results not only in financial burden for hospitals but more importantly leads to addition distress for patients.

The present disclosure relates to a PET image reconstruction technique based on a deep convolutional encoder-decoder network, that takes raw PET projection data as input and directly outputs full PET images. Using realistic simulated data, the deep convolutional encoder-decoder network is able to reconstruct images 17 times faster, and with comparable or higher image quality (in terms of root mean squared error) relative to conventional iterative reconstruction techniques.

In PET studies, the subject is injected with a tracer labeled with a positron emitting radionuclide, where the subsequent physical decay of the nuclide will lead to two emitted annihilation photons that can be detected by the PET camera. The raw PET tomographic data is typically stored in 2D histograms called sinograms. Each element in a sinogram represents the number of coincidence detections in a particular detector pair that were emitted from back-to-back photons emanating from a positron/electron annihilation event. As a result, these detector pairs can be thought of as representing projections of the underlying activity distribution onto planes perpendicular to the lines connecting the detector pairs.

Projection data cannot be directly interpreted by an observer. However, images that represent estimates of the tracer distribution function can be reconstructed via an inverse problem. This is known as image reconstruction. The inverse problems for PET image reconstruction represent explicit models of the mean values of the physical system, where a particular model's inverse represents a solution to the image reconstruction problem. Unfortunately, the data that these models use are from random processes, which lead to data/model inconsistency and an ill posed problem. Because of this, a number of simplifying assumptions are made to make the problem tractable. These include the use of a discrete linear system to model the data to image mapping, simplified statistical models to account for the degree of data/model inconsistency, and regularization to control the data over fitting problem.

To deal with these problems, various PET image reconstruction techniques exist, the most common ones being analytical filtered back-projection (FBP), and maximum likelihood (ML) methods such as maximum-likelihood expectation maximization (MLEM) or its incremental update version, ordered subset expectation maximization (OSEM). Typically, however, images resulting from these standard methods suffer from data/model mismatches, data inconsistency, and data over-fitting, which can manifest as artifacts such as streaks and noise in the reconstructed images. As a result, the reconstructed images are generally filtered at the end of the reconstruction process. In the case of ML methods, regularization can be used to reduce the fitting noise in the reconstructed images. However, while regularization for PET image reconstruction has been around for a while, regularization requires a large number of iterations to make its benefits apparent, and as a result, has only recently been used clinically. Nonetheless these methods have been successful in providing physicians with crucial information concerning patient state, or researchers with better insight into the bimolecular properties of biological systems.

While, these image reconstruction methods have been successful, there are still some aspects of the process that can be improved. Both the system and statistical models contain a number of simplifications that contribute to the system model mismatches. These include the simplified photon/electron (positron) transport models, simplified geometry, and the neglect of other noise sources, such as dead time. Regularization, in particular, is an open problem in PET image reconstruction. Many regularization models have been proposed but there is no clear consensus on how to choose between them. The use of a deep network carries some advantages in each of these areas. The deep network at once can be trained to learn the inverse solution to the inverse problem in the presence of noise. That is, the deep network learns the inverse of the physical model, the appropriate statistical model, and the regularize model that best fits the character of the data.

Another advantage of a using a deep network for reconstruction is its potential for computational efficiency. The PET inverse problem is generally cast as a minimization problem and solved via a gradient descent scheme (or something equivalent). At each step of the descent at least two multiplications by the PET system matrix is required. The PET system matrix is very large and these steps are expensive to compute, especially when performing multiple iterations. Viewing the deep network as an inverse to the PET system model, one can envision it as performing a single one of these steps, where the step now represents the inverse operator. Hence, the present disclosure describes an encode-decoder network that solves the PET reconstruction inverse problem directly.

In recent years, deep learning has shown great potential in many medical image restoration, segmentation, and analysis applications. In particular, encoder-decoder architectures have been readily used for these purposes. Convolutional encoder-decoder (CED) models are capable of stepwise compressing the input data into a latent space representation, and then stepwise reconstructing that representation into a full dataset. In the past, CED models have been utilized in post processing methods using reconstructed images as network input to restore image quality and reduce image defects and noise. It is less explored how to use deep learning methods within the PET image reconstruction process itself, i.e. as part of generating PET images directly from raw PET projection data. A 3 layer CNN has been considered to optimize the regularizing term in iterative CT reconstruction. Although the CNN is part of the reconstruction loop, the 2 layer CNN based method still resembles a conventional regularized iterative least squares approach where the system matrix A has to be known. Also using the concept of iterative CNN reconstruction, a residual convolutional autoencoder within an ML framework to denoise PET images has also been considered.

One of the main bottlenecks in the clinical application of PET is the time it takes to reconstruct the anatomical image from the deluge of data in PET imaging. State-of-the art methods based on expectation maximization can take hours for a single patient and depend on manual fine-tuning by medical physicists. This results not only in financial burden for hospitals but more importantly leads to addition distress for patients.

The present disclosure relates to a new field of direct deep learning-based tomographic image reconstruction. According to some aspects, the present disclosure relates to designing a deep convolutional encoder-decoder architecture that directly and quickly reconstructs PET raw projection data into high quality images. According to some aspects, the present disclosure relates to a PET image reconstruction technique based on a deep convolutional encoder-decoder network, that takes raw PET projection data as input and directly outputs full PET images. Using realistic simulated data, the deep convolutional encoder-decoder network is able to reconstruct images 17 times faster, and with comparable or higher image quality (in terms of root mean squared error) relative to conventional iterative reconstruction techniques.

1. Emission Computed Tomography Image Reconstruction

Emission computed tomography (ECT) image reconstruction is based on a Poisson noise model given by $$g = \text{Poisson}\{Af + \gamma\} \quad (1)$$

where g is the measured projection data, A is the linear projection operator, $f$ is the unknown activity distribution to be estimated, and $\gamma$ is the additive counts from random and scatter events. This model can be solved by minimizing the residual of KL-divergence of the data model and a regularization term, which results in the minimization problem given by $$f = \underset{f}{\arg\min} \{\langle Af, 1 \rangle - \langle \log Af + \gamma, g \rangle + \lambda R(f)\}, \quad (2)$$

where $\langle \cdot, \cdot \rangle$ is the inner product, $R(f)$ is a regularization function, and $\lambda$ the regularization weight. In this form the physical aspects of the model (e.g., geometry and statistical distribution) are accounted for by the KL-divergence term.

However, the model in Equation (2) contains a number of assumptions. These include the approximation of the geometric relationship between the image and detectors, the associated point spread function, the estimate of the additive count distribution, the validity of the Poisson statistical model as applied to the actual data, and the functional form of the regularizer. In particular, the optimal regularization function is not generally known and is an active area of research. As a result, while the mathematical description in Equation (2) provides a well-defined functional form, it relies on the assumption that its constituent components are good approximations of the true physical system. Poor approximations of these components may reveal themselves as data/model inconsistency, but this provides little insight into how to improve them.

On the other hand, a deep learning network has the potential to learn each of these aspects of the model from the data itself. The network learns the correct geometric, statistical, and regularization models, provided the training examples are realistic. As a result, knowledge of the system geometry, data statistical properties, and regularization do not need to be explicitly included in the network model. However, both the geometry and statistical properties may still be implicitly included through the model used to create the training data. In the present disclosure, because these networks can learn rather than using defined statistical properties of the data, precorrected data can be used, where the $i^{th}$ precorrected data element is given by $$\hat{g}_i = \frac{g_i - \gamma_i}{\mu_i}, \quad (3)$$

where $\mu_i$ is the attenuation in the $i^{th}$ coincidence count. It is worth noting that precorrecting the data mixes its statistical properties and, as a result, is generally avoided in the inverse problem formulation due to its explicit use of a particular statistical model, Poisson in the case of PET.

The present disclosure relates to a novel PET image reconstruction approach, based on a deep convolutional encoder-decoder network, as opposed to traditional iterative reconstruction techniques.

Referring now to FIG. 1A, depicted a schema 100 of the reconstruction pipeline and the convolutional encoder-decoder (CED) architecture. The schema 100 may include a data generation process 105 and a training process 115. Each component in the schema 100 can be implemented using the components detailed herein below in conjunction with FIGS. 16A-D. While the schema 100 will be described herein in connection with PET, the schema 100 may be used with other modalities of biomedical imaging, such as radiography (e.g., X-rays and fluoroscopy), magnetic resonance imaging (MRI), ultrasonography, tactile imaging (elastography), photoacoustic imaging, functional near-infrared spectroscopy, and nuclear medicine functional imaging (e.g., single-photo emission computed tomography (SPECT)). The data generation process 105 is depicted on the left, and may include simulation with an image simulator 115, such as PETSTEP, resulting in projection datasets. Experimental setup of the deep learning training procedure is shown on the right.

The image simulator 120 can include one or more scripts, programs, algorithms, computer-executable instructions, or modules and is configured to generate one or more simulations for each of the images obtained by the image manager. The image simulator 120 may include a PET simulator, such as open-source PET simulation software PETSTEP. The image simulator 120 can be used to simulate PET scans and generate realistic PET data (e.g., true PET images 125) that includes effects of scattered and random coincidences, photon attenuation, counting noise, and image system blurring. In some embodiments, the image simulator 120 can model a GE D710/690 PET/CT scanner, with projection data of 288 angular×381 radial bins. This approach avoids too simplistic training data, for example by only adding Poisson noise (e.g., noise realization 130) to projection data, and thus enables the transferability of the trained network to clinical data. In some embodiments, the image simulator 120 can generate data sets with total projection data, with true projection data, with scatters, with randoms, and with attenuation projection data.

In some embodiments, the image simulator 120 can use ordered subset expectation maximization (OSEM) reconstructed 2D image slices of 128×128 pixels (700 mm field of view) from real PET whole-body patient scans as phantom input. In some embodiments, the image simulator can simulate a plurality of, for example 12, random activity levels of each image slice, resulting in a very large number of projection datasets (total, trues, scatters, randoms, and attenuation factors μ). In some embodiments, the noisy total projection data (e.g., noise realization 130) can have, on average, $1.4 \cdot 10^6$ total counts (range $3.7 \cdot 10^3$ to $3.4 \cdot 10^7$).

The original images were used as ground truth, and the simulated total projection data was used as network input after being precorrected for randoms, scatters and attenuation according to Equation (3). The precorrected projection data 135 was also cropped to generate cropped data 140 prior to input. The image field of view is circular with the same diameter as the image matrix size (here 128), leaving corners empty. This in turn leaves the radial projection data bins 1-56, and 325-381 always empty, which were cropped to reduce the number of network elements.

2. Dataset Description

The major bottleneck in many deep learning experiments is the limited size of available datasets and lack of labeled data. This problem was circumvented by generating labeled data synthetically. The open-source PET simulation software PETSTEP was used to simulate PET scans and generate realistic PET data that includes effects of scattered and random coincidences, photon attenuation, counting noise, and image system blurring. A GE D710/690 PET/CT scanner was modeled, with projection data of 288 angular×381 radial bins. This approach avoids too simplistic training data, for example by only adding Poisson noise to projection data, and thus enables the transferability of the trained network to clinical data.

The OSEM reconstructed 2D image slices of 128×128 pixels (700 mm field of view) from real PET whole-body patient scans were used as phantom input to PETSTEP. A total of 44 patients with 221 slices (eyes to thighs) each were used, where about 12 random activity levels of each image slice was simulated, resulting in 111,935 projection datasets (total, trues, scatters, randoms, and attenuation factors μ). The noisy total projection data had on average $1.4 \cdot 10^6$ total counts (range $3.7 \cdot 10^3$ to $3.4 \cdot 10^7$). The original 111,935 images were used as ground truth, and the simulated total projection data was used as network input after being precorrected for randoms, scatters and attenuation according to Equation (3). The precorrected projection data 135 was also cropped to generate cropped data 140 prior to input. The image field of view is circular with the same diameter as the image matrix size (here 128), leaving corners empty. This in turn leaves the radial projection data bins 1-56, and 325-381 always empty, which were cropped to reduce the number of network elements.

3. Encoder-Decoder Architecture

Figure 1B:
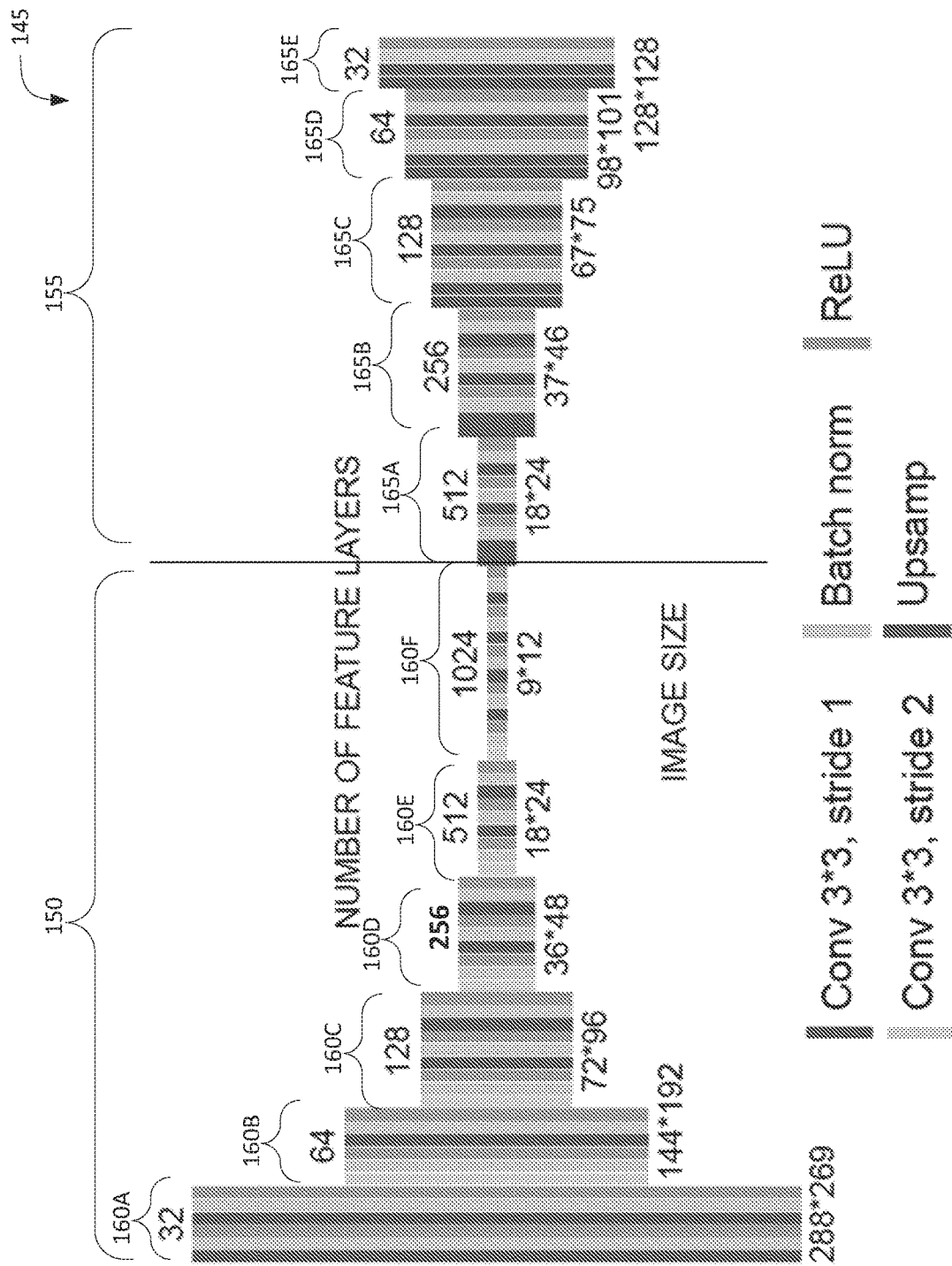
FIG. 1B depicts a schematic of the convolutional encoder-decoder (CED) architecture.

Referring to FIG. 1B, depicted is a schema of the convolutional encoder-decoder (CED) architecture 145. The CED architecture 145 may include an encoder 150 and a decoder 155. The encoder 150 may include a series of convolutional neural networks (CNNs) 160A-F. Each CNN 160A-F of the encoder 150 may include one or more convolutional layers, a batch normalization layer, and a rectified linear unit. The decoder 155 may also include a series of CNNs 165A-E. Each CNN 165A-E of the decoder 155 may include an upsampling layer, one or more convolutional layers, a batch normalization layer, and a rectified linear unit.

The encoder 150 may loosely mimic the VGG16 network architecture with modifications. The sinogram input data is of size 288×269×1, and the output 150 in image space is of size 128×128×1. The encoder 150 contracts the input data in a manner typical to CNNs. Each CNN 160A-F includes sequential blocks of 3×3 convolutions with stride 2 and a factor 2 increase in the number of output feature layers, followed by batch normalization (BN) and a rectified linear unit (ReLU). The encoder 150 output may include 1024 feature maps of size 9×9. Each feature is a non-linear function of an extensive portion of the input image (sinogram projection data). This fact is of special interest in this PET scenario since single points in the reconstructed image domain are represented by sinusoidal traces in the input domain. In other words, a large spread out portion of the input image data may be needed to infer each reconstructed image pixel.

The decoder 155 upsamples the contracted feature representation from the encoder 150 into PET images. Each CNN 165A-E in the decoder 155 path includes an upsampling layer, effectively doubling the image size, a 3×3 convolution that halves the number of feature layers, a BN layer, followed by a ReLU. The best performing CED network has a total of 31 convolutional layers.

TABLE 1

Parameterization of the six best encoder-decoder architectures in comparison to DeepRec.

| Name | Conv Layers | Feature Layers | BN | Opt |
|---|---|---|---|---|
| M1 | 20 | 256 | No | Adam |
| M2 | 20 | 256 | Yes | Adam |
| M3 | 23 | 512 | Yes | Adam |
| M4 | 31 | 1024 | Yes | Adam |
| DeepRec | 31 | 1024 | Yes | SGD |
| M6 | 36 | 2048 | Yes | Adam |

A number of different CED designs were implemented, with different number of convolutional layers and feature layer depths, as well as the Adam stochastic gradient optimization method, and an evaluation was performed to determine which one resulted in highest quality of reconstructed images. The models are denoted M1 through M6, and are seen in Table 1.

Figure 2A:
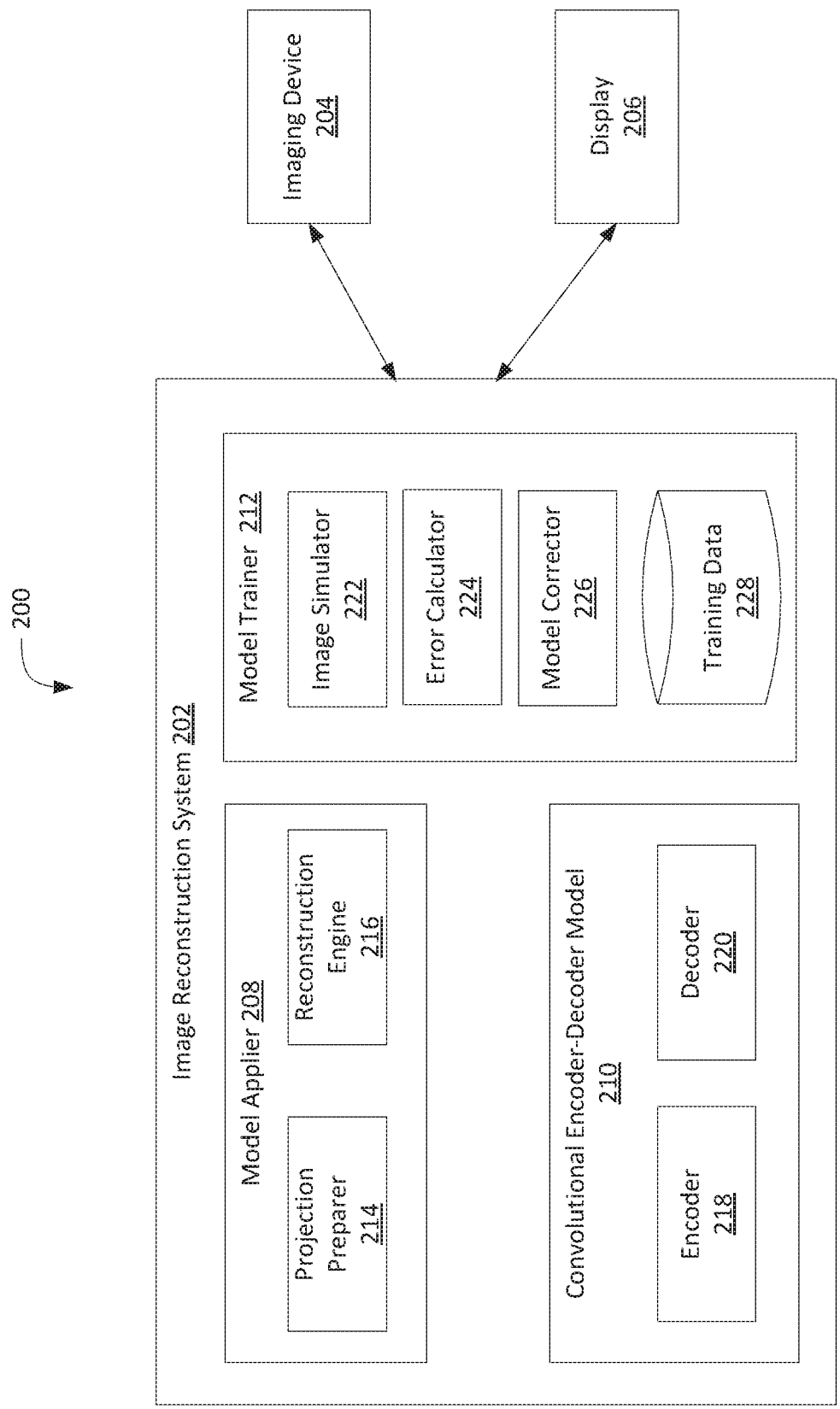
FIG. 2A depicts a block diagram of a system for training models for reconstructing images and reconstructing biomedical images using the models.

Referring now to FIG. 2A, depicted is a system 200 for training models for reconstructing biomedical images and using the models to reconstruct biomedical images. The system 200 may include an image reconstruction system 202, an imaging device 204, and a display 206. The image reconstruction system 202 may include a model applier 208, an encoder-decoder model 210, and a model trainer 212. The model applier 208 may include a projection preparer 214 and a reconstruction engine 216. The CED model 212 may include an encoder 218 and a decoder 220. The model trainer 212 may include an image simulator 222, an error calculator 224, a model corrector 226, and training data 228. Each of the component of system 200 listed above may be implemented using hardware (e.g., processing circuitry and memory) or a combination of hardware and software.

The imaging device 204 may perform a biomedical imaging scan on a subject to acquire a projection dataset. The imaging device 204 may be in any modality of biomedical imaging. The imaging device 204 may include a PET-computed tomography (CT) scanner, an X-ray CT Scanner, a SPECT CT scanner, an MRI scanner, an ultrasound scanner, and a photoacoustic scanner, among others. To scan, the imaging device 204 may be pointed toward a designated area on an outer surface of the subject (e.g., human or animal). As the subject is scanned, the imaging device 204 may generate the projection dataset corresponding to a cross-sectional plane or a volume of the subject through the predesignated area. The projection dataset may be two-dimensional or three-dimensional visualized representation of the subject, including the inner anatomical and physiological structure of the subject. The projection dataset may include one or more data counts. The projection dataset may include the one or more data counts in accordance with any data structure, such as an array, a binary tree, a matrix, a linked list, a heap, a hash table, a stack, or a queue, among others. Each data count may correspond to a coordinate of the scanned cross-sectional plane or the volume of the subject. When the cross-sectional plane of the subject is scanned, the projection dataset may be two-dimensional and the coordinates of the data counts may also be two-dimensional. When the volume of the subject is scanned, the projection dataset may be three-dimensional and the coordinates for the data counts may also be three-dimensional. The number of data counts in the projection dataset may depend on a sampling rate of the biomedical imaging scan performed by the imaging device 204. The imaging device 204 may be communicatively coupled with the image reconstruction system 202, and may provide the projection dataset to the image reconstruction system 202.

The projection preparer 214 of the model applier 208 may receive the projection dataset from the biomedical imaging scan performed by the imaging device 204. The projection preparer 214 may modify the projection dataset for further processing by the reconstruction engine 224. The projection preparer 214 may alter a size of the projection dataset. In some embodiments, the projection preparer 214 may identify the size of the projection dataset. The projection preparer 2414 may compare the size of the projection dataset with a predefined number. The number of data counts in the projection dataset may differ from the number permitted by the encoder-decoder model 210. If the size of the projection dataset is less than the predefined permitted number, the projection preparer 214 may reduce the number of data counts in the projection dataset. If the size of the projection dataset is greater than the predefined permitted number, the projection preparer 214 may increase the number of data counts in the projection dataset. If the size of the projection dataset is equal to the predefined permitted number, the projection preparer 214 may maintain the projection dataset.

In some embodiments, the projection preparer 214 may increase the number of data counts in the projection dataset to the predefined number. The number of data counts in the projection dataset may be less than the number permitted by the Encoder-decoder model 210. In some embodiments, the data count may be at a sampling rate less than a predefined sampling rate permitted by the Encoder-decoder model 210. The predefined number may be of any dimensions (e.g., 288×269×1 or 256×256×3), and may correspond to the number of data counts accepted by the Encoder-decoder model 210. In increasing the number of data counts, the projection preparer 214 may upsample the projection dataset. The projection preparer 214 may calculate a difference between the predefined number and the number of data counts in the projection dataset. The projection preparer 214 may perform zero-padding to the projection dataset by adding the identified difference of additional null data counts. The projection preparer 214 may then apply an interpolation filter to the zero-padded projection dataset to smooth the discontinuity from the zero-padding.

In some embodiments, the projection preparer 214 may reduce the number of data counts in the projection dataset to a predefined number. The number of data counts in the projection dataset may be greater than the number permitted by the CED model. In some embodiments, the data count may be at a sampling rate greater than a predefined sampling rate permitted by the encoder-decoder model 210. The predefined number may of any dimensions, and may correspond to the number of data counts permitted by the Encoder-decoder model 210. In reducing the number of data counts, the projection preparer 214 may downsample or decimate the projection dataset. The projection preparer 214 may calculate a ratio between the predefined number for the encoder-decoder model 210 and the number of data counts in the projection dataset. Based on the ratio, the projection preparer 214 may calculate a decimation factor for the projection dataset. The projection preparer 214 may apply a low-pass filter with a predetermined cutoff frequency to eliminate high-frequency components of the projection dataset. With the remainder of the projection dataset, the projection preparer 214 may downsample the projection dataset by the decimation factor by selecting a subset of the data counts corresponding to multiples of the decimation factor. The projection preparer 214 may also apply an anti-aliasing filter to the downsampled projection dataset to reduce effects of aliasing from downsampling. In some embodiments, the projection preparer 214 may reduce the number of data counts in the projection dataset to the predefined number by selecting a subset of the data counts in the projection dataset. The subset of the data counts may be at predetermined coordinates within the projection dataset (e.g., 128×128×3 about the middle pixel (64, 64)).

The reconstruction engine 216 may apply the encoder-decoder model 210 to the projection dataset. The reconstruction engine 216 may have a runtime mode and a training mode. In runtime mode, the reconstruction engine 216 may receive or access the projection dataset from the imaging device 214. In some embodiments, the projection dataset may have been processed by the projection preparer 214. In training mode, the reconstruction engine 216 may receive or access the projection dataset from the training data 228. Once the projection dataset is retrieved from the imaging device 204 or the training data 228, the reconstruction engine 216 may first apply the projection dataset to an input of the encoder-decoder model 210. In some embodiments, the reconstruction engine 216 may determine whether the projection dataset is two-dimensional or three-dimensional. When the projection dataset is determined to be two-dimensional, the reconstruction engine 216 may apply the entirety of the projection dataset to the encoder-decoder model 210. When the projection dataset is determined to be three-dimensional, the reconstruction engine 216 may divide the projection dataset into a set of two-dimensional slices. The reconstruction engine 216 may then apply each project dataset slice as an input of the encoder-decoder model 210. The encoder-decoder model 210 may use the projection dataset to generate a reconstructed image of the cross-sectional plane or the volume of the subject through the predesignated area scanned by the imaging device 204. The details of the functionalities and structure of the encoder-decoder model 210 are detailed herein below in conjunction with FIGS. 2B-2E.

Figure 2B:
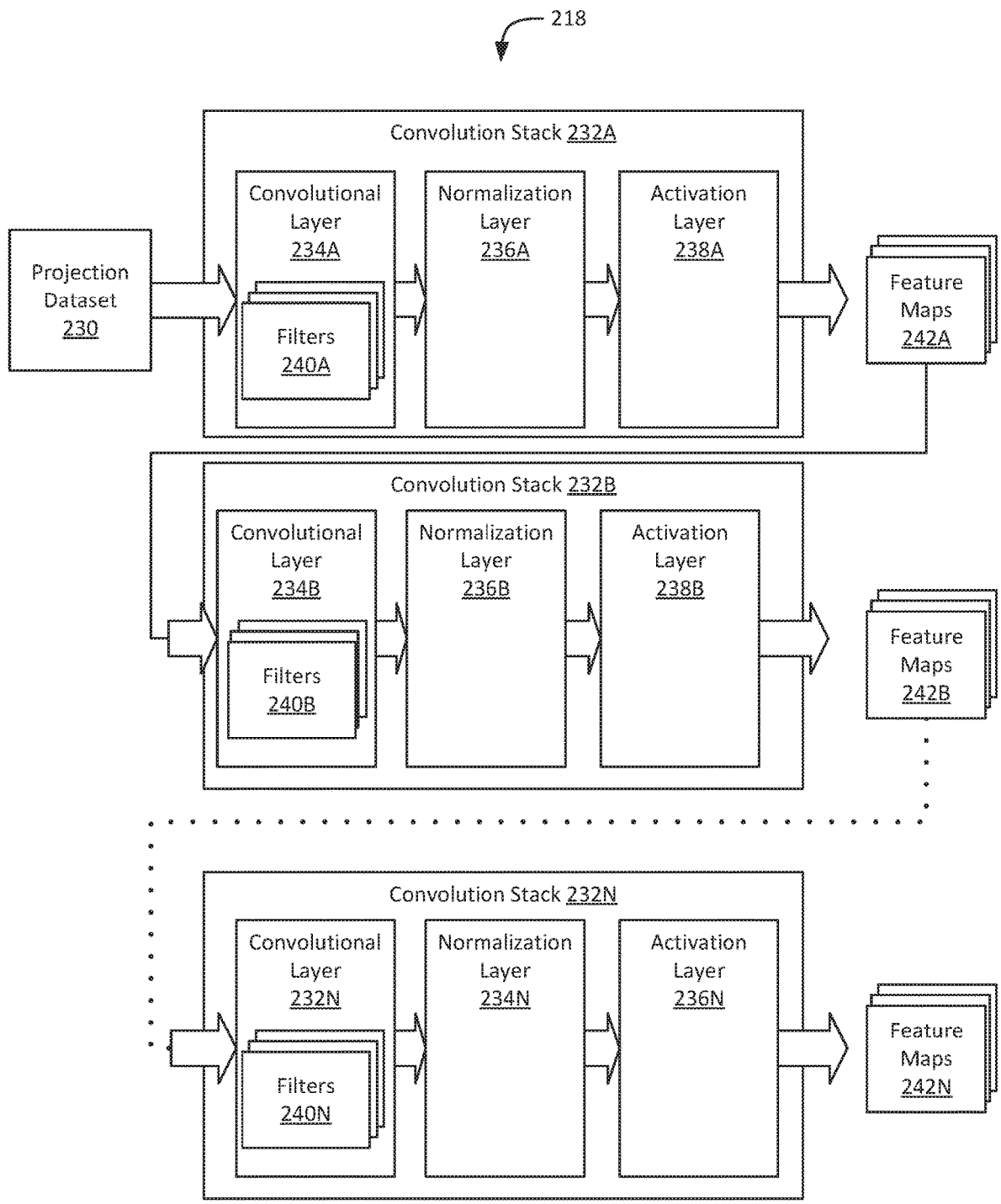
FIG. 2B depicts a block diagram of an encoder of a model for reconstructing images.

Referring now to FIG. 2B, depicted is the encoder 218 of the CED model 212 for reconstructing biomedical images. The encoder 218 may receive a projection dataset 230 provided by the reconstruction engine 216. The encoder 218 may use the projection dataset 230 to generate feature maps 242A-N. A size of each feature map 242A-N may be less than the size of the projection dataset 230. The encoder 218 may include one or more convolution stacks 232A-N (sometimes referred to as a convolutional neural network (CNN)). Each convolution stack 232A-N may include one or more convolutional layers 234A-N, one or more normalization layers 236A-N (sometimes referred to as batch normalization layers or BN layers), and one or more activation layers 238A-N (sometimes referred to as rectified linear units (ReLU)), among others. An output of one convolution stack 232A-N may be used as an input of a subsequent convolution stack 232A-N. The output of each convolution stack 232A-N may include one or more feature maps 242A-N. Subsequent to the first convolutional layer 232A-N, the input of each convolution stack 232A-N may be the feature maps 242A-N generated by the previous convolution stack 232A-N. The size of the input projection dataset 230 or feature map 242A-N may be less than the size of the output feature map 242A-N.

In each convolution stack 232A-N, the convolutional layer 234A-N may include one or more filters 240A-N (sometimes referred to as kernels or feature detectors). Each filter 240A-N may be a function to apply to the input of the convolutional layer 234A-N over the predetermined size at a predetermined stride (e.g., ranging from 1 to 64) to generate an output. The function of the filter 240A-N may include one or more parameters (sometimes referred to as weights) to apply to the input. In some embodiments, the one or more parameters may correspond to or may each include a multiplicative factor. The one or more parameters may be set, adjusted, or modified by training. Each filter 240A-N may be of a predetermined size (e.g., ranging from 3×3×1 to 1024×1024×3). The size of the filters 240A-N may be the same for a single convolutional layer 234A-N of the same convolution stack 232A-N. For example, if the first convolution stack 232A had two convolutional layers 234A and 234B, the size of all the filters 240A and 240B for the two convolutional layers 234A and 234B may all be 256×256×1. The size of the filters 240A-N may differ among the convolution stacks 232A-N. In some embodiments, the size of the filters 240A-N of one convolution stack 232A-N may be less than the size of the filters 240A-N of the previous convolution stack 232A-N. For example, the size of the filters 240A of the first convolutional layer 234A in the first convolution stack 232A may be 256×256×1, whereas the size of the filters 240B of the second convolutional layer 234B in the second convolution stack 232B may be 128×128×1. A number of filters 240A-N (sometimes referred to as depth or filter depth) may differ among the convolutional layers 234A-N. In some embodiments, the number of filters 240A-N of one convolution stack 232A-N may be greater than the number of filters 240A-N of the previous convolution stack 232A-N. For example, the number of filters 240A of the first convolutional layer 234A in the first convolution stack 232A may be 32. The number of filters 240B of the second convolutional layer 234B in the second convolution stack 232B may be 64.

In some embodiments, a single convolution stack 232A-N may include multiple convolutional layers 234A-N. The filters 240A-N of the multiple convolutional layers 234A-N may differ from one another. In some embodiments, a first convolution layer 234A-N of the convolution stack 232A-N may have a predetermined stride of a first value, whereas a second convolutional layer 234A-N of the same convolution stack 232A-N may have a predetermined stride of a second value that may be different from the first value. In some embodiments, the one or more parameters of a first convolutional layer 234A-N of the convolution stack 232A-N may differ from at least one of the one or more parameters of a second convolution layer 248A-N of the same convolution stack 244A-N.

Each convolutional layer 234A-N may apply the filters 240A-N to the input to generate an output. The input may include the projection dataset 230 at the first convolution layer 234A of the first convolution stack 232A or the feature map 242A-N generated by the previous convolution stack 232A-N for all subsequent convolution stacks 232B-N. The output may correspond to feature maps 242A-N prior to the application of the normalization layer 236A-N and the activation layer 238A-N. The convolutional layer 234A-N may apply the filter 240A-N to the data counts of the input within the predetermined size at the predetermined stride. In some embodiments, the convolutional layer 234A-N may traverse the data counts of the input to identify a subset of data counts numbering the predetermined size of the filter 240A-N. For each filter 240A-N, the convolutional layer 234A-N may apply the one or more parameters of the filter 240A-N to the identified subset of data counts to generate a subset output. In some embodiments, the application of the one or more parameters may be a matrix multiplication of the identified subset of data counts with the one or more parameters of the filter 240A-N. The subset output may correspond to a subset portion of the feature map 242A-N. The convolutional layer 234A-N may then identify a next subset of data counts numbering the predetermined size by shifting over by the predetermined stride. Once the next subset of data counts is identified, the convolutional layer 234A-N may repeat the application of the parameters of the filters 240A-N to generate the subset output.

With the traversal of all the data counts of the input, the convolutional layer 234A-N may aggregate the subset output to generate the output for the respective filter 240A-N. The output may correspond to one of the feature maps 242A-N. For example, one of the first filters 240A may correspond to one of the feature maps 242A and another of the first filters 240A may correspond to another of the feature maps 242A. A size of the feature maps 242A-N may depend on predetermined size of the filters 240A-N and the predetermined stride for the application of the filters 240A-N to the input. As a result, in some embodiments, as the predetermined size of the filters 240A-N at each convolutional stack 232A-N decrease relative to that of the previous convolutional stack 232A-N, the size of the feature maps 242A-N may decrease after each successive application of the convolutional layers 234A-N. The size of the feature map 242A-N may be less than the size of the original projection dataset 230. In addition, a number of the feature maps 242A-N may depend on the number of filters 240A-N at each convolutional layer 234A-N. Consequently, in some embodiments, as the number of filters 240A-N at each convolutional stack 232A-N relative to that of the previous convolutional stack 232A-N, the number of feature maps 242A-N may increase after each successive application of the convolutional layers 234A-N.

In each convolution stack 232A-N, the normalization layer 236A-N may also include another function to apply to the output of the previous convolutional layer 234A-N of the same convolution stack 232A-N. In some embodiments, the encoder 218 may lack normalization layers 236A-N on some or all of the convolution stacks 232A-N. The function of the normalization layer 236A-N may include one or more parameters to apply to the input. In some embodiments, the normalization layer 236A-N may modify the data counts of a single feature map 242A-N corresponding to the output of one of the filters at the previous convolutional layer 234A-N based on values of the data counts of the single feature map 242A-N. The normalization layer 236A-N may identify a range of values of the data counts of the single feature map 242A-N. From the range of values, the normalization layer 236A-N may identify a minimum value, a maximum value, and a difference between the minimum value and the maximum value for the data counts of the single feature map 242A-N. The normalization layer 236A-N may determine a transformation factor based on the minimum value, the maximum value, and the difference between the minimum value and the maximum value (e.g., as a linear function). The normalization layer 236A-N may then apply the transformation factor to all the data counts (e.g., multiply) of the single feature map 242A-N. In some embodiments, the normalization layer 236A-N may modify the data counts of all the feature maps 242A-N each corresponding to the output of one of the filters at the previous convolutional layer 234A-N based on values of the data counts across all the feature maps 242A-N. The normalization layer 236A-N may identify a range of values of the data counts across all the feature maps 242A-N. From the range of values, the normalization layer 236A-N may identify a minimum value, a maximum value, and a difference between the minimum value and the maximum value for the data counts. The normalization layer 236A-N may determine a transformation factor based on the minimum value, the maximum value, and the difference between the minimum value and the maximum value (e.g., as a linear function). The normalization layer 236A-N may then apply the transformation factor to all the data counts (e.g., multiply) across all feature maps 242A-N. The normalization layer 236A-N may maintain the size of each feature map 242A-N and the number of feature maps 242A-N outputted by the previous convolutional layer 234A-N.

In each convolution stack 232A-N, the activation layer 238A-N may also include another function to apply to the output of the previous convolutional layer 234A-N or normalization layer 236A-N. The function of the activation layer 238A-N may be an activation function, such as an identity function, a unit step function, a hyperbolic function, an arcus function, or a rectifier function (max(0, x)), among others. The activation function may be non-linear. The activation layer 238A-N may traverse all the feature maps 242A-N each corresponding to the output of one of the filters at the previous convolutional layer 234A-N. For each feature map 242A-N, the activation layer 238A-N may traverse all the data count. While traversing each data count, the activation layer 238A-N may apply the activation function to the data count to generate the output for the feature map 242A-N. As the activation function, the output of the activation layer 238A-N may be non-linear. The activation layer 238A-N may maintain the size of each feature map 242A-N and the number of feature maps 242A-N outputted by the previous convolutional layer 234A-N.

Figure 2C:
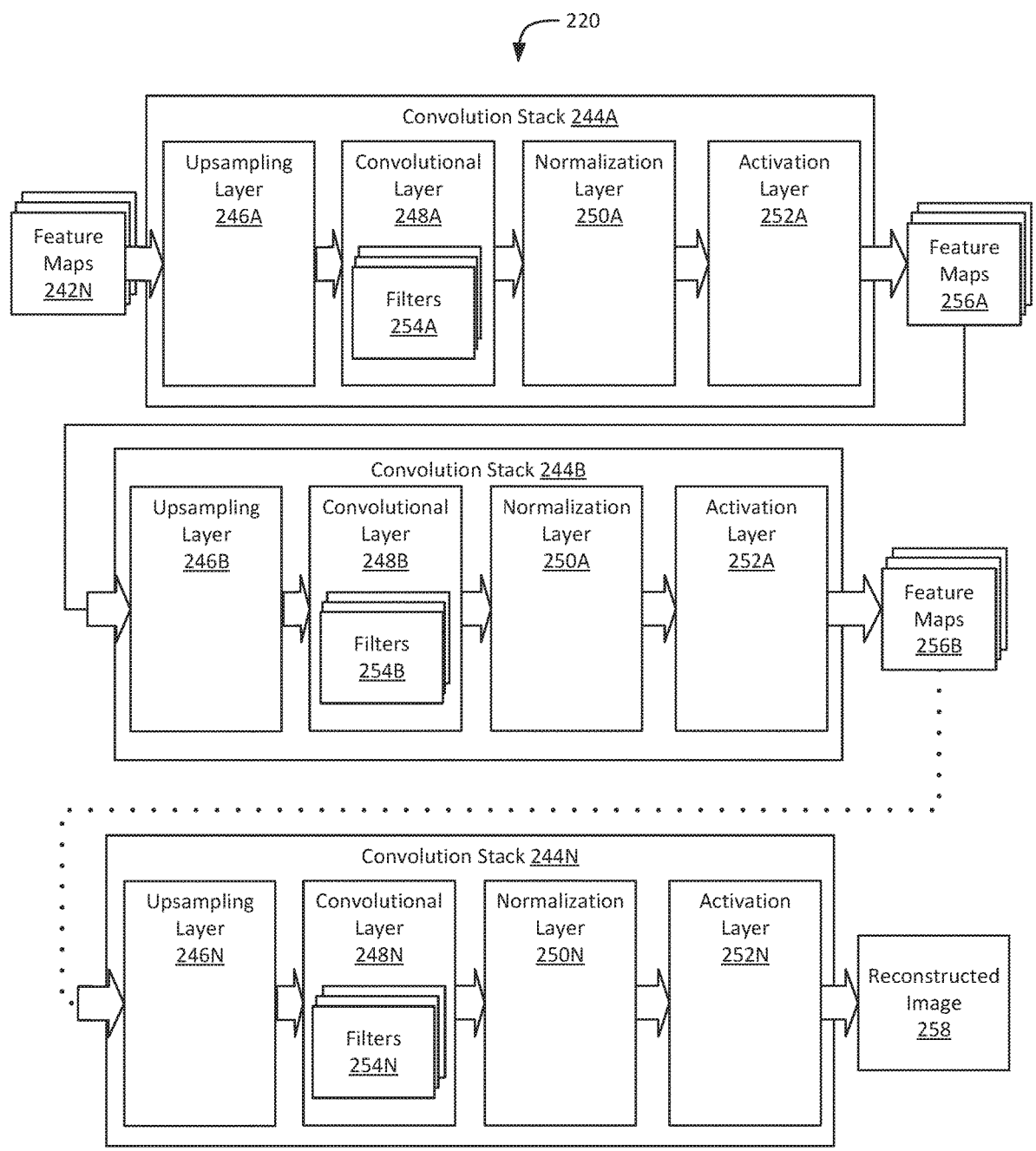
FIG. 2C depicts a block diagram of a decoder of a model for reconstructing images.

Referring now to FIG. 2C, depicted is the decoder 220 of the CED model 212 for reconstructing biomedical images. The decoder 220 may receive a projection dataset 230 provided by the reconstruction engine 216. The decoder 220 may use the projection dataset 230 to generate feature maps 256A-N. A size of each feature map 256A-N may be less than the size of the projection dataset 230. The decoder 220 may include one or more convolution stacks 244A-N (sometimes referred to as a convolutional neural network (CNN)). Each convolution stack 244A-N may include one or more upsampling layers 246A-N, one or more convolutional layers 248A-N, one or more normalization layers 250A-N (sometimes referred to as batch normalization layers or BN layers), and one or more activation layers 252A-N (sometimes referred to as rectified linear units (ReLU)), among others. An output of one convolution stack 244A-N may be used as an input of a subsequent convolution stack 244A-N. The output of each convolution stack 244A-N may include one or more feature maps 256A-N. Subsequent to the first convolutional layer 244A-N, the input of each convolution stack 244A-N may be the feature maps 256A-N generated by the previous convolution stack 244A-N. The size of the input projection dataset 230 or feature map 256A-N may be less than the size of the output feature map 256A-N.

At each convolution stack 244A-N, the upsampling layer 246A-N may increase the number of data counts of the input. In some embodiments, the upsampling layer 246A-N may increase the number of data counts for each feature map 242N or feature map 256A-N to a predefined number. The predefined number may be of any dimension, and may correspond to the number of data counts to be applied by the subsequent convolutional layer 248A-N. In some embodiments, the upsampling layer 246A-N may identify the number of data counts in the input. The upsampling layer 246A-N may then determine a predetermined multiple of the number of existing data counts in the input to determine the predefined number to which to increase the number of data counts. In some embodiments, the predefined multiple may be determined by the upsampling layer 246A-N for select dimensions. For example, the upsampling layer 246A-N may identify that the number of data counts in the input feature map 256A-N is 16×16×3, and may set the predefined number as twice the number of data counts to 32×32×3. With the determination of the predefined number, the upsampling layer 246A-N may perform zero-padding to the input by adding a number of null data counts to the input. The number of null data counts may equal or correspond to a difference between the number of existing data counts in the input and the predefined number. In some embodiments, the upsampling layer 246A-N may apply an interpolation filter to the zero-padded input to smooth any discontinuities arising from the zero-padding. The interpolation filter may be of the same size as the predefined number. The upsampling layer 246A-N may apply the interpolation filter to all the feature maps 242N or 256A-N corresponding to the input. In this manner, the size of the feature map 256A-N outputted by one upsampling layer 246A-N may be greater than the size of the feature map 256A-N outputted by the previous upsampling layer 246A-N. With each successive application of the upsampling layer 256A-N to the input, the size of each feature map 256A-N may increase. Moreover, the size of the feature map 256A-N outputted by each convolution stack 244A-N may be greater than the size of the feature maps 242N from the encoder 218.

At each convolution stack 244A-N, the convolutional layer 248A-N may include one or more filters 254A-N (sometimes referred to as kernels or feature detectors). Each filter 254A-N may be a function to apply to the input of the convolutional layer 248A-N over the predetermined size at a predetermined stride (e.g., ranging from 1 to 64) to generate an output. The function of the filter 254A-N may include one or more parameters to apply to the input. In some embodiments, the one or more parameters may correspond to or may each include a multiplicative factor. The one or more parameters may be set, adjusted, or modified by training. Each filter 254A-N may be of a predetermined size (e.g., ranging from 3×3×1 to 1024×1024×3). The size of the filters 254A-N may be the same for a single convolutional layer 248A-N of the same convolution stack 244A-N. For example, if the first convolution stack 244A had two convolutional layers 248A and 248B, the size of all the filters 254A and 254B for the two convolutional layers 248A and 248B may all be 256×256×1. The size of the filters 254A-N may differ among the convolution stacks 244A-N. In some embodiments, the size of the filters 254A-N of one convolution stack 244A-N may be greater than the size of the filters 254A-N of the previous convolution stack 244A-N. For example, the size of the filters 254A of the first convolutional layer 248A in the first convolution stack 244A may be 128×128×1, whereas the size of the filters 254B of the second convolutional layer 248B in the second convolution stack 244B may be 256×256×1. A number of filters 254A-N (sometimes referred to as depth or filter depth) may differ among the convolutional layers 248A-N. In some embodiments, the number of filters 254A-N of one convolution stack 244A-N may be less than the number of filters 254A-N of the previous convolution stack 244A-N. For example, the number of filters 254A of the first convolutional layer 248A in the first convolution stack 244A may be 64. The number of filters 254B of the second convolutional layer 248B in the second convolution stack 244B may be 32.

Each convolutional layer 248A-N may apply the filters 254A-N to the input to generate an output. The input may include the projection dataset 230 at the first convolution layer 248A of the first convolution stack 244A or the feature map 256A-N generated by the previous convolution stack 244A-N for all subsequent convolution stacks 244B-N. The output may correspond to feature maps 256A-N prior to the application of the normalization layer 250A-N and the activation layer 252A-N. The convolutional layer 248A-N may apply the filter 254A-N to the data counts of the input within the predetermined size at the predetermined stride. In some embodiments, the convolutional layer 248A-N may traverse the data counts of the input to identify a subset of data counts numbering the predetermined size of the filter 254A-N. For each filter 254A-N, the convolutional layer 248A-N may apply the one or more parameters of the filter 254A-N to the identified subset of data counts to generate a subset output. In some embodiments, the application of the one or more parameters may be a matrix multiplication of the identified subset of data counts with the one or more parameters of the filter 254A-N. The subset output may correspond to a subset portion of the feature map 256A-N. The convolutional layer 248A-N may then identify a next subset of data counts numbering the predetermined size by shifting over by the predetermined stride. Once the next subset of data counts is identified, the convolutional layer 248A-N may repeat the application of the parameters of the filters 254A-N to generate the subset output.

With the traversal of all the data counts of the input, the convolutional layer 248A-N may aggregate the subset output to generate the output for the respective filter 254A-N. The output may correspond to one of the feature maps 256A-N. For example, one of the first filters 254A may correspond to one of the feature maps 242A and another of the first filters 254A may correspond to another of the feature maps 242A. A size of the feature maps 256A-N may depend on predetermined size of the filters 254A-N and the predetermined stride for the application of the filters 254A-N to the input. As a result, in some embodiments, as with the convolution stacks 232A-N of the encoder 218, the size of the feature map 256A-N may decrease with the application of the convolutional layer 248A-N. In addition, a number of the feature maps 256A-N may depend on the number of filters 254A-N at each convolutional layer 248A-N. Consequently, in some embodiments, as the number of filters 254A-N increase at each convolutional stack 244A-N relative to that of the previous convolutional stack 244A-N, the number of feature maps 256A-N may decrease after each successive application of the convolutional layers 248A-N.

At each convolution stack 244A-N, the normalization layer 250A-N may also include another function to apply to the output of the previous convolutional layer 248A-N of the same convolution stack 244A-N. In some embodiments, the decoder 220 may lack normalization layers 250A-N on some or all of the convolution stacks 244A-N. The function of the normalization layer 250A-N may include one or more parameters to apply to the input. In some embodiments, the normalization layer 250A-N may modify the data counts of a single feature map 256A-N corresponding to the output of one of the filters at the previous convolutional layer 248A-N based on values of the data counts of the single feature map 256A-N. The normalization layer 250A-N may identify a range of values of the data counts of the single feature map 256A-N. From the range of values, the normalization layer 250A-N may identify a minimum value, a maximum value, and a difference between the minimum value and the maximum value for the data counts of the single feature map 256A-N. The normalization layer 250A-N may determine a transformation factor based on the minimum value, the maximum value, and the difference between the minimum value and the maximum value (e.g., as a linear function). The normalization layer 250A-N may then apply the transformation factor to all the data counts (e.g., multiply) of the single feature map 256A-N. In some embodiments, the normalization layer 250A-N may modify the data counts of all the feature maps 256A-N each corresponding to the output of one of the filters at the previous convolutional layer 248A-N based on values of the data counts across all the feature maps 256A-N. The normalization layer 250A-N may identify a range of values of the data counts across all the feature maps 256A-N. From the range of values, the normalization layer 250A-N may identify a minimum value, a maximum value, and a difference between the minimum value and the maximum value for the data counts. The normalization layer 250A-N may determine a transformation factor based on the minimum value, the maximum value, and the difference between the minimum value and the maximum value (e.g., as a linear function). The normalization layer 250A-N may then apply the transformation factor to all the data counts (e.g., multiply) across all feature maps 256A-N. The normalization layer 250A-N may maintain the size of each feature map 256A-N and the number of feature maps 256A-N outputted by the previous convolutional layer 248A-N.

At each convolution stack 244A-N, the activation layer 252A-N may also include another function to apply to the output of the previous convolutional layer 248A-N or normalization layer 250A-N. The function of the activation layer 252A-N may be an activation function, such as an identity function, a unit step function, a hyperbolic function, an arcus function, or a rectifier function (max(0, x)), among others. The activation function may be non-linear. The activation layer 252A-N may traverse all the feature maps 256A-N each corresponding to the output of one of the filters at the previous convolutional layer 248A-N. For each feature map 256A-N, the activation layer 252A-N may traverse all the data count. While traversing each data count, the activation layer 252A-N may apply the activation function to the data count to generate the output for the feature map 256A-N. As the activation function, the output of the activation layer 252A-N may be non-linear. The activation layer 252A-N may maintain the size of each feature map 256A-N and the number of feature maps 256A-N outputted by the previous convolutional layer 248A-N.

The reconstruction engine 216 may use the output from the last convolution stack 244N to generate the reconstructed image 258. The reconstructed image 258 may be of a predefined size. The size of the reconstructed image 258 may be less than the size of the projection dataset 230. In addition, the reconstructed image 258 may number less than the number of feature maps 242N or 256A-N. The reconstruction engine 216 may apply one or more image processing algorithms to the output of the last convolution stack 244N. The one or more image processing algorithms may include color correction, filtering, blurring, and contrast adjustment, among others. The reconstruction engine 216 may send the reconstructed image 258 to the display 206.

The display 206 may present or render an image output by the image reconstruction system 202. In some embodiments, the display 206 may present or render the reconstructed image generated by the CED model 212 of the image reconstruction system 202. The display 206 may include any monitor, such as a liquid crystal display (LCD), an organic light-emitting diode (OLED) monitor, and a cathode ray tube (CRT), among others. The display 206 may be communicatively coupled with the image reconstruction system 202, and may render and output the image from the image reconstruction system 202.

Figure 2D:
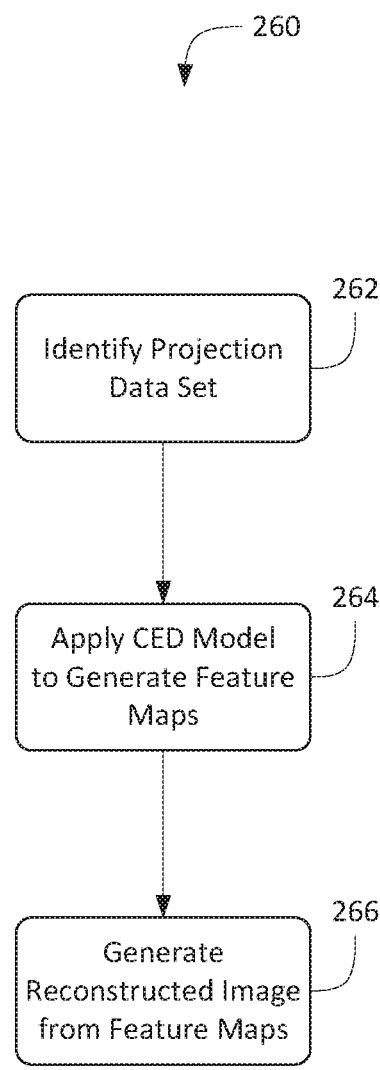
FIG. 2D depicts a flow diagram of a method of reconstructing biomedical images using convolutional encoder-decoder (CED) models.

Referring now to FIG. 2D, depicted is a method 260 of reconstructing biomedical images. The functionalities of the method 260 may be implemented or performed using the schema 100 as detailed in conjunction with FIG. 1, by the system 200 as detailed herein in conjunction with FIGS. 2A-2C, or the computing system 1600 described below in conjunction with FIG. 16A-D. In brief overview, an image reconstructor may identify a projection dataset (262). The image reconstructor may apply a convolution encoder-decoder (CED) model to the projection dataset to generate feature maps (264). The image reconstructor may generate a reconstructed image from the feature maps (266).

In further detail, the image reconstructor may identify a projection dataset (262). The image reconstructor may retrieve the projection dataset from a biomedical imaging device. The projection dataset may include one or more data counts. The one or more data counts may correspond to a cross-sectional area or a volume of a subject, including the internal anatomical and physiological structure of the subject. The one or more data counts may be of a predefined size. The image reconstructor may modify the number of data counts in the projection dataset. In some embodiments, the image reconstructor may up-sample or down-sample the projection dataset to modify the number of data counts.

The image reconstructor may apply a convolution encoder-decoder (CED) model to the projection dataset to generate feature maps (264). The CED model may include an encoder and a decoder. The encoder may contract the size of the projection data to generate a set of feature maps. The encoder may include a set of convolutional stacks. Each convolutional stack may include one or more convolution layers, one or more normalization layers, and one or more activation layers. Each convolution layer may include a predefined number of filters. The number of filters may increase at each successive convolution stack. Each filter may be of a predefined size. The image reconstructor may apply the projection dataset as the input of the CED model. The projection dataset may be successively applied to the set of convolutional stacks to generate a set of feature maps. Each feature map may correspond to one of the filters at the respective convolution layer. Each feature map may be of a predefined size based on the size of the input and the size of the filter. With each successive application of the convolutional stack (including the convolution layer, normalization layer, and the activation layer), the number of feature maps may increase while the size of each individual feature map may decrease.

The image reconstructor may generate a reconstructed image from the feature maps (266). The image reconstructor may continue to process the projection dataset through the decoder of the CED model. The decoder may use the projection dataset to generate the reconstructed image. The decoder may also include a set of convolutional stacks. Each convolutional stack may include one or more upsampling layers, one or more convolution layers, one or more normalization layers, and one or more activation layers. Each upsampling layer may increase the size of the feature map by zero-padding and applying an interpolation filter. Each convolution layer may include a predefined number of filters. The number of filters may decrease at each successive convolution layer. Each filter may be of a predefined size. The set of feature maps outputted by the encoder may be applied to the decoder. The output of one convolution stack at the decoder may successively be applied to next convolution stack of the decoder. Each feature map may correspond to one of the filters at the respective convolution layer. Each feature map may be of a predefined size based on the size of the input and the size of the filter. With each successive application of the convolutional stack (including the upsampling layer, the convolution layer, normalization layer, and the activation layer), the number of feature maps may decrease while the size of each individual feature map may increase. Using the one or more feature maps generated by the last convolution stack of the decoder, the image reconstructor may generate the reconstructed image.

4. Implementation and Training Procedure

Referring to FIG. 1A, the PETSTEP simulated dataset generated by the image simulator 120 was divided at random into three splits for training (72,649 projection datasets, 64%), validation (16,840 projection datasets, 16%) and testing (22,446 projection datasets, 20%). All three sets were kept separate.

The network was implemented in PyTorch, and trained on NVIDIA GTX 1080Ti GPUs. The mean squared error (MSE) was used as loss function, $$MSE = \frac{1}{n}\sum_{i=1}^{n}(x_i - y_i)^2, \quad (4)$$

where x is the model image, γ the ground truth, and n the number of image pixels. The model was optimized with stochastic gradient descent (SGD) with momentum on minibatches. The hyperparameters used for training were: learning rate 0.001; batch size 30; BN momentum 0.5; SGD momentum 0.9; bilinear upsampling. The model was optimized on the training set over 50 epochs, and the MSE was calculated on the validation set every 5th epoch. After finishing training, the model with optimal performance on the validation set was used on the test set.

5. Conventional Image Reconstruction

Referring back to FIG. 1A, apart from the deep reconstruction method described herein, as part of the training 115 the PET projection data was also reconstructed using conventional techniques: FBP and unregularized OSEM with 2 iterations and 16 subsets according to clinical standard. Typically for the GE D710/690, a transaxial 6.4 mm FWHM Gaussian postfilter is used together with a 3 point smoothing in the slice direction. Here only single slices were available, and the system only used the transaxial filter.

For additional performance evaluation, the relative root mean squared error (rRMSE) was used, $$rRMSE = \sqrt{MSE}/\bar{\gamma}. \quad (5)$$

Referring back to FIG. 2A, the model trainer 212 may use the reconstructed image 256 generated by the model applier 208 and the training data 228 to update the encoder-decoder model 210. In some embodiments, the training data 228 maintained by the model trainer 212 may include a training projection dataset. The training projection dataset may be two-dimensional or three-dimensional visualized representation of the subject, including the inner anatomical and physiological structure of the subject. The training projection dataset may be of any biomedical imaging modality, such as radiography (e.g., X-rays and fluoroscopy), magnetic resonance imaging (MRI), ultrasonography, tactile imaging (elastography), photoacoustic imaging, functional near-infrared spectroscopy, and nuclear medicine functional imaging (e.g., positron emission tomography (PET) and single-photo emission computed tomography (SPECT)), among others. The training projection dataset may include one or more data counts. The training projection dataset may include the one or more data counts in accordance with any data structure, such as an array, a binary tree, a matrix, a linked list, a heap, a hash table, a stack, or a queue, among others. Each data count may correspond to a coordinate of the scanned cross-sectional plane or the volume of the subject. When the cross-sectional plane of the subject is scanned, the training projection dataset may be two-dimensional and the coordinates of the data counts may also be two-dimensional. When the volume of the subject is scanned, the training projection dataset may be three-dimensional and the coordinates for the data counts may also be three-dimensional. The number of data counts in the training projection dataset may depend on a sampling rate of the biomedical imaging scan. In some embodiments, the training projection dataset may be the same as the projection dataset 230 used by the model applier 208 to generate the reconstructed image 256. In some embodiments, the training data 228 maintained by the model trainer 212 may include a training reconstructed image. The training reconstructed image may have been previously generated using the corresponding training projection dataset (e.g., using the image simulator 222 as detailed below). The training reconstructed image may be labeled as corresponding to the respective training projection dataset in the training data 228.

The image simulator 222 may access the training data 228 to retrieve the training projection dataset. With the training projection dataset, the image simulator 222 may generate a training reconstructed image. In some embodiments, the image simulator 222 may apply one or more simulation models to generate the training reconstructed image. The one or more simulation models may differ from the encoder-decoder model 210 used by the model applier 208. In some embodiments, the one or more simulation models may include PETSTEP and OSEM, among others. The one or more simulation models used by the image simulator 222 to generate the training reconstructed image may consume more time than the model applier 208 in generating the reconstructed image 256.

The error calculator 224 may compare the training reconstructed image with the model reconstructed image 256 generated by the model applier 216 using the encoder-decoder model 210. In some embodiments, the training reconstructed image may be generated by the image simulator 222 using the training projection dataset. In some embodiments, the training reconstructed image may be retrieved from the training data 228. The model reconstructed image 256 may be generated by the model applier 208 using the training projection dataset while in training mode. The error calculator 224 may determine an error measure between the training reconstructed image and the model reconstructed image 256. The error measure may indicate one or more differences between the training reconstructed image and the model reconstructed image 256. In some embodiments, the error calculator 224 may calculate the mean square error (MSE) as the error measure between the training reconstructed image and the model reconstructed image 256. In some embodiments, the error calculator 224 may calculate the root mean square error as the error measure. In some embodiments, the error calculator 224 may calculate a pixel-wise difference between the training reconstructed image and the model reconstructed image 256. Each image may be two-dimensional or three-dimensional, and may be of a predefined pixel size. The error calculator 224 may traverse the pixels of both the training reconstructed image and the model reconstructed image 256. For each corresponding pixel of the same coordinates, the error calculator 224 may calculate a difference between one or more values (e.g., intensity, gray-scale, or red-blue-green) of the pixel for the training reconstructed image versus the one or more values of the corresponding pixel for the model reconstructed image 256. Using the differences over the pixels, the error calculator 224 may calculate the error measure.

The model corrector 226 may update the encoder-decoder model 210 based on the comparison between the training reconstructed image and the reconstructed image generated by the model applier 216. Using the error measure determined by the error calculator 224, the model corrector 226 may update the encoder-decoder model 210. In some embodiments, the model corrector 226 may modify or update the encoder 218 and/or the decoder 220 using the error measure. In some embodiments, the model corrector 226 may apply the error measure to the convolution stacks 232A-N of the encoder 218, including the filters 240A-N, the convolutional layer 234A-N, the normalization layers 236A-N, and/or the activation layers 238A-N. In some embodiments, the model corrector 226 may modify, adjust, or set the one or more parameters of the filters 240A-N of each convolutional layer 234A-N based on the error measure. In some embodiments, the model corrector 226 may increase or decrease the one or more parameters of the filters 240A-N of each convolutional layer 234A-N based on whether the error measure is positive or negative. In some embodiments, the model corrector 226 may modify, adjust, or set the size of the filters 240A-N of each convolutional layer 234A-N based on the error measure. In some embodiments, the model corrector 226 may apply the error measure to the convolution stacks 244A-N of the decoder 220, including the filters 254A-N, the convolutional layer 248A-N, the normalization layers 250A-N, and/or the activation layers 252A-N. In some embodiments, the model corrector 226 may modify, adjust, or set the one or more parameters of the filters 254A-N of each convolutional layer 248A-N based on the error measure. In some embodiments, the model corrector 226 may increase or decrease the one or more parameters of the filters 254A-N of each convolutional layer 248A-N based on whether the error measure is positive or negative. In some embodiments, the model corrector 226 may modify, adjust, or set the size of the filters 254A-N of each convolutional layer 248A-N based on the error measure.

By repeatedly comparing training reconstructed images with the model reconstructed images 256, the model trainer 212 may update the encoder-decoder model 210 until the model reconstructed images 256 significantly match the training reconstructed images (e.g., within 10%). In some embodiments, the model corrector 226 may determine whether the encoder-decoder model 210 has reached convergence. In some embodiments, the model corrector 226 may compare the encoder-decoder model 210 prior to the update with the encoder-decoder model 210 of the update. In some embodiments, the model corrector 226 may compare the one or more parameters of the filters 240A-N or 254A-N prior to the update with the one or more parameters of the filters 240A-N or 254A-N. In some embodiments, the model corrector 226 may calculate a difference between the one or more parameters of the filters 240A-N or 254A-N prior to the update with the one or more parameters of the filters 240A-N or 254A-N. The model corrector 226 may compare the difference to a predetermined threshold. If the difference is less than the predetermined threshold, the model corrector 226 may determine that the encoder-decoder model 210 has reached convergence, and may terminate the training mode for the encoder-decoder model 210. On the other hand, if the difference is greater than the threshold, the model corrector 226 may determine that the encoder-decoder model 210 has not yet reached convergence. The model corrector 226 may further continue to train the encoder-decoder model 210 using the training data 228.

Figure 2E:
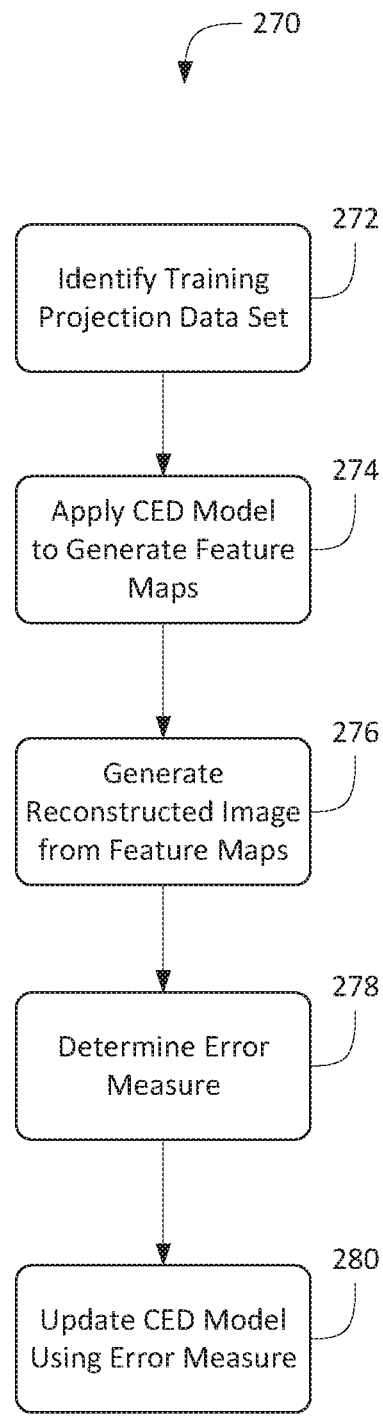
FIG. 2E depicts a flow diagram of a method of training convolutional encoder-decoder (CED) models for reconstructing biomedical images.

Referring to FIG. 2E, depicted is a method 270 for training CED models for reconstructing images. The functionalities of the method 270 may be implemented or performed using the schema 100 as detailed in conjunction with FIG. 1, by the system 200 as detailed herein in conjunction with FIGS. 2A-2C, or the computing system 1600 described below in conjunction with FIG. 16A-D. In brief overview, an image reconstructor may identify a training projection dataset (272). The image reconstructor may apply a convolution encoder-decoder (CED) model to the training projection dataset to generate feature maps (274). The image reconstructor may generate a reconstructed image from the feature maps (276). The image reconstructor may determine an error measure between the reconstructed image and a training image (278). The image reconstructor may update the CED model using the error measure (280).

In further detail, the image reconstructor may identify a training projection dataset (272). The image reconstructor may retrieve the projection dataset from a training database. The projection dataset may include one or more data counts. The one or more data counts may correspond to a cross-sectional area or a volume of a subject, including the internal anatomical and physiological structure of the subject. The one or more data counts may be of a predefined size. The image reconstructor may modify the number of data counts in the projection dataset. In some embodiments, the image reconstructor may up-sample or down-sample the projection dataset to modify the number of data counts.

The image reconstructor may apply a convolution encoder-decoder (CED) model to the projection dataset to generate feature maps (274). The CED model may include an encoder and a decoder. The encoder may contract the size of the projection data to generate a set of feature maps. The encoder may include a set of convolutional stacks. Each convolutional stack may include one or more convolution layers, one or more normalization layers, and one or more activation layers. Each convolution layer may include a predefined number of filters. The number of filters may increase at each successive convolution stack. Each filter may be of a predefined size. The image reconstructor may apply the projection dataset as the input of the CED model. The projection dataset may be successively applied to the set of convolutional stacks to generate a set of feature maps. Each feature map may correspond to one of the filters at the respective convolution layer. Each feature map may be of a predefined size based on the size of the input and the size of the filter. With each successive application of the convolutional stack (including the convolution layer, normalization layer, and the activation layer), the number of feature maps may increase while the size of each individual feature map may decrease.

The image reconstructor may generate a reconstructed image from the feature maps (276). The image reconstructor may continue to process the projection dataset through the decoder of the CED model. The decoder may use the projection dataset to generate the reconstructed image. The decoder may also include a set of convolutional stacks. Each convolutional stack may include one or more upsampling layers, one or more convolution layers, one or more normalization layers, and one or more activation layers. Each upsampling layer may increase the size of the feature map by zero-padding and applying an interpolation filter. Each convolution layer may include a predefined number of filters. The number of filters may decrease at each successive convolution layer. Each filter may be of a predefined size. The set of feature maps outputted by the encoder may be applied to the decoder. The output of one convolution stack at the decoder may successively be applied to next convolution stack of the decoder. Each feature map may correspond to one of the filters at the respective convolution layer. Each feature map may be of a predefined size based on the size of the input and the size of the filter. With each successive application of the convolutional stack (including the upsampling layer, the convolution layer, normalization layer, and the activation layer), the number of feature maps may decrease while the size of each individual feature map may increase. Using the one or more feature maps generated by the last convolution stack of the decoder, the image reconstructor may generate the reconstructed image.

The image reconstructor may determine an error measure between the model reconstructed image and a training reconstructed image (278). The model reconstructed image may be generated from the CED model. The training reconstructed image, on the other hand, may be generated using the training projection dataset and a simulation model. The image reconstructor may calculate a mean square error (MSE) between the training reconstructed image and the model reconstructed image as the error measure. The image reconstructor may also calculate the root mean square error as the error measure as the error measure. The image reconstructor can calculate a pixel-by-pixel difference between the training reconstructed image and the model reconstructed image. Using the differences, the image reconstructor may calculate the error measure.

The image reconstructor may update the CED model using the error measure (280). The image reconstructor may apply the error measure to the encoder of the CED model. The image reconstructor may modify the convolutional layers, the normalization layers, and the activation layers of the encoder. The image reconstructor may change or set the one or more parameters of the filters in the convolutional layers of the encoder in accordance with the error measure. The image reconstructor may modify the convolutional layers, the normalization layers, and the activation layers of the decoder. The image reconstructor may change or set the one or more parameters of the filters in the convolutional layers of the decoder in accordance with the error measure. The image reconstructor may repeatedly update the CED model until the CED model reaches convergence.

6. Results

Figure 3:
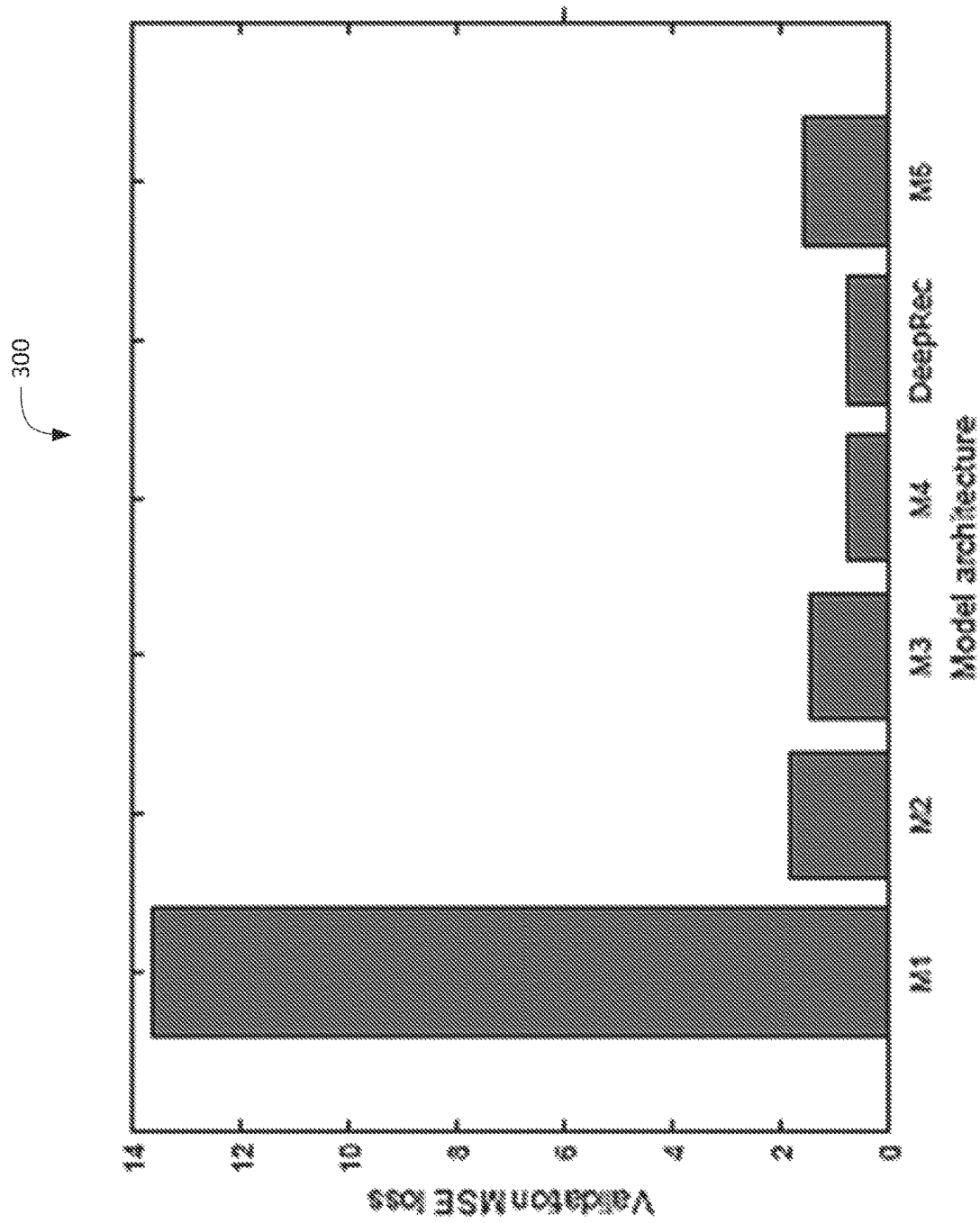
FIG. 3 depicts a graph of a validation loss at epoch 20 for the model design M1 through M6.
Figure 4:
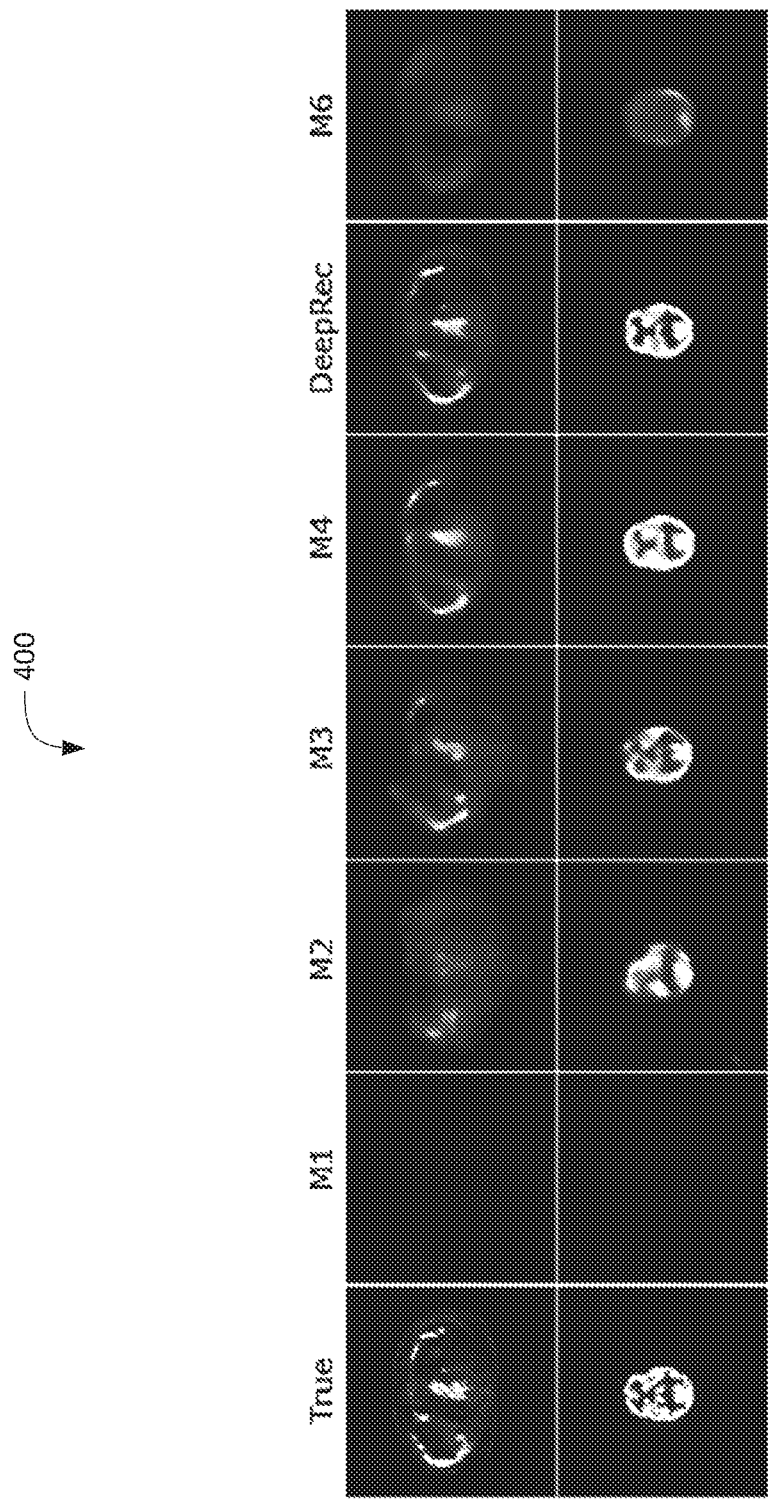
FIG. 4 depicts example reconstructed images using different models M1 through M6.
Figure 5:
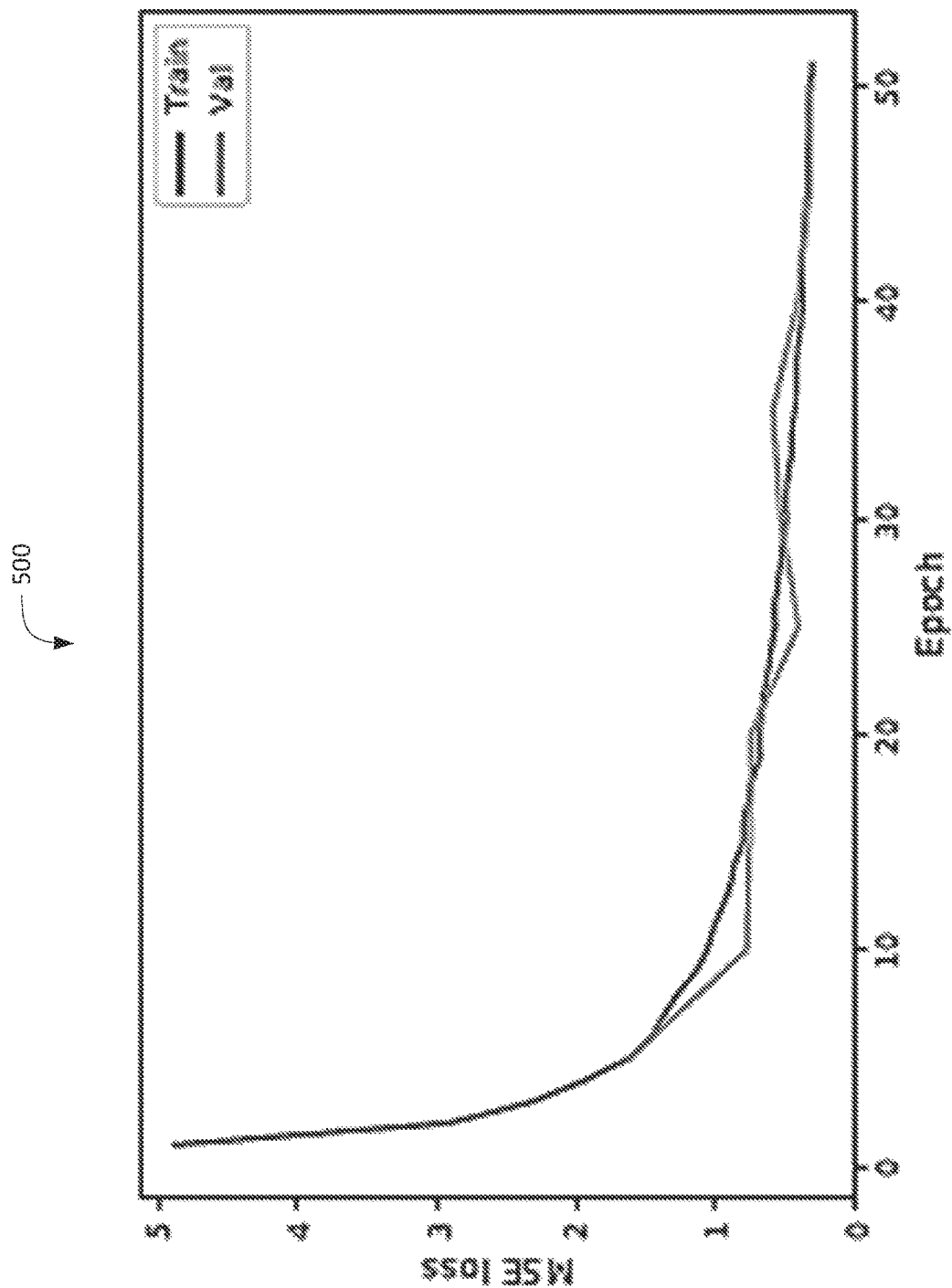
FIG. 5 depicts a graph of the convergence behavior of average MSE calculated between the ground truth simulation and the reconstructed PET images.
Figure 7:
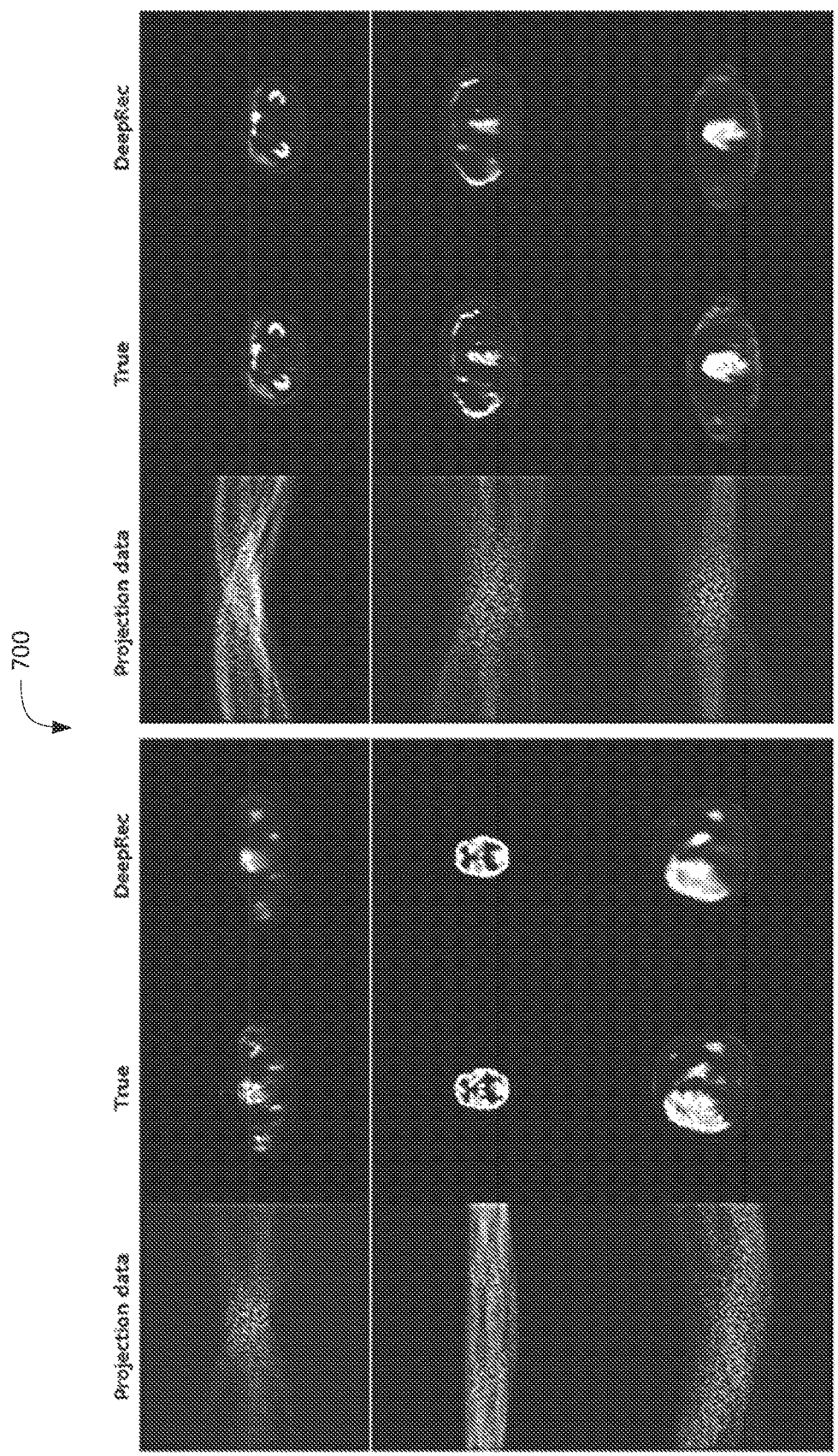
FIG. 7 depicts example reconstructed images from a test set.
Figure 8A:
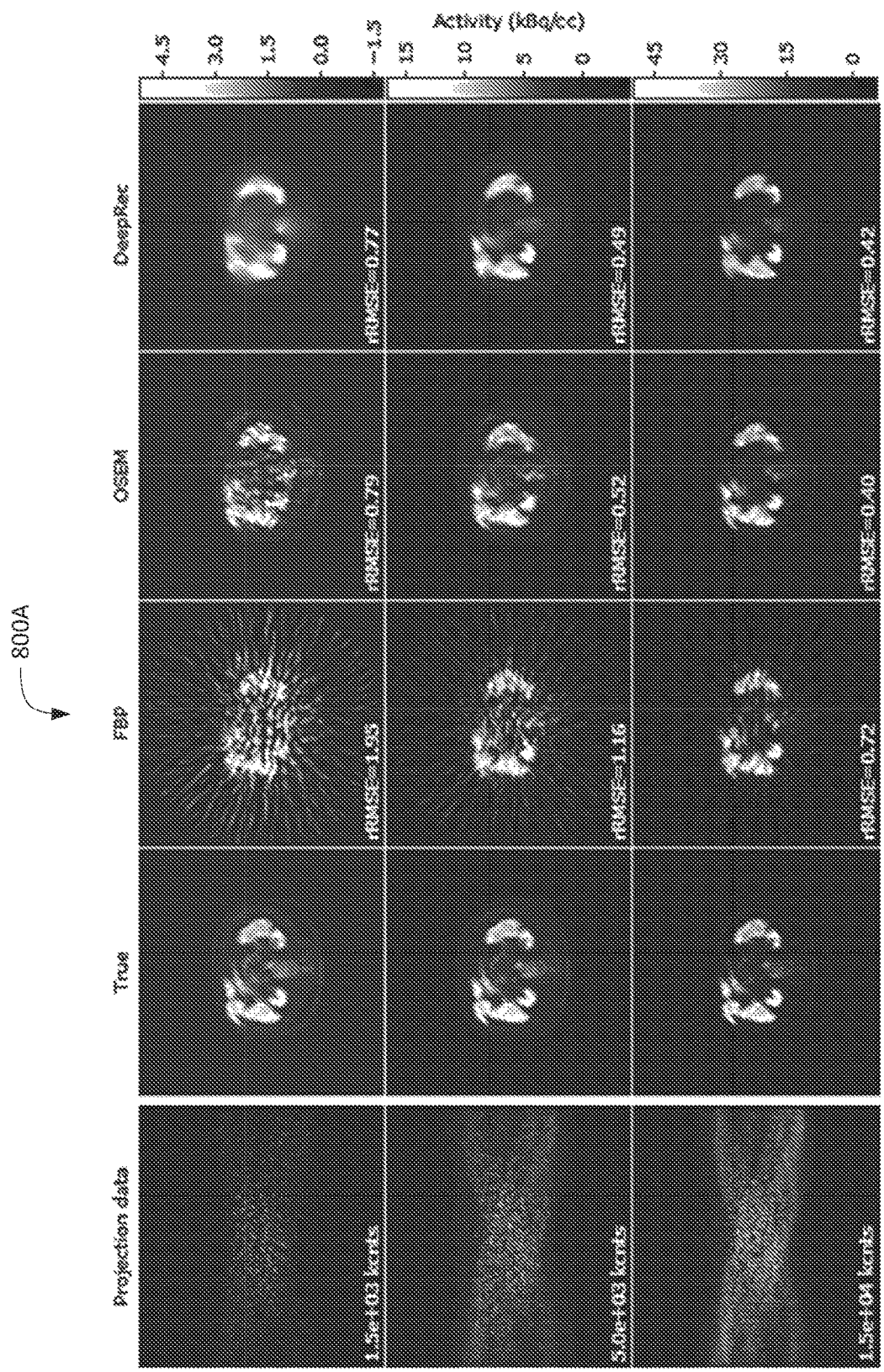
FIGS. 8A and 8B depict example reconstructed images from a test set with different noise levels.
Figure 8B:
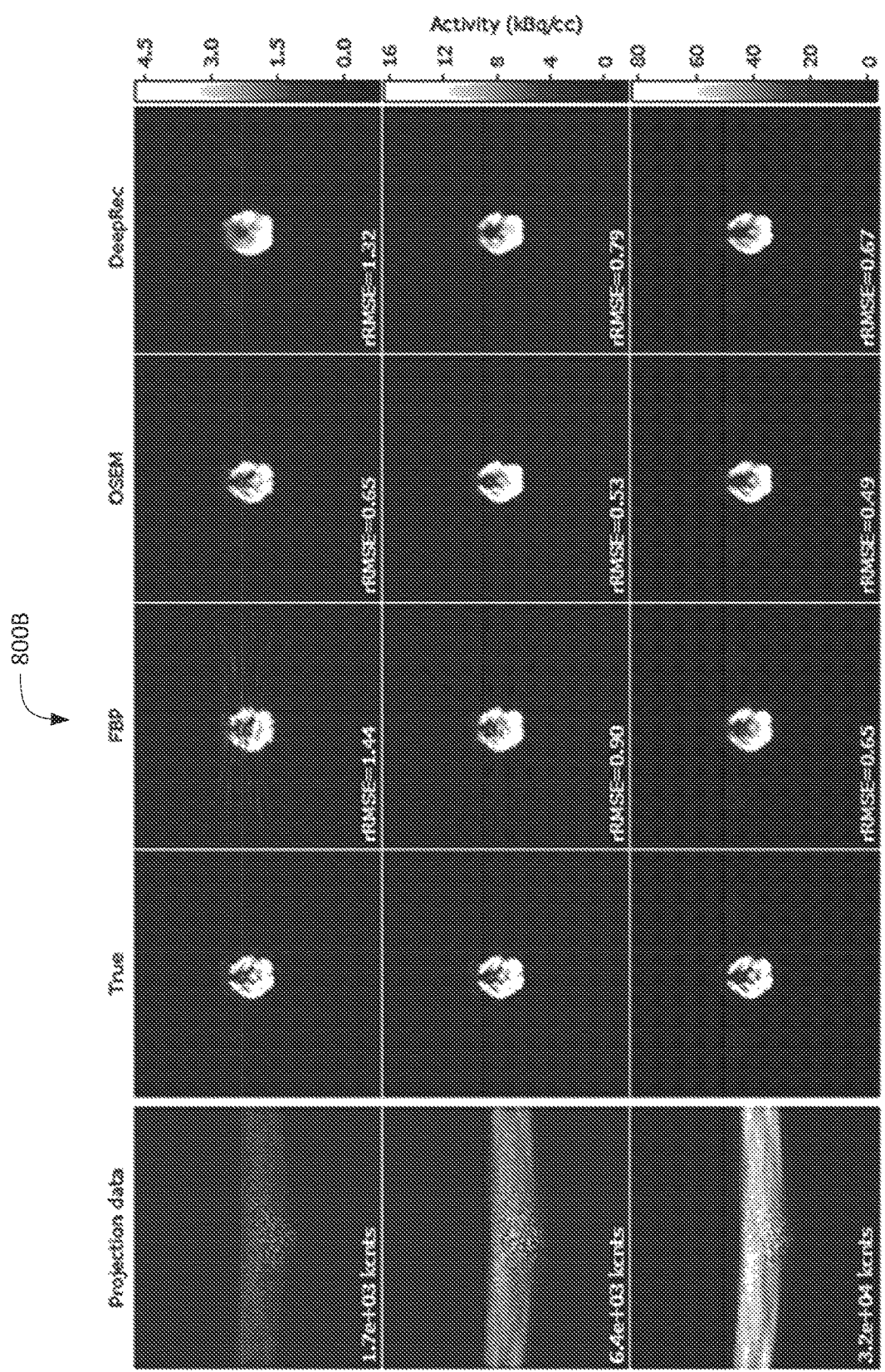

For model designs M1 through M6 as detailed herein in conjunction with FIGS. 1A and 1B, the validation set MSE loss at epoch 20 is seen in graph 300 of FIG. 3, and two reconstructed test set images 400 for the different designs is seen in FIG. 4. The Adam optimizer was found to yield poorer results compared to SGD. Resulting images lacked detail and were much blurrier. Using SGD, smaller image structures were able to be captured and the losses were reduced. Even though some designs yielded a rather small validation loss, images were too blurry. As such, model 5 was selected and is referred to herein as DeepRec. FIG. 5 shows a graph 500 of the average loss of the training and validation sets as a function of training epoch. As can be seen, the loss decreases as a result of the network learning to better represent the data features. The average reconstruction time per image in the test set, together with the average rRMSE using FBP, OSEM and DeepRec are found in a graph 600 of FIG. 6, and example of successful reconstructions from the test set are seen in images 700 of FIG. 7. FIGS. 8A and 8B also include FBP and OSEM reconstructions (800A and 800B respectively), and shows results for different input data noise levels.

Figure 9:
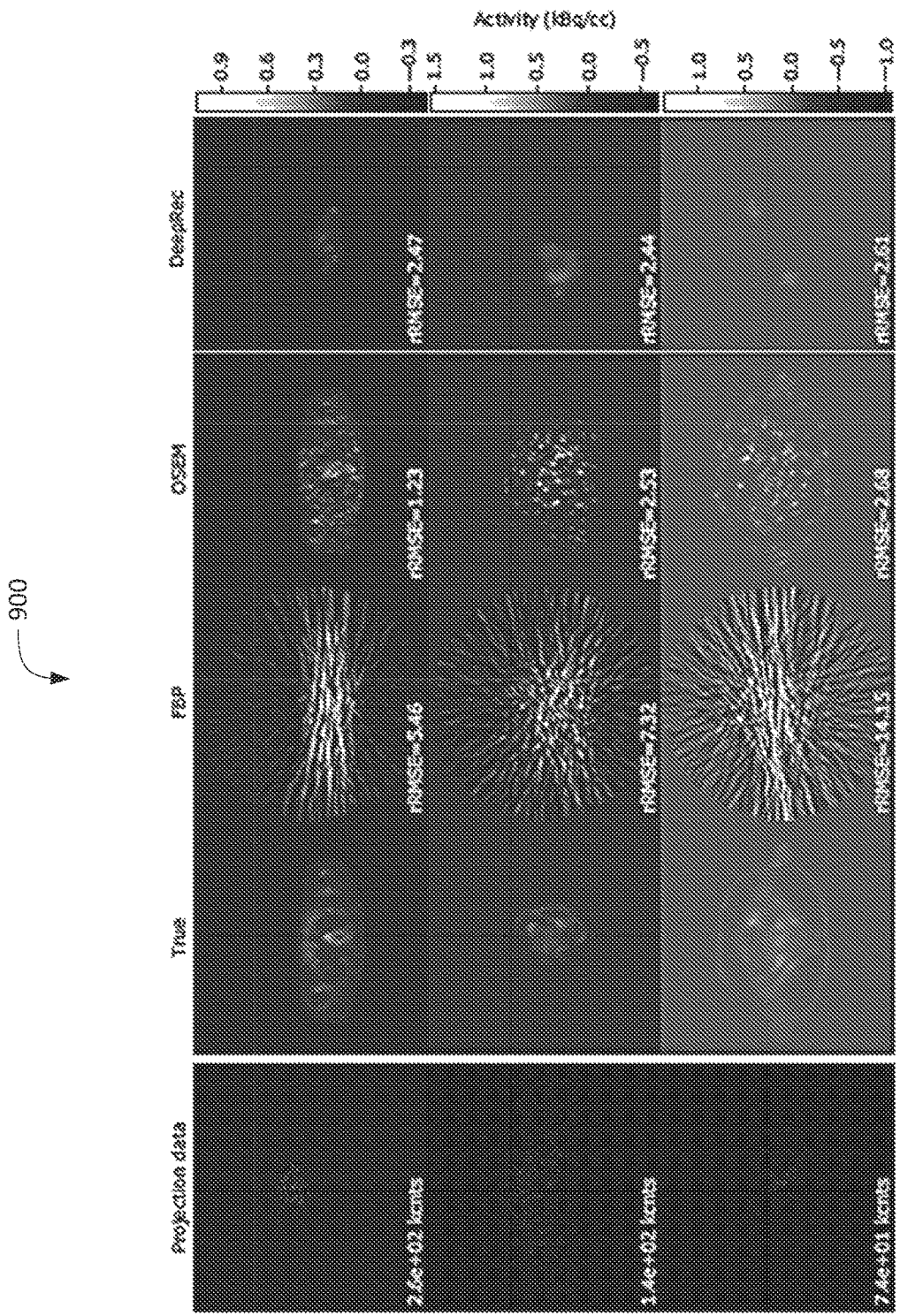
FIG. 9 depicts example reconstructed images from a test set with low input data counts.

With an average execution speed of 25 ms per image, DeepRec compares favorably to the state-of-the-art methods of FBP at 55 ms and OSEM at 425 ms. DeepRec is almost 17 times faster than OSEM. DeepRec also reconstructs the images with the lowest rRMSE of 0.33, compared to FBPs 1.66, and OSEM at 0.69. The DeepRec reconstruction favors a slightly smoother solution compared to OSEM, as evident in FIGS. 8A and 8B, and the overall lower rRMSE. It should be noted that smoother images, whilst preserving detail, is the main goal of regularizers used in iterative PET reconstruction, as per radiologist preference. As can be seen, DeepRec reconstruction performs worse for lower count input data (higher noise), as can be expected. This is also true for conventional reconstruction techniques. It was seen however, that for very low counts, DeepRec would at times generate very weak images, or even occasionally empty images. Conventional techniques, albeit very poor visual and quantitative quality, typically still manage to reconstruct the gross structure. Examples of poor DeepRec reconstructions 900 can be seen in FIG. 9, where true structure is lost and the result is mostly single or a few blobs. This kind of behavior is however seen in data of lower count than generally found in the clinic (on the order of 10 kcnts). It is believed that this effect to contribute to the relatively large spread in rRMSE as seen in FIG. 5.

7. Discussion

One major benefit with PET over many other modalities is that it is inherently quantitative. Hence, the network input and output, though differing in size and structure (as they come from different data domains: projection data vs. images), are related to one another, where pixel units go from projection data counts (registered photon pairs) on the input side, to image pixels in Bq/mL as output. Furthermore, due to the quantitative nature of the data, normalization of the input data was not performed, since the scaling of the input should decide the output scaling. In addition, the spatial correlation between neighboring bins (pixels) in the projection data is not the same as that in the reconstructed image. The use of a convolutional encoder is therefore not as straight forward and intuitive as when working with ordinary image input. Due to memory, time, and overfitting limitations, a fully connected network on the other hand is not feasible for large 2D data due to the huge number of network weights. As an example, a single fully connected layer taking one projection of 288×381 to a 128×128 image requires almost 2 billion weights.

Figure 6:
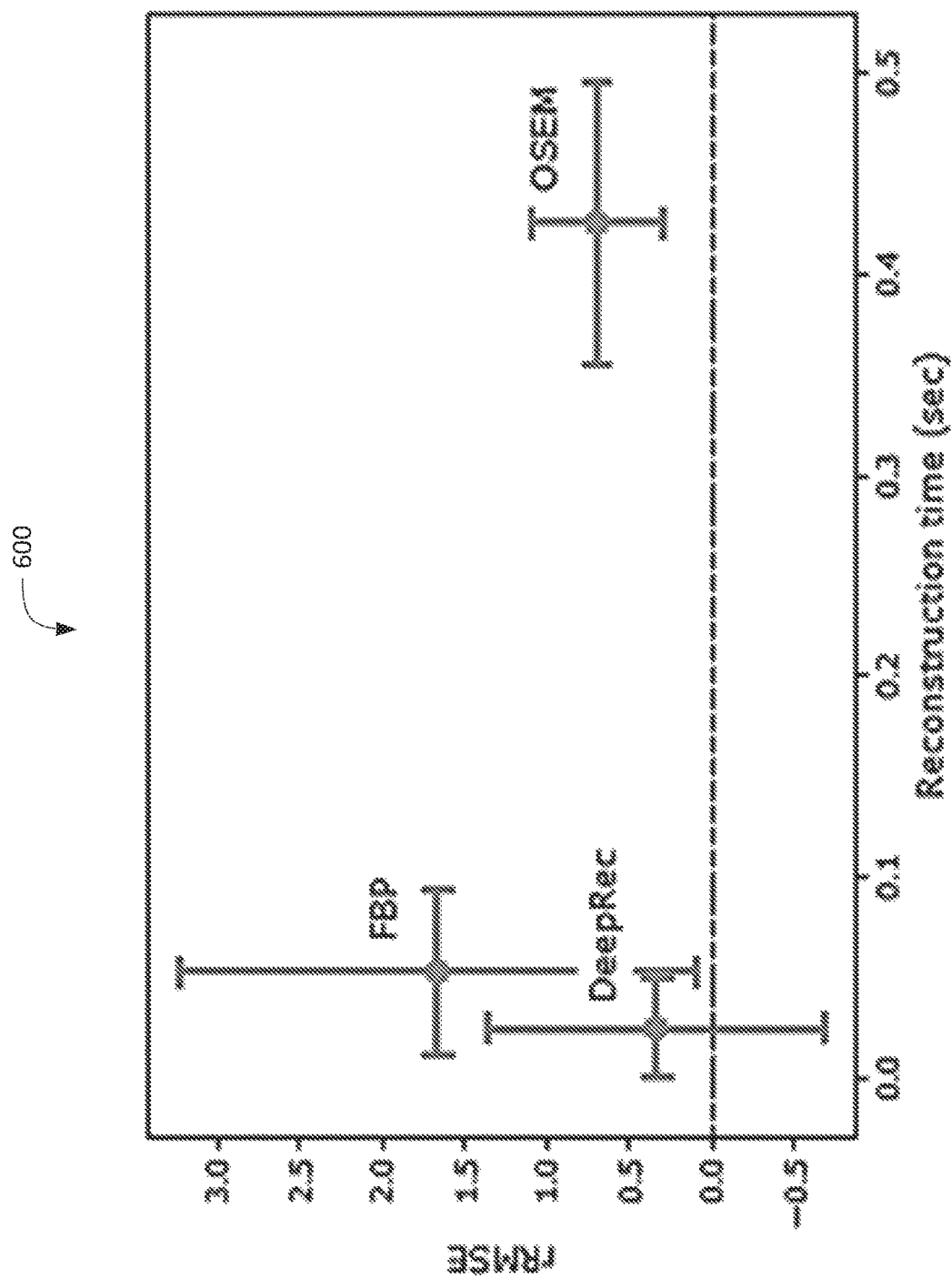
FIG. 6 depicts a graph of average reconstruction time (single image) and average rRMSE in the test set for the different reconstruction methods.

As shown in the results, DeepRec was almost 17 times faster than standard OSEM and faster than FBP (as depicted in FIG. 6), where DeepRec only requires one pass to reconstruct an image from projection data, whereas traditional techniques require multiple iterations. This would be even more pronounced with regularized reconstruction due to the larger number of iteration typically used. It should be noted that the time savings of DeepRec versus iterative will likely grow larger with the increased use of regularizers.

The deep PET reconstruction method described herein can be extended to 3D by substituting the 2D convolutions and up-sampling steps in the model by their 3D versions. It should be noted that this largely increases the complexity of the network, as well as the time and computer memory needed for training. Furthermore, although the present disclosure focuses on PET, the methodology presented is also valid for other types of tomographic data, CT being the most relevant example. CT data is much less noisy than PET, and has higher spatial resolution, making it a very suitable candidate for the approach presented here.

One next step is to include regularizers within the loss function for training. Although any effects of overfitting have not been seen at this point, network weight sparsity could be enforced as one example.

8. Simulated Data Versus Real Data

Referring to FIG. 1A, using simulated as opposed to real clinical data was the chosen methodology since it allowed access to ground truth images. Simulated images are based on simplifications and assumptions of the underlying processes, the risk being that the trained network will learn those properties (e.g. approximate randoms as a uniform count over the projection data) instead of real ones. The more accurate the simulation method is, the lower the risk. Monte Carlo simulations can provide a more accurate representation of the projection data, but due to the need of huge datasets (>100,000), it is challenging to achieve them within a reasonable time as such simulations typically take days, weeks or even months per image. Instead, in some embodiments of the present disclosure, the methods and systems relied on PETSTEP, which has been validated against Monte Carlo methods and have been proven to give realistic results indicating that the methodology still holds and is valid for model comparison.

Since already reconstructed clinical OSEM images were used as ground truth input to PETSTEP, the reconstructed clinical OSEM images were inherently noisy with lower resolution already prior to PET acquisition simulation. The CED network can be configured to learn based on features included in the training dataset, and hence it is likely that using sharper ground truth images in turn would yield a network better able to produce sharp images.

The present disclosure does not include comparisons to any regularized iterative technique, only analytical FBP and unregularized OSEM. This highlights one of the main drawbacks with those approaches. Since there are no general automatic penalty weight selection schemes, it is very difficult to reconstruct on the order of 100,000 images of different anatomies and vastly varying noise levels without user oversight and input. This is the main reason for not including such reconstructions.

Root mean squared error (RMSE) was chosen as a final metric to compare reconstructed images to ground truth. Although this is one of the most commonly used image quality metrics, RMSE has limitations. It is generally beneficial for smoother images, even if some detail is lost. Although not described in this present disclosure, other metrics could be useful to evaluate resulting image quality.

As described herein, the methods and systems described herein utilize a deep learning model that is capable of directly reconstructing PET images from projection data. The present disclosure describes a novel encoder-decoder architecture for PET projection data that utilizes a deep learning model that reduces the reconstruction error over the conventional (OSEM=0.69) by more than 50% while being 17 times faster. Ultimately the gain in quality and speed should lead to faster diagnoses and treatment decisions and thus to better care for cancer patients.

B. Systems and Methods of Applying Reconstructing Biomedical Images

Positron emission tomography (PET) is widely used for numerous clinical, research, and industrial applications, due to its ability to image functional and biological processes in vivo. PET can detect radiotracer concentrations as low as picomolar. In cancer care, this extreme sensitivity enables earlier and more precise diagnosis and staging, which is greatly correlated with early treatment intervention and better patient outcome. The benefits of PET rely strongly on quantitative PET images, and involve a reliable method that produces high image quality.

Tomographic PET projection data (sinograms) cannot be directly interpreted by an observer, but are first be reconstructed into images. However, random process noise in the data makes this relationship ill-posed, and the reconstruction of the tracer's distribution function can be solved as an inverse problem. Various PET reconstruction techniques exist, the most common being analytical filtered back-projection (FBP), and iterative maximum-likelihood (ML) methods. The latter includes maximum-likelihood expectation maximization (MLEM) or its incremental update version, ordered subset expectation maximization (OSEM). Typically, however, images resulting from these standard methods suffer from data/model mismatches, data inconsistency, and data over-fitting, which can manifest as artifacts such as streaks and noise in the reconstructed images. In the case of ML methods, regularization can be used to overcome the ill-posedness and reduce the fitting noise in the final images. However, regularization for PET image construction may involve many iterations to make its benefits apparent. As a result, methods have only recently been implemented clinically. Regularization is still an open problem in PET image reconstruction, and many approaches have been proposed. However, there is no clear consensus on how to choose between these approaches, or automate the regularization strength.

The use of a deep network carries some advantages, because it can be trained to at once learn the inverse of the physical model, the appropriate statistical model, and the regularization that best fits the character of the noisy data. Another advantage is its potential for computational efficiency. Viewing the deep network as a regularized inverse to the PET system model, one can envision it as performing a single forward step, as opposed to iteratively back- and forward-projecting the data numerous times (e.g., gradient descent). Hence, the present disclosure provides an encoder-decoder network that uses supervised learning to solve the PET reconstruction inverse problem directly.

Deep learning has many applications, such as medical image restoration, segmentation, and analysis, among others. In particular, encoder-decoder architectures, such as convolutional encoder-decoder (CED) models, can stepwise compressing the input image data into a latent space representation, and then stepwise rebuilding that representation into a full dataset. CEDs and generative adversarial networks have been used to restore low dose computed tomography (CT) images, estimate full view from sparse view FBP images, and reduce metal artifacts in CT. Furthermore, neural networks may generate synthetic CT from magnetic resonance (MR) images, improve maximum a posteriori (MAP) PET reconstructions, and improve dynamic PET MLEM reconstructions.

But it is less explored how to use deep learning methods within the PET image reconstruction process itself, i.e., as part of generating PET images directly from PET sinogram data. One approach may involve convolutional neural networks (CNNs) to optimize the regularizing term in iterative CT reconstruction. Although the CNN is part of the reconstruction loop, this approach still relied on regularized iterative approaches. Also using the concept of iterative CNN reconstruction, another approach may employ a residual convolutional autoencoder within an ML framework to denoise PET images, and use CNN for regularization in MR reconstruction. Another approach may involve deep enforcement learning for parameter tuning in iterative CT reconstruction. An end-to-end approach, may employ image reconstruction for various medical imaging modalities by deep learning the transform between sensor and image domain. However, this approach focused on MR, providing only a single low resolution example for PET data without testing or analysis. Another approach may involve an iterative end-to-end trained CNN, applied to CT image reconstruction, in which the primal and dual proximal updates can be learned using the primal dual hybrid gradient algorithm. Another approach may entail an iterative end-to-end approach for CT, in which a CNN can project the gradient descent of a chosen objective function into the space of the underlying object (i.e., the universe of all CT images). In both cases, such approaches may utilize a known system model within an iterative scheme. In particular, a noise model may be explicitly defined for the learning algorithm.

The present disclosure provides a deep CED architecture (also referred herein as DeepPET), which directly and quickly reconstructs PET sinogram data into high quality, quantitative images. The is the first systematic, full-scale, end-to-end work for PET in the new field of direct deep learning-based tomographic image reconstruction.

1. Emission Computed Tomography Image Reconstruction

Emission computed tomography image reconstruction is based on a Poisson noise model given by:

$$g = \text{Poisson}\{Af+\gamma\}, \quad (1)$$

where g is the measured sinogram data, A is the linear projection operator, $f$ is the unknown activity distribution (image) to be estimated, and $\gamma$ is the additive counts from random and scatter events. This model can be solved by minimizing the residual of the Kullback-Leibler (KL) divergence of the data model and a regularization term, which results in the minimization problem given by $$f = \arg f \min\{[Af,1] - [\log Af+\gamma, g] + \lambda R(f)\}, \quad (2)$$

where [·,·] is the inner product, $R(f)$ is a regularization function, and $\lambda$ the regularization weight. In this form, the physical aspects of the model (e.g., geometry and statistical distribution) are accounted for by the KL-divergence term. However, the model in (2) contains many assumptions. These include the approximation of the geometric relationship between the image and detectors, the associated point spread function, the estimate of the additive count distribution, the validity of the Poisson statistical model as applied to the actual data, and the functional form of the regularizer. In particular, the optimal regularization function R is not generally known, nor is the regularization weight $\lambda$.

On the other hand, a deep neural network has the potential to learn each of these aspects of the model from the data itself. The network learns the correct geometric, statistical, and regularization models, provided that the training examples are sufficiently realistic. As a result, knowledge of all these properties do not need to be explicitly included in the network model. Simulated PET data may be used for network training, which also relies on assumptions such as the Poisson noise and forward models to generate synthetic data.

Precorrected data may be used, where the i-th precorrected data element is given by:

$$\hat{g}i = \frac{(g_i - \gamma_i)}{\mu_i} \quad (3)$$

where $\mu i$ is the attenuation in the i-th coincidence count. Precorrecting the data mixes its statistical properties and, as a result, is generally avoided in the inverse problem formulation due to its explicit use of a particular statistical model (Poisson in the case of PET). However, the solution is not explicitly dependent on any a priori data noise model making precorrection applicable. Alternatively, additional network inputs (attenuation map and scatter+randoms estimate) can be used. However, using precorrected data instead decreases the network size, and thus memory usage and computation time, as well as reduces the risk of overfitting.

The precorrected data includes the generation of 2D humanoid phantom images, followed by simulation of realistic PET scans with PETSTEP, resulting in multiple sinogram datasets at different noise levels. Experimental setup of the network training procedure is shown on the bottom, where the sinogram data is first precorrected for scatters, randoms and attenuation, and cropped before being inputted to DeepPET. Details of the DeepPET architecture is shown on the bottom middle.

2. Modeling Noise in Computed Tomography Image Reconstruction

The mathematical model of the both PET and SPECT systems are identical and therefore these methods apply to both equally, is described by:

$$g = \{Af+\gamma\}_{noise} \quad (4)$$

where g is the projection data, $f$ is the tracer distribution function (image), A is the system matrix/operator (the function that describes the relationship between the probability that a voxel/point in $f$ will contribute to the data g), $\gamma$ is the additive counts/noise from scatter, random and cascade coincidences, and $\{\cdot\}_{noise}$ refers to the nonlinear process of random noise, usually Poisson distributed but not necessarily. This model is used in image reconstruction where given g, A, and $\gamma$, an estimate $f$ is sought.

Because of random noise this problem is ill-posed (either over- or under-determined), making the estimation off difficult. The estimation off is usually performed by minimizing modeling error in the following form known as the forward model:

$$\min_{f \geq 0}\{F(f, g, A, \gamma) + \lambda R(f)\} \quad (5)$$

where $F(f, g, A, \gamma)$ represents the data model fidelity term (typically, negative log-likelihood), and $\Delta R(f)$ is a regularization function and its weighting term (scalar or matrix).

There may be several difficulties in the estimation of $f$. First, since for 3D time-of-flight (TOF) data both g and $f$ are large the system A is very large, which as a result cannot be explicitly stored. For example, for a GE D710 PET/CT with 381×576×288×50=6.2E+9 data elements and 256×256×47=3.1E6 image voxels, there are approximately 1E16 elements in the system matrix, A. Because this matrix has some structure and is sparse it can be computed on the fly, but the calculation although tractable may be very slow. Second, the noise distribution is generally assumed to be Poisson; however, it is unknown. Since the noise distribution is Poisson no closed form solution exists, and each iteration at a minimum requires the A operator and its adjoint to be used each iteration. This leads to very slow reconstruction times requiring multiple iterations. Third, the optimal regularizer and its weight term are unknown and remains an open problem. An accurate estimation of $\gamma$ depends on $f$ and is therefore its estimated accuracy is limited.

To address these challenges in estimating, an encoder-decoder network may be used to reconstruct images of the tracer distribution function, where the projection data is input, and the images are the output. Using this network model, the network learns the inverse of the forward model. The noise model may be learned rather than imposed. The regularization model may be also learned rather than imposed. If trained using real labeled data (not simulated), the model may learn the true forward model. One pass through the network is very fast on the order of a single system operator operation.

These features may be demonstrated in 2D simulations by preprocessing the data to create a compact input data structure:

$$g_{pre} = = A_\mu^{-1}(g-\gamma) = A_{geo}f \qquad (6)$$

where $A = A_\mu A_{geo}$, are separable into scan specific (e.g., deadtime, normalization, and attenuation) and fixed geometric components. The noise distribution of $g_{pre}$ may be initially unknown and not Poisson. In conventional PET/SPECT, such modeling is not done because the noise distribution is not known and the use of either Poisson or normally distributed data modes produce inferior images.

Preprocessing of projection data may be done to allow efficient 3D TOF image reconstruction, because the size of the projection data the method described above is not suitable for GPUs for training the deep learning models. By preprocessing the projection data via exact Fourier or exact TOF-Fourier rebinning, the oblique data planes can be removed with little to no loss of information. This effectively reduces the size of the input data by a factor of 500 in the case of exact TOF-Fourier rebinning, making network training and use on a GPU tractable. The model given by rebinning may be described by:

$$g_{3D\text{-}TOF,pre} = \text{FORE}_{TOF}(A_\mu^{-1}(g-\gamma)) = \text{FORE}_{TOF}(A_{geo}f) \qquad (7)$$

As iterated above, such modeling may not be done in PET/SPECT reconstruction, because the noise distribution is not known and the use of either Poisson or normally distributed data models produce inferior images. The regularization and system operator may be implicitly learned.

In addition, the 3D TOF projection data may be pre-projected into image space and use an autoencoder network model to deblur and denoise the data. In this case, the model may be formulated as:

$$g_{3D\text{-}TOF,proj} = A_{geo}^\dagger A_\mu^{-1}(g-\gamma) = A_{geo}^\dagger A_{geo}f \qquad (8)$$

where $A_{geo}^\dagger$ is the adjoint of $A_{geo}$. As with the other model, this model may spoil the Poisson-like noise properties but again the network may learn the noise model. Furthermore, the regularization and system operator may be implicitly learned.

3. Dataset Description

The major bottleneck in many deep learning experiments is the limited size of available datasets and lack of labeled data. This problem was circumvented by generating labeled data synthetically. The open-source PET simulation software PET Simulator of Tracers via Emission Projection (PETSTEP) and can be used to simulate PET scans and generate realistic PET data. PETSTEP has previously been validated by the Geant4 Application for Tomographic Emission (GATE) Monte Carlo (MC) software. It includes the effects of scattered and random coincidences, photon attenuation, Poisson counting noise, and image system blurring. A GE D710/690 PET/CT scanner may be modeled, with sinogram data of 288 angular×381 radial bins. This approach is more realistic than only adding Poisson noise to sinogram data, and thus be better enable transferability of the trained network to clinical data.

The deformable humanoid XCAT digital phantom was used to produce random, patient realistic whole-body three-dimensional (3D) phantoms with 280 slices of transaxial size 128×128 pixels over a 700 mm field of view FOV). The generation of one 3D XCAT phantom uses several hundreds of user adjustable parameters regarding the geometry, position (e.g., 3D rotations and translations), patient and organ shape and size, gender, arms up or down, as well as tracer activity of each organ and tissue. Here, these parameters were randomized within realistic ranges to generate a diverse population of 350 patients, making a total of 350.280=98,000 unique two-dimensional (2D) activity images (with associated attenuation μ-maps). Data augmentation was achieved by generating three realizations of each 2D phantom image by randomly right/left flipping, translating (±30 pixels in x and y-dir), and rotating)(±10° the images. Pixels outside a 700 mm circular FOV were set to zero. PET acquisitions of these phantom images were then simulated using PETSTEP, where the activity (noise) level of each image slice was randomized, and the random and scatter fractions were randomly drawn from normal distributions around realistic values for the given activity level and object size. The resulting activity distribution sinograms were then used as the Poisson parameters for generating the random counts. This ensured that the noise used in all simulation data were independently distributed. The simulation resulted in projection datasets containing noisy total, trues, scatters, randoms, and attenuation factors. The data sets with a noisy total count of $<2\cdot10^5$ or $>8\cdot10^6$ were discarded to stay within a clinically relevant count range. 291,010 projection datasets were kept, and the noisy total sinogram data had, on average, $10^6$ total counts. The original 291,010 phantom images were used as ground truth.

Precorrection for scatters, randoms, and attenuation of the simulated total projection data was done according to (3), using the scatter and randoms estimate, and attenuation data from the PETSTEP simulation. Finally, the circular 700 mm FOV leaves the image corners empty, and thereby the first and last 56 radial projection data bins also remain empty. These bins were subsequently cropped (from a total of 381 to 269) to reduce the number of network elements, before using the sinograms as network input.

Figure 10A:
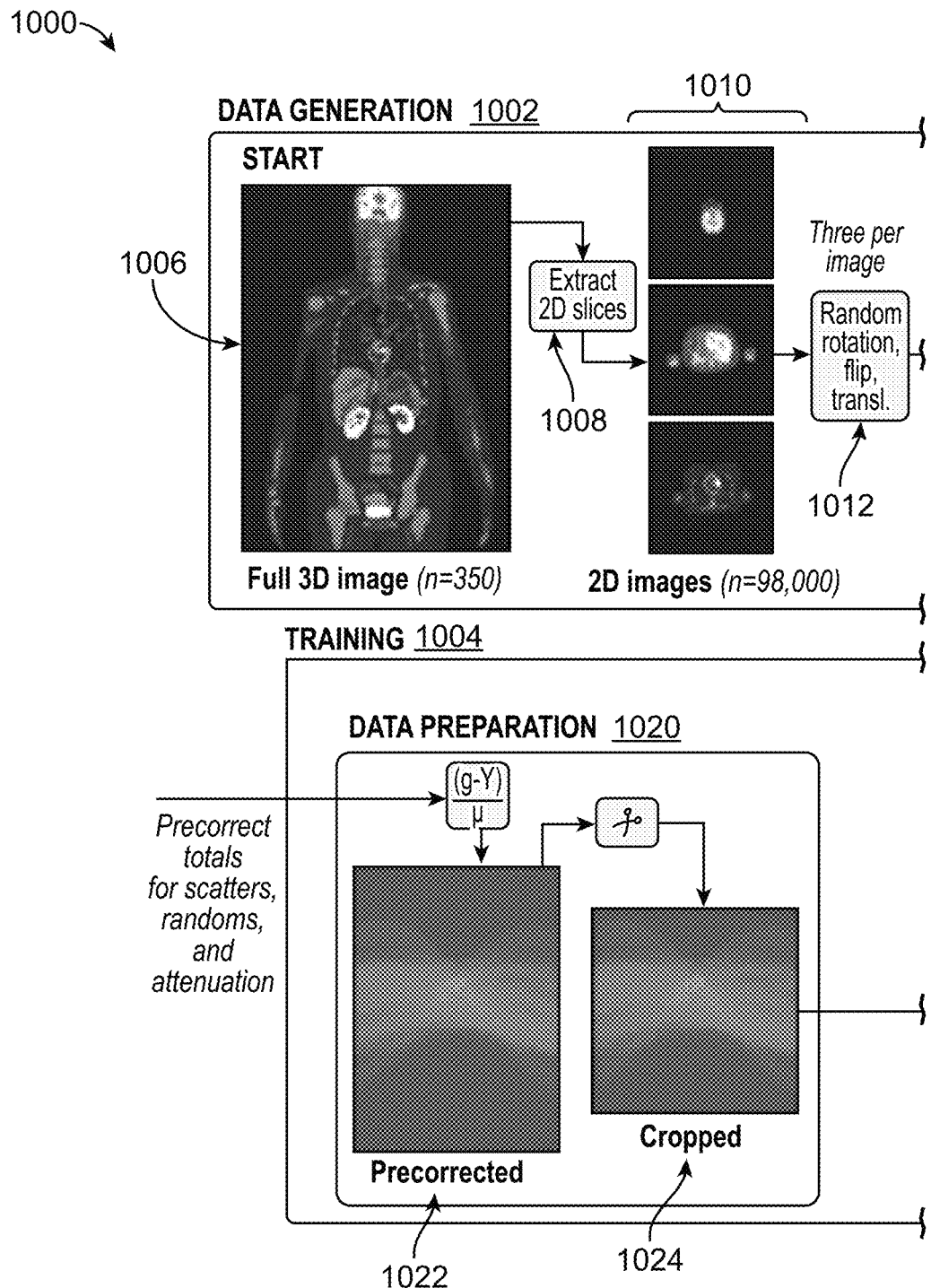
FIG. 10A depicts a schematic of a reconstruction pipeline and the convolutional encoder-decoder (CED) architecture.
Figure 10A:
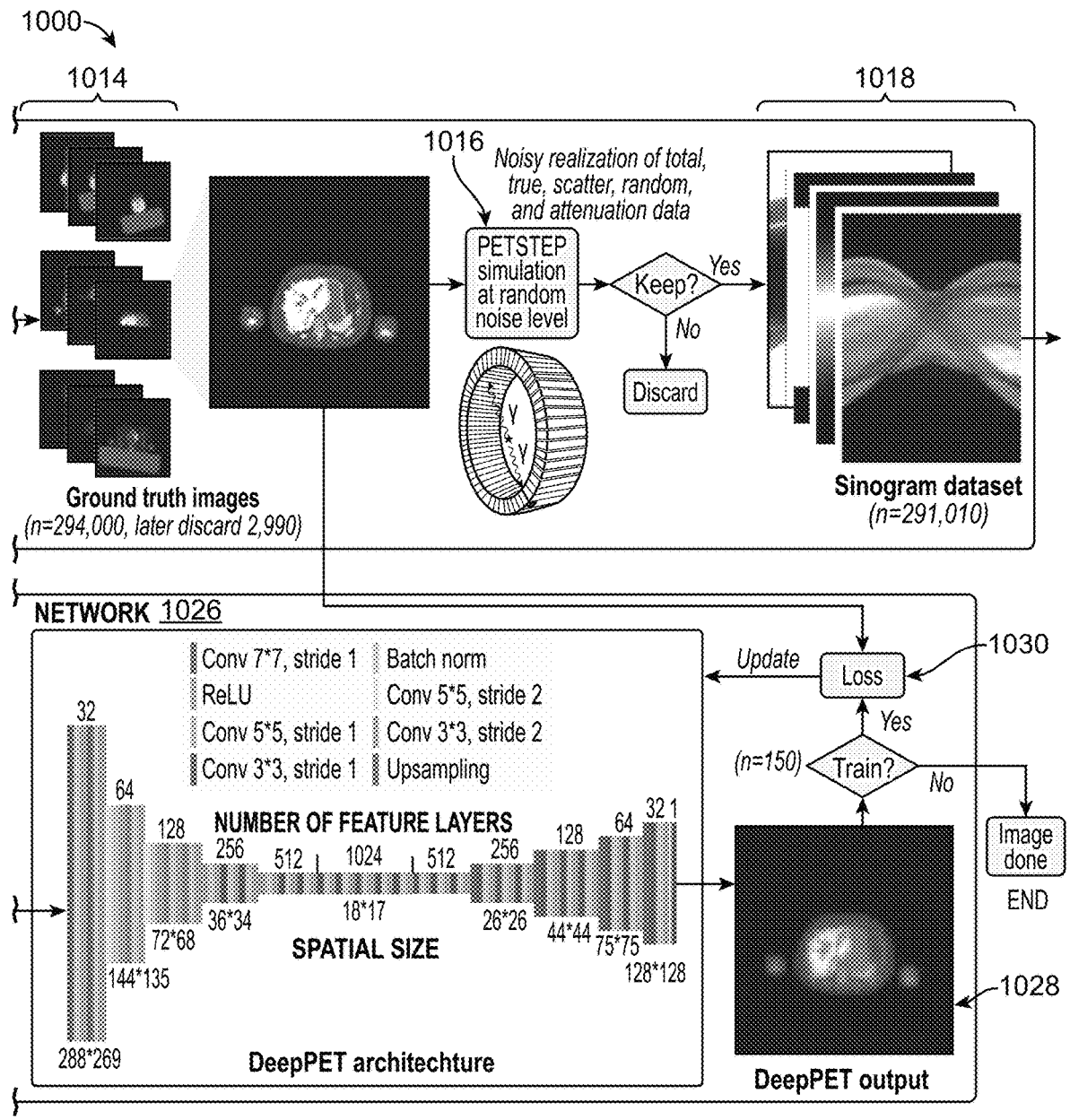

Referring now to FIG. 10A, depicted a schema 1000 of the reconstruction pipeline and the convolutional encoder-decoder (CED) architecture. Schematic illustration of the reconstruction pipeline and the DeepPET convolutional encoder-decoder architecture. The schema 1000 may include a data generation process 1002 and a training process 1004. The schema 1000 detailed herein may include one or more functionalities of the schema 100 detailed above in conjunction with FIGS. 1A and 1B. Each component in the schema 1000 can be implemented using the components detailed herein below in conjunction with FIGS. 16A-D. While the schema 1000 will be described herein in connection with PET, the schema 100 may be used with other modalities of biomedical imaging, such as radiography (e.g., X-rays and fluoroscopy), magnetic resonance imaging (MRI), ultrasonography, tactile imaging (elastography), photoacoustic imaging, functional near-infrared spectroscopy, and nuclear medicine functional imaging (e.g., single-photo emission computed tomography (SPECT)). The data generation process 1002 is depicted on the top half. Experimental setup of the deep learning training procedure 1004 is shown on bottom of the figure.

The data generation process 1002 may start with a full three-dimensional PET scan reconstructed image 1006 from a training dataset. There may be a 350 three-dimensional PET scan reconstructed images from 350 different actual or phantom subjects. From the three-dimensional PET scan reconstructed image 1006, an image slicer 1008 may extract a set of two-dimensional images 1010 by slicing the three-dimensional image 1006 in a select plane (e.g., transverse) at a set stride. For example, the image slicer 10008 may extract 280 two-dimensional slices from the three-dimensional image 1006 to generate the set of 98,000 two-dimensional reconstructed images 1010. To increase the total number of two-dimensional reconstructed images for training, a dataset augmenter 1012 may generate a larger set of two-dimensional reconstructed images 1014 by randomly rotating, flipping, or translating the initial set 1010. This may result in an increase from 98,000 two-dimensional images 1010 to 294,000 set of two-dimensional images 1014, with some of the two-dimension images discarded. The larger set of the two-dimensional PET scan reconstructed images 1014 may serve as the ground truth in training the model.

Using the set of two-dimensional PET scan reconstructed images 1014, an image simulator 1016 may generate one or more simulated PET scans or projection data 1018 (also referred herein as sinograms). The image simulator 1016 can be used to simulate PET scans and generate realistic projection dataset that includes effects of scattered and random coincidences, photon attenuation, counting noise, and image system blurring. In some embodiments, the image simulator 1016 can model a GE D710/690 PET/CT scanner, with projection data of 288 angular×381 radial bins, in generating the projection data 1018. In simulating PET scans for the projection data 1018, the image simulator 1016 can add noise, scattering, random points, and attenuation, among others. In some embodiments, a subset of the projection data 1018 generated via simulation can be discarded based on amount of noise and other factors introduced into the projection data 1018. Once generated, the projection data 1018 can be used in the training process 1004.

Within the training process 1004, the projection data 1018 can be fed into a data preparation process 1020. In the data preparation process 1020, the projection data 1022 may undergo precorrection for randoms, scatters, and attenuation, among other factors in accordance with the formula (3) to generate precorrected projection data 1022. In turn, the precorrected projection data 1022 can be cropped to generate cropped projection data 1022 for input into a network 1026 for addition processing.

4. Encoder-Decoder Architecture

Figure 10B:
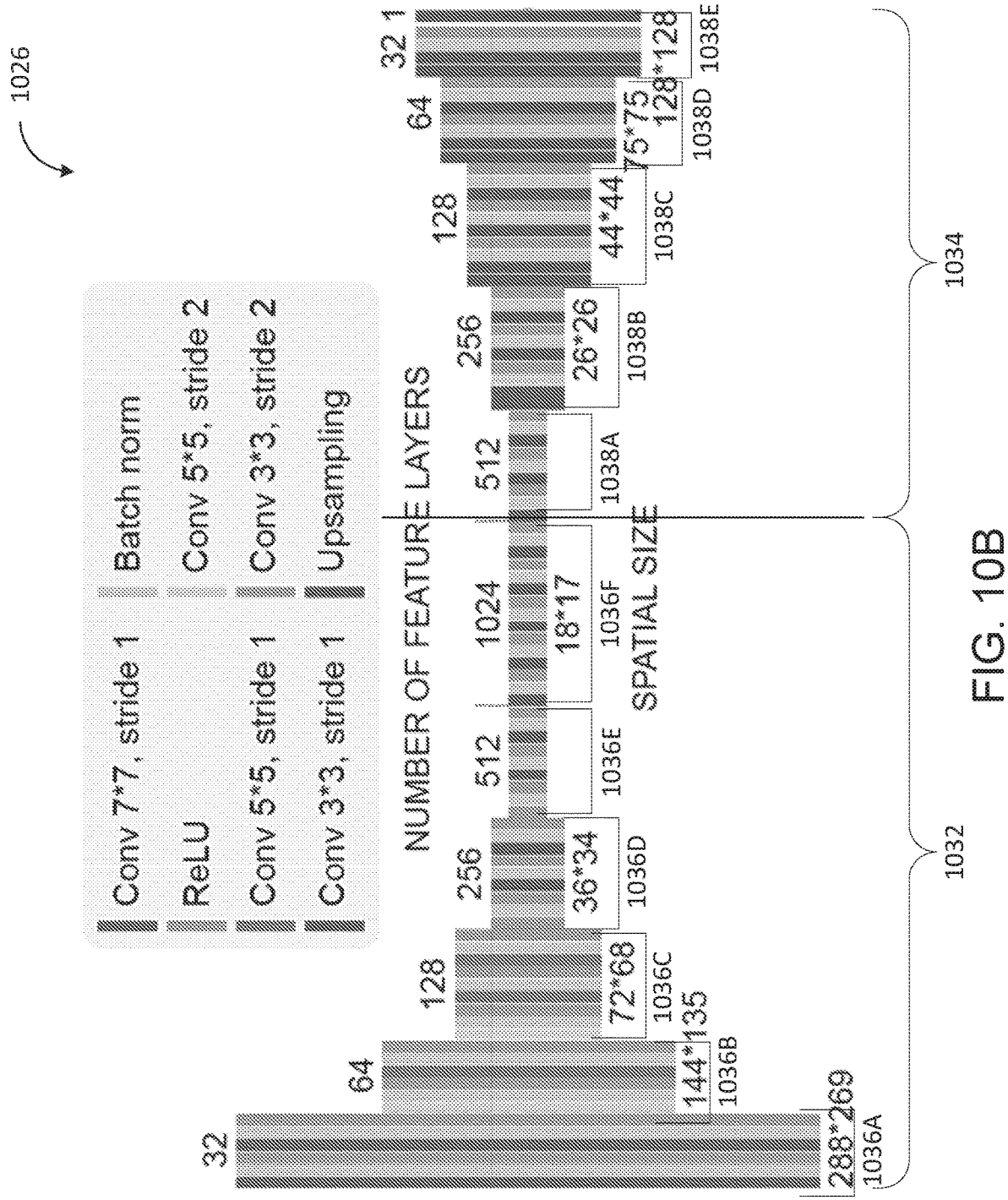
FIG. 10B depicts a schematic of the convolutional encoder-decoder (CED) architecture.

Referring now to FIG. 10B, depicted is a schema of the convolutional encoder-decoder (CED) architecture for the network 1026. The network 1026 may include an encoder 1032 and a decoder 1034. The encoder 1032 may include a series of convolutional neural networks (CNNs) 1036A-F. Each CNN 1036A-F of the encoder 1032 may include one or more convolutional layers, a batch normalization layer, and a rectified linear unit. The decoder 1034 may also include a series of CNNs 1038A-E. Each CNN 1038A-E of the decoder 1034 may include an upsampling layer, one or more convolutional layers, a batch normalization layer, and a rectified linear unit.

The encoder 1032 and decoder 1034 of the network 1026 may loosely mimic the VGG16 network architecture, with modifications, and is depicted in detail in FIG. 10B. The sinogram input data is of size 288×269×1, and the output in image space is of size 128×128×1 The encoder 1032 contracts the input data in a manner typical to CNNs. of the model may include sequential blocks of convolutions with stride 2 and a factor 2 increase in the number of output feature layers, followed by batch normalization (BN) and activation by a rectified linear unit (ReLU). The convolution filter size decreases throughout the encoder, starting with the two first layers of 7×7, followed by 5 layers of 5×5, and the rest are of 3×3. The encoder 1032 output may include 1024 feature maps of size 18×17. Each feature is a non-linear function of an extensive portion of the input sinogram. This is of special interest in this PET scenario because single points in the reconstructed image domain are represented by sinusoidal traces in the input domain In other words, a large spread out portion of the input image data may be used to infer each reconstructed image pixel. This also motivated the initially larger convolution filter sizes of the encoder. The decoder 1034 upsamples the contracted feature representation from the encoder 1032 into PET images. Each step in the decoder 1034 path may include an upsampling layer, increasing the image size by a factor of 1.7, a 3×3 convolution that halves the number of feature layers, a BN layer, followed by a ReLU. The total number of convolutional layers of the whole encoder-decoder network 1026 may be 31.

Several different CED designs for the network 1032 were implemented and explored, with a different number of convolutional layers and feature layer depths, varying spatial sizes and convolution filter sizes, as well as optimization by stochastic gradient descent (SGD) with momentum on mini-batches and learning rate decay, and Adam stochastic gradient descent. The hyperparameters learning rate and mini-batch BN momentum were individually optimized for each architecture, and the models were evaluated by comparing reconstructed image quality on the validation set. The most relevant models/settings investigated are denoted M1 through M8, as well as the ultimately chosen model named DeepPET, and are shown in Table 1.

TABLE 1

Parameterization of the eight most relevant encoder-decoder architectures denoted M1 through M8, in comparison to DeepPET. Hyperparameters (learning rate and batch normalization momentum) were individually optimized. The last column shows the minimum (optimal) validation set mean squared error loss after 150 training epochs.

| Name | Conv layers | Feature layers | Filter size | Optimizer | Val loss |
| --- | --- | --- | --- | --- | --- |
| M1 | 29 | 512 | 3 × 3 | Adam | 0.231 |
| M2 | 29 | 1024 | 3 × 3 | Adam | 0.206 |
| M3 | 31 | 512 | 3 × 3 | SGD | 0.219 |
| M4 | 31 | 512 | 3 × 3 | Adam | 0.202 |
| DeepPET | 31 | 1024 | 7 × 7 | Adam | 0.187 |
| M5 | 31 | 1024 | 3 × 3 | SGD | 0.219 |
| M6 | 31 | 1024 | 3 × 3 | Adam | 0.199 |

TABLE 1-continued

Parameterization of the eight most relevant encoder-decoder architectures denoted M1 through M8, in comparison to DeepPET. Hyperparameters (learning rate and batch normalization momentum) were individually optimized. The last column shows the minimum (optimal) validation set mean squared error loss after 150 training epochs.

| Name | Conv layers | Feature layers | Filter size | Optimizer | Val loss |
|---|---|---|---|---|---|
| M7 | 31 | 2048 | 3 × 3 | SGD | 0.211 |
| M8 | 31 | 2048 | 3 × 3 | Adam | 0.197 |

5. Implementation and Training Procedure

Figure 11:
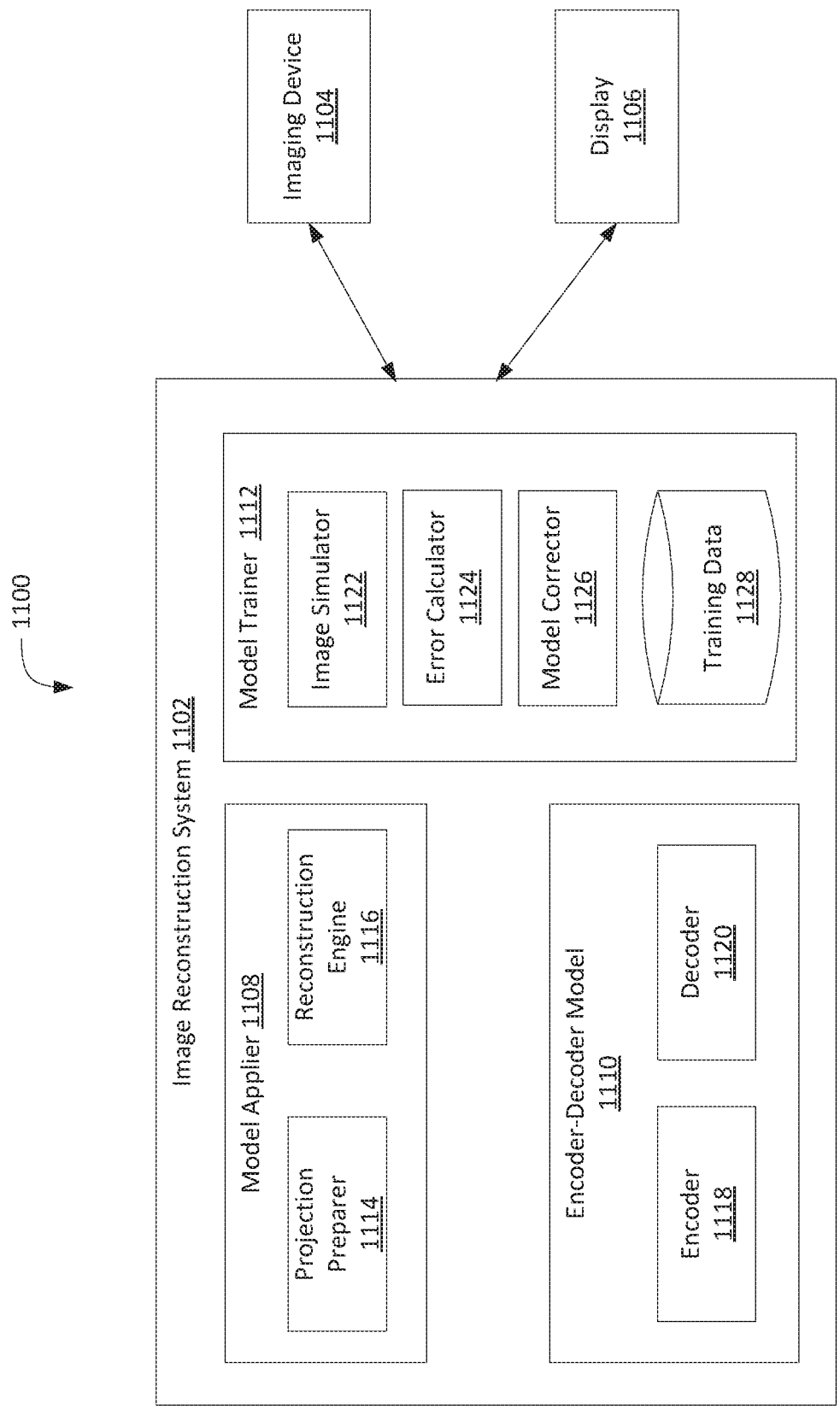
FIG. 11 depicts a block diagram of a system for reconstructing biomedical images.

Referring now to FIG. 11, depicted is a system 1100 for training models for reconstructing biomedical images and using the models to reconstruct biomedical images. The system 1100 may include one or more components of the system 200 detailed herein in Section A. The system 1100 may include an image reconstruction system 1102, an imaging device 1104, and a display 1106. The image reconstruction system 1102 may include a model applier 1108, a convolutional encoder-decoder (CED) model 1110, and a model trainer 1112. The model applier 1108 may include a projection preparer 1114 and a reconstruction engine 1116. The CED model 1112 may include an encoder 1118 and a decoder 1120. The model trainer 1112 may include an image simulator 1122, an error calculator 1124, a model corrector 1126, and training data 1128. Each of the component of system 1100 listed above may be implemented using hardware (e.g., processing circuitry and memory) or a combination of hardware and software.

In some embodiments, the components of the system 1100 may include or perform the functionalities of one or more of the components of the system 200 detailed herein in Section A, among other functions. For example, the image reconstruction system 1102 may perform the functionalities as the image reconstruction system 202. The imaging device 1104 may perform the functionalities as the imaging device 204. The display 1106 may perform the functionalities as the display 206. The model applier 1108 may perform the functionalities as the model applier 208. The projection preparer 214 may perform the functionalities as the projection preparer 1114. The reconstruction engine 216 may perform the functionalities as the reconstruction engine 1116. The encoder-decoder model 1110 may perform the functionalities as the convolutional encoder-decoder model (CED) 210. The encoder 1118 may perform the functionalities as the encoder 218. The decoder 1120 may perform the functionalities as the decoder 220. The model trainer 1112 may perform the functionalities as the model trainer 212. The image simulator 1122 may perform the functionalities as the image simulator 222. The error calculator 1124 may perform the functionalities as the error calculator 224. The model corrector 1126 may perform the functionalities as the model corrector 226. The training data 1128 may include at least some of the training data 228.

The imaging device 1104 may perform a biomedical imaging scan on a subject to acquire a projection dataset. The imaging device 1104 may be in any modality of biomedical imaging, such as tomographic biomedical imaging. The imaging device 1104 may include a PET-computed tomography (CT) scanner, an X-ray CT Scanner, a SPECT CT scanner, an MRI scanner, an ultrasound scanner, and a photoacoustic scanner, among others. To scan, the imaging device 1104 may be pointed toward a designated area on an outer surface of the subject (e.g., human or animal). As the subject is scanned, the imaging device 1104 may generate the projection dataset corresponding to a cross-sectional plane or a volume of the subject through the predesignated area. The projection dataset may be two-dimensional or three-dimensional visualized representation of the subject, including the inner anatomical and physiological structure of the subject.

The projection dataset may include one or more data counts. The projection dataset may include the one or more data counts in accordance with any data structure, such as an array, a binary tree, a matrix, a linked list, a heap, a hash table, a stack, or a queue, among others. In some embodiments, the data counts may be defined in two-dimensions. In some embodiments, the data counts may be defined in three-dimensions. Each data count may correspond to a coordinate of the scanned cross-sectional plane or the volume of the subject. When the cross-sectional plane of the subject is scanned, the projection dataset may be two-dimensional and the coordinates of the data counts may also be two-dimensional. When the volume of the subject is scanned, the projection dataset may be three-dimensional and the coordinates for the data counts may also be three-dimensional. The number of data counts in the projection dataset may depend on a sampling rate of the biomedical imaging scan performed by the imaging device 1104. The imaging device 1104 may be communicatively coupled with the image reconstruction system 1102, and may provide the projection dataset to the image reconstruction system 1102.

The projection preparer 1114 of the model applier 1108 may receive the projection dataset from the biomedical imaging scan performed by the imaging device 1104. The projection preparer 1114 may modify the projection dataset for further processing by the reconstruction engine 1124. The projection preparer 1114 may alter a size of the projection dataset. In some embodiments, the projection preparer 1114 may identify the size of the projection dataset. The projection preparer 1114 may compare the size of the projection dataset with a predefined number. The predefined number may correspond to a number or size of data counts in the projection dataset permitted for input by the encoder-decoder model 1110. The predefined number for the size of the projection dataset. The number of data counts in the projection dataset may differ from the number permitted by the encoder-decoder model 1110. If the size of the projection dataset is less than the predefined permitted number, the projection preparer 1114 may reduce the number of data counts in the projection dataset. If the size of the projection dataset is greater than the predefined permitted number, the projection preparer 1114 may increase the number of data counts in the projection dataset. If the size of the projection dataset is equal to the predefined permitted number, the projection preparer 1114 may maintain the projection dataset.

In some embodiments, the projection preparer 1114 may increase the number of data counts in the projection dataset to the predefined number. The number of data counts in the projection dataset may be less than the number permitted by the encoder-decoder model 1110. In some embodiments, the data count may be at a sampling rate less than a predefined sampling rate permitted by the encoder-decoder model 1110. The predefined number may be of any dimensions (e.g., 288×269×1 or 256×256×3), and may correspond to the number of data counts accepted by the encoder-decoder model 1110. In increasing the number of data counts, the projection preparer 1114 may upsample the projection dataset. The projection preparer 1114 may calculate a difference between the predefined number and the number of data counts in the projection dataset. The projection preparer 1114 may perform zero-padding to the projection dataset by adding the identified difference of additional null data counts. The projection preparer 1114 may then apply an interpolation filter to the zero-padded projection dataset to smooth the discontinuity from the zero-padding.

In some embodiments, the projection preparer 1114 may reduce the number of data counts in the projection dataset to a predefined number. The number of data counts in the projection dataset may be greater than the number permitted by the encoder-decoder model 1110. In some embodiments, the data count may be at a sampling rate greater than a predefined sampling rate permitted by the encoder-decoder model 1110. The predefined number may of any dimensions, and may correspond to the number of data counts permitted by the encoder-decoder model 1110. In reducing the number of data counts, the projection preparer 1114 may downsample or decimate the projection dataset. The projection preparer 1114 may calculate a ratio between the predefined number for the encoder-decoder model 1110 and the number of data counts in the projection dataset. Based on the ratio, the projection preparer 1114 may calculate a decimation factor for the projection dataset. The projection preparer 1114 may apply a low-pass filter with a predetermined cutoff frequency to eliminate high-frequency components of the projection dataset. With the remainder of the projection dataset, the projection preparer 1114 may downsample the projection dataset by the decimation factor by selecting a subset of the data counts corresponding to multiples of the decimation factor. The projection preparer 1114 may also apply an anti-aliasing filter to the downsampled projection dataset to reduce effects of aliasing from downsampling. In some embodiments, the projection preparer 1114 may reduce the number of data counts in the projection dataset to the predefined number by selecting a subset of the data counts in the projection dataset. The subset of the data counts may be at predetermined coordinates within the projection dataset (e.g., 128×128×3 about the middle pixel (64, 64)).

In some embodiments, the projection preparer 1114 may acquire one or more two-dimensional slices of the projection dataset defined in three-dimensions. By acquiring the slices, the projection preparer 1114 may identify or generate a corresponding two-dimensional projection dataset. Each two-dimensional slice may correspond to a portion of the three-dimensional projection dataset along one of the planes of the three-dimensions. The planes of the three-dimensional projection data set may include, for example, an axial plane (sometimes referred herein as a horizontal plane or transverse plane), a coronal plane (sometimes referred herein as a frontal plane), or a sagittal plane (sometimes referred herein as a median or a longitudinal plane), among others. In some embodiments, each two-dimensional slice may be at a predefined spacing from the previous two-dimensional slice within the three-dimensional project dataset. The predefined spacing may specify a number of coordinates from which the next two-dimensional slice is to be acquired. Each two-dimensional projection dataset may include a subset of the data counts corresponding to the portion of the three-dimensional projection dataset alone of one of the planes. The resultant two-dimensional projection dataset may have less data counts than the overall three-dimensional projection dataset.

In some embodiments, the projection preparer 1114 may perform, apply, or otherwise use an interpolation procedure to the three-dimensional projection dataset to acquire the one or more two-dimensional slices. Each two-dimensional slice may correspond to one of the planes of the three-dimensional dataset. In some embodiments, by acquiring the two-dimensional slices in one plane (e.g., axial defined by the z-axis), the projection preparer 1114 may remove the data counts corresponding to other planes in the three-dimensional projection dataset (e.g., transaxial or orthogonal to z-axis). In some embodiments, the projection preparer 1114 may incorporate or combine the data counts of the two-dimensional slice of one plane (e.g., axial defined by the z-axis) onto the data counts of the two-dimensional slice of another plane (e.g., transaxial or orthogonal to z-axis). In combining the data counts from one plane and adding onto another plane, the projection preparer 1114 remove the data counts from other planes (e.g., axial plane or all planes besides the transaxial plane). The removal of the data counts from the other planes may be done with minimal informational loss. The interpolation procedure may include, for example, exact Fourier rebinning, exact time-of-flight (TOF) Fourier rebinning, approximate Fourier rebinning, or approximate TOF Fourier rebinning, among others. In some embodiments, the interpolation procedure may include a denoising procedure or a deblurring procedure. The projection preparer 1114 may use an autoencoder network to perform the denoising procedure or the deblurring procedure onto the two-dimensional slices of the three-dimensional projection dataset. In performing the interpolation, the projection preparer 1114 may apply a transformation function to each two-dimensional slice (sometimes referred herein as a stack or a bin) acquired from the three-dimensional projection dataset. The transformation function applied in interpolation may include, for example, a two-dimensional Fourier transform (e.g., fast Fourier transform (FFT)), a two-dimensional Radon transform, or a two-dimensional Wavelet transform, among others.

With the transformation of the two-dimensional slices of the three-dimensional projection dataset, the projection preparer 1114 may identify adjacent two-dimensional slices. For each corresponding data count in the adjacent two-dimensional slices, the projection preparer 1114 may calculate or generate an approximated data count to form a combinatory two-dimensional projection dataset. In some embodiments, the approximated data count may be generated using an approximation function, such as a linear interpolation, a polynomial interpolation, a bilinear interpolation, a spline interpolation, and a logarithm interpolation, among others. In some embodiments, the generation of the approximated data count in the combinatory two-dimensional projection dataset may be for a predefined region in the two-dimensional slice. The data counts in the combinatory two-dimensional projection dataset outside the predefined region may be set to the data count of one of the adjacent two-dimensional projection datasets.

Upon generating the combinatory two-dimensional projection datasets, the projection preparer 1114 may apply an inverse transform to generate the two-dimensional projection dataset for processing by the reconstruction engine 1116. The inverse transform may include, for example, an inverse two-dimensional Fourier transform (e.g., inverse discrete Fourier transform (DFT)), an inverse two-dimensional Radon transform, or an inverse two-dimensional Wavelet transform, among others. In some embodiments, the projection preparer 1114 may normalize the combinatory two-dimensional projection set, prior to the application of the inverse transform. The two-dimensional projection dataset acquired using the interpolation procedure may be processed by the reconstruction engine 1116.

The reconstruction engine 1116 of the model applier 1108 may apply the encoder-decoder model 1110 to the projection dataset. The reconstruction engine 1116 may have a runtime mode and a training mode. In runtime mode, the reconstruction engine 1116 may receive or access the projection dataset from the imaging device 1114. In some embodiments, the projection dataset may have been processed by the projection preparer 1114. In training mode, the reconstruction engine 1116 may receive or access the projection dataset from the training data 1128. Once the projection dataset is retrieved from the imaging device 1104 or the training data 1128, the reconstruction engine 1116 may apply the projection dataset to an input of the encoder-decoder model 1110. The projection dataset may be two-dimensional, and may have been processed by the projection preparer 1114.

The encoder-decoder model 1110 may include at least one encoder 1118 and at least one decoder 1120. The encoder-decoder model 1110 (and the encoder 1118 and the decoder 1120) may include any form of a neural network, such as a convolutional neural network (e.g., the convolutional encoder-network model 212), a fully connected neural network, a sparse neural network, a deep belief network, a long short-term memory (LSTM) network, among others, in an encoder-decoder sequence. The encoder 1118 may include one or more components of the encoder 218 detailed herein above in conjunction with FIG. 2B, among others. The decoder 11120 may include one or more components detailed herein above in conjunction with FIG. 2C, among others.

The encoder 1118 may include a set of transform layers. The set of transform layers may include one or more parameters (e.g., weights) to convert the two-dimensional projection dataset into a feature map (e.g., feature maps 242A-N). The set of transform layers of the encoder 1118 may be arranged in a series, with an output of one transform layer fed into an input of the succeeding transform layer. Each transform layer of the encoder 1118 may have a non-linear input-to-output characteristic. In some embodiments, the set of transform layers of the encoder 1118 may include a convolutional layer (e.g., convolutional layer 234A-N), a normalization layer (e.g., normalization layer 236A-N), and an activation layer (e.g., activation layer 238A-N), among others. Arranged in series in the encoder 1118, each transform layer may have a size less than or equal to a size of the previous transform layer. The feature map generated by the transform layer may have a size less than or equal to a size of the feature map generated by the previous transform layer in the encoder 1118.

The decoder 1120 may include a set of transform layers. The set of transform layers may include one or more parameters (e.g., weights) to convert the feature map generated by the encoder 1118 into another feature map (e.g., feature maps 256A-N). The set of transform layers of the decoder 1120 may be arranged in a series, with an output of one transform layer fed into an input of the succeeding transform layer. Each transform layer of the decoder 1120 may have a non-linear input-to-output characteristic. In some embodiments, the set of transform layers of the decoder 1120 may include an upsampling layer (e.g., upsampling layer 246A-N), a convolutional layer (e.g., convolutional layer 248A-N), a normalization layer (e.g., normalization layer 250A-N), and an activation layer (e.g., activation layer 252A-N), among others. Arranged in series in the decoder 1120, each transform layer may have a size greater than or equal to a size of the previous transform layer. The feature map generated by the transform layer may have a size greater than or equal to a size of the feature map generated by the previous transform layer in the decoder 1120.

The reconstruction engine 1116 may receive, retrieve, or identify the output of the decoder 1120 of the encoder-decoder model 1110. The output of the decoder 1120 may be a feature map generated from the last transform layer of the decoder 1120. Using the output, the reconstruction engine 1116 may generate a reconstructed tomographic biomedical image. In some embodiments, the reconstruction engine 1116 may identify the feature map outputted by the decoder 1120 as the reconstructed biomedical image. The reconstruction engine 1116 may apply the encoder-decoder model 1110 in a single operation to generate the feature map, thereby reducing the amount of time to generate the reconstructed image. The single pass may be achievable, as the set of transform layers of the encoder 1118 and the set of transform layers of the decoder 1120 are non-linear.

The reconstruction engine 1116 may send the reconstructed image 1158 to the display 1106. The display 1106 may present or render an image output by the image reconstruction system 1102. In some embodiments, the display 1106 may present or render the reconstructed image generated by the CED model 1112 of the image reconstruction system 1102. The display 1106 may include any monitor, such as a liquid crystal display (LCD), an organic light-emitting diode (OLED) monitor, and a cathode ray tube (CRT), among others. The display 1106 may be communicatively coupled with the image reconstruction system 1102, and may render and output the image from the image reconstruction system 1102.

Referring back to FIG. 10A, the PETSTEP simulated dataset was randomly divided on a patient level into three splits. Out of the total 350 randomly generated XCAT patients (291,010 2D sinogram datasets), 245 were used for training (n=203,305, 70%), 52 for validation (n=43,449, 15%), and 53 for testing (n=44,256, 15%). The three sets were kept separate.

The network was implemented in PyTorch, trained on NVIDIA DGX-1 graphics processing units (GPUs), and tested on a NVIDIA GTX 1080Ti GPU. The mean squared error (MSE) between model output and ground truth image was used as loss function, $$MSE = 1/n \sum_{i=1}^{n} (x_i - \gamma_i)^2, \qquad (9)$$

where x is the model image, y the ground truth, and n the number of image pixels. Because SGD was found to yield poorer results, the model was optimized using the Adam optimization method. Training hyperparameters were: learning rate $10^{-4}$; weight decay $10^{-5}$; batch size 70; BN momentum 0.3; bilinear upsampling. Different learning rates and momentums were explored, and the optimal (on the validation set) ones were those used in the final model. The model was optimized on the 291,010/70=4158 mini-batches of the training set over 150 epochs, and the MSE was calculated on the validation set every 5th epoch. After finishing training, the model with optimal performance on the validation set was used on the test set.

Referring to FIG. 10A, the precorrected and cropped test set PET sinograms were reconstructed into images by a single forward pass through the trained DeepPET to generate reconstructed images 1028. In addition, the sinograms were also reconstructed using conventional techniques implemented in PETSTEP (here on a GPU); FBP using precorrected data and a 0.5 frequency scale factor, and OSEM with 5 iterations and 16 subsets using in-loop corrections to avoid altering the statistical distribution of data.

For both methods, the images were post-filtered with a 9.0 mm full width half maximum (FWHM) Gaussian. The FBP and OSEM reconstruction settings (0.5-1 frequency scale factor in steps of 0.1, 1-15 iterations, and 0-30 mm post-filter FWHM in steps of 0.5 mm) were optimized using 100 unique activity images. Each image was then simulated 10 times with PET-STEP using the same noiseless count, into 10 independent noise replicates (total 1,000 images). These 1,000 images were used solely for this optimization. The optimal settings (later used on the test set) were deemed the ones yielding the loss function 1030, such as minimum relative root MSE (rRMSE):

$$rRMSE = \sqrt{MSE}/\bar{\gamma}, \quad (10)$$

where $\bar{\gamma}$ is the ground truth average pixel value.

As a final qualitative test, the trained DeepPET model was applied to real data from two separate GE D690 PET/CT patient scans. The clinical 3D PET data was first precorrected, then converted into stacks of 2D slice sinograms by single slice rebinning, and then inputted to DeepPET. As before, the sinograms were also reconstructed with FBP and OSEM.

For image quality evaluation, three metrics were used. The first was the structural similarity index (SSIM), used for visually perceived image quality where image structure is taken more into account. The higher SSIM value the better, where $0 \leq SSIM \leq 1$ and SSIM=1 if and only if the compared image is identical to the reference (ground truth). For the second metric rRMSE was used according to (10). The peak signal-to-noise ratio (PSNR) was used as the third metric, providing similar information as the RMSE, $$PSNR = 20 \cdot \log 10(y_{max}/\sqrt{MSE}) \quad (11)$$

but in units of dB. Here, $y_{max}$ is the maximum value of the ground truth image.

Referring back to FIG. 11, the model trainer 1112 may use the reconstructed image generated by the model applier 1108 and the training data 1128 to update the encoder-decoder model 1110. In some embodiments, the training data 1128 maintained by the model trainer 1112 may include a training projection dataset. The training projection dataset may be two-dimensional or three-dimensional visualized representation of the subject, including the inner anatomical and physiological structure of the subject. The training projection dataset may be of any biomedical imagining modality, such as radiography (e.g., X-rays and fluoroscopy), magnetic resonance imaging (MRI), ultrasonography, tactile imaging (elastography), photoacoustic imagining, functional near-infrared spectroscopy, and nuclear medicine functional imaging (e.g., positron emission tomography (PET) and single-photo emission computed tomography (SPECT)), among others.

The training projection dataset of the training data 1128 may include one or more data counts. The training projection dataset may include the one or more data counts in accordance with any data structure, such as an array, a binary tree, a matrix, a linked list, a heap, a hash table, a stack, or a queue, among others. Each data count may correspond to a coordinate of the scanned cross-sectional plane or the volume of the subject. When the cross-sectional plane of the subject is scanned, the training projection dataset may be two-dimensional and the coordinates of the data counts may also be two-dimensional. When the volume of the subject is scanned, the training projection dataset may be three-dimensional and the coordinates for the data counts may also be three-dimensional. The number of data counts in the training projection dataset may depend on a sampling rate of the biomedical imaging scan. In some embodiments, the training projection dataset may be the same as the projection dataset used by the model applier 1108 to generate the reconstructed image. In some embodiments, the training data 1128 maintained by the model trainer 1112 may include a sample reconstructed image. The sample reconstructed image may have been previously generated using the corresponding training projection dataset (e.g., using the image simulator 1122 as detailed below). The sample reconstructed image may be labeled as corresponding to the respective sample projection dataset in the training data 1128. In some embodiments, the model trainer 1112 may select a subset of the training projection dataset for training the encoder-decoder model 1110 and another subset of for cross-validation to perform leave-one-out training.

In some embodiments, the training data 1128 may include a training projection dataset for transfer learning. In some embodiments, the training projection dataset for transfer learning may exclude sample data counts for biomedical images and reconstructed biomedical images derived from the sample data counts. In some embodiments, the training projection dataset for transfer learning may include sample data counts for biomedical images and reconstructed biomedical images derived from the sample data counts in a different imagining modality. For example, the training projection dataset for transfer learning may include data counts for ultrasound scans and reconstructed ultrasound images, whereas the target imagining modality may be for PET scans.

The image simulator 1122 may access the training data 1128 to retrieve the training projection dataset. With the training projection dataset, the image simulator 1122 may generate a training reconstructed image. In some embodiments, the image simulator 1122 may apply one or more simulation models to generate the training reconstructed image. The one or more simulation models may differ from the encoder-decoder model 1110 used by the model applier 1108. In some embodiments, the one or more simulation models may include PETSTEP, FBP, and OSEM, among others. The one or more simulation models used by the image simulator 1122 to generate the training reconstructed image may consume more time than the model applier 1108 in generating the reconstructed image. As discussed above, a single pass through the encoder-decoder model 1110 may be performed to generate a reconstructed image.

The error calculator 1124 of the model trainer 1120 may compare the training reconstructed image with the model reconstructed image generated by the model applier 1116 using the encoder-decoder model 1110. In some embodiments, when the training data used is for transform learning, both the training reconstructed image and the model reconstructed image may be of a different biomedical imagining modality from the target modality. In some embodiments, when the training data used is for transform learning, both the training reconstructed image and the model reconstructed image may not be of biomedical images. In some embodiments, the training reconstructed image may be generated by the image simulator 1122 using the training projection dataset. In some embodiments, the training reconstructed image may be retrieved from the training data 1128. The model reconstructed image may be generated by the model applier 1108 using the training projection dataset while in training mode. By comparing, the error calculator 1124 may find or identify one or more differences between the training reconstructed image and the model reconstructed image.

The error calculator 1124 may determine an error measure between the training reconstructed image and the model reconstructed image. The error measure may indicate the one or more differences between the training reconstructed image and the model reconstructed image. In some embodiments, the error calculator 1124 may calculate the mean square error (MSE) as the error measure between the training reconstructed image and the model reconstructed image. In some embodiments, the error calculator 1124 may calculate a mean integrated square error as the error measure. In some embodiments, the error calculator 1124 may calculate a quadratic loss as the error measure. In some embodiments, the error calculator 1124 may calculate an entropy loss (e.g., cross-entropy or relative entropy) as the error measure. In some embodiments, the error calculator 1124 may calculate the root mean square error as the error measure. In some embodiments, the error calculator 1124 may calculate a pixel-wise difference between the training reconstructed image and the model reconstructed image. Each image may be two-dimensional or three-dimensional, and may be of a predefined pixel size. The error calculator 1124 may traverse the pixels of both the training reconstructed image and the model reconstructed image. For each corresponding pixel of the same coordinates, the error calculator 1124 may calculate a difference between one or more values (e.g., intensity, gray-scale, or red-blue-green) of the pixel for the training reconstructed image versus the one or more values of the corresponding pixel for the model reconstructed image. Using the differences over the pixels, the error calculator 1124 may calculate the error.

Based on the comparison between the reconstructed image from the training data 1128 and the reconstructed image generated using the encoder-decoder model 1110, the model corrector 1126 of the model trainer 1112 may modify the encoder-decoder model 1110. Using the error measure determined by the error calculator 1124, the model corrector 1126 may update the encoder-decoder model 1110. In some embodiments, the model corrector 1126 may modify or update the encoder 1118 and/or the decoder 1120 using the error measure. The model corrector 1126 may change, adjust, or set the one or more parameters of the set of transform layers of the encoder 1118 or the decoder 1120 (including the convolution layer, the normalization layer, and the activation layer) based on the error measure. In some embodiments, the model corrector 1126 may increase or decrease the one or more parameters of the set of transform layers of the encoder 1118 and of the decoder 1120 based on whether the error measure is positive or negative. In some embodiments, in modifying the parameters in the encoder 1118 or the decoder 1120, the model corrector 1126 may perform one or more regularizations on at least one of the transform layers in the encoder 1118 or the decoder 1120 based on the error measure. The regularization may include, for example, dropout, drop connect, stochastic pooling, or max pooling, among others. In some embodiments, the model corrector 1126 may modify, adjust, or set the size of at least one of the transform layers in the encoder 1118 or the decoder 1120 based on the error measure.

By repeatedly comparing training reconstructed images with the model reconstructed images, the model trainer 1112 may update the encoder-decoder model 1110 until the model reconstructed images significantly match the training reconstructed images (e.g., within 10%). In some embodiments, the model corrector 1126 may determine whether the encoder-decoder model 1110 has reached convergence. In some embodiments, the model corrector 1126 may compare the encoder-decoder model 1110 prior to the update with the encoder-decoder model 1110 of the update. In comparing, the model corrector 1126 may determine a difference measure between the parameters of the encoder-decoder model 1110 prior to the update with the parameters of the encoder-decoder model 1110 with the update. The model corrector 1126 may compare the difference to a predetermined threshold. If the difference is less than the predetermined threshold, the model corrector 1126 may determine that the encoder-decoder model 1110 has reached convergence, and may terminate the training mode for the encoder-decoder model 1110. On the other hand, if the difference is greater than the threshold, the model corrector 1126 may determine that the encoder-decoder model 1110 has not yet reached convergence. The model corrector 1126 may further continue to train the encoder-decoder model 1110 using the training data 1128.

Figure 12A:
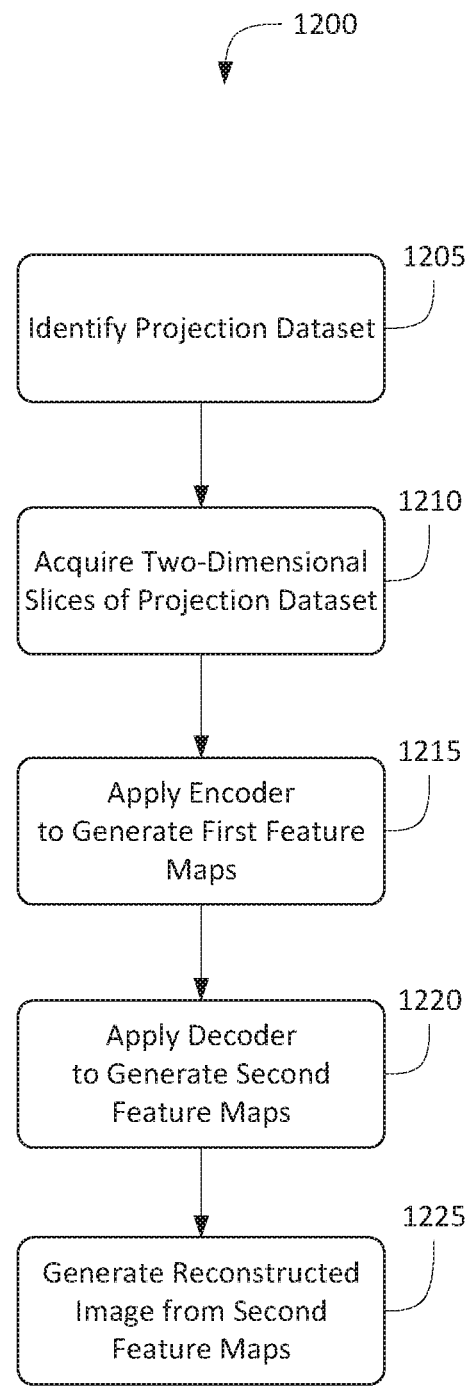
FIG. 12A depicts a flow diagram of a method of reconstructing biomedical images using encoder-decoder models.

Referring to FIG. 12A, depicted is a flow diagram of a method 1200 of reconstructing biomedical images. The method 1200 may be implemented or performed using the schema 100 as detailed in conjunction with FIGS. 1A and 1B, the system 200 as detailed in conjunction with FIGS. 2A-2C, the schema 1000 detailed in conjunction with FIGS. 10A and 10B, the system 1100 as detailed herein in conjunction with FIG. 11, or the computing system 1600 described below in conjunction with FIG. 16A-D. In brief overview, an image reconstructor may identify a projection dataset (1205). The image reconstructor may acquire two-dimensional slices of the projection dataset (1210). The image reconstructor may apply an encoder to generate first feature maps (1215). The image reconstructor may apply a decoder to generate second feature maps (1220). The image reconstructor may generate a reconstructed image from second feature maps (1225).

In further detail, an image reconstructor may identify a projection dataset (1205). The image reconstructor may retrieve the projection dataset from a biomedical imaging device. The projection dataset may include one or more data counts defined in three-dimensions. The one or more data counts may correspond to a cross-sectional area or a volume of a subject, including the internal anatomical and physiological structure of the subject. The one or more data counts may be of a predefined size. The image reconstructor may modify the number of data counts in the projection dataset. In some embodiments, the image reconstructor may up-sample or down-sample the projection dataset to modify the number of data counts.

The image reconstructor may acquire two-dimensional slices of the projection dataset (1210). The image reconstructor may identify one or more two-dimensional projection datasets from the three-dimensional projection dataset. Each two-dimensional projection dataset may correspond to one of the planes in the three-dimensional projection dataset. The image reconstructor may also perform an interpolation procedure in acquiring the two-dimensional projection datasets.

The image reconstructor may apply an encoder to generate first feature maps (1215). The encoder may be of an encoder-decoder model. The encoder may contract the size of the projection data to generate the first feature maps using the two-dimensional projection dataset. The encoder may include a set of transform layers with a non-linear input-to-output characteristic. The set of transform layers may include one or more convolution layers, one or more normalization layers, and one or more activation layers. The size the transform layer may increase relative to the size of the previous transform layer. With each successive application of the transform layers in series, the number of feature maps may increase while the size of each individual feature map may decrease. Each feature map may be of a predefined size based on the size of the input and the size of the transform layer.

The image reconstructor may apply a decoder to generate second feature maps (1220). The decoder may be of the encoder-decoder model. The image reconstructor may apply the output of the encoder as the input of the decoder. The decoder may use the projection dataset to generate the reconstructed image. The decoder may also include a set of transform layers. The set of transform layers may include one or more upsampling layers, one or more convolution layers, one or more normalization layers, and one or more activation layers. Each transform layer may be of a predefined size. The set of feature maps outputted by the encoder may be applied to the decoder. The output of one transform layer at the decoder may successively be applied to next transform layer of the decoder. Each feature map may correspond to the transform layer. Each feature map may be of a predefined size based on the size of the input and the size of the filter. With each successive application of the transform layer (including the upsampling layer, the convolution layer, normalization layer, and the activation layer), the number of feature maps may decrease while the size of each individual feature map may increase. The image reconstructor may generate a reconstructed image from second feature maps (1225). Using the feature maps generated by the last transform layer of the decoder, the image reconstructor may generate the reconstructed image. The reconstructed image may be rendered on a display. The reconstructed image may be stored.

Figure 12B:
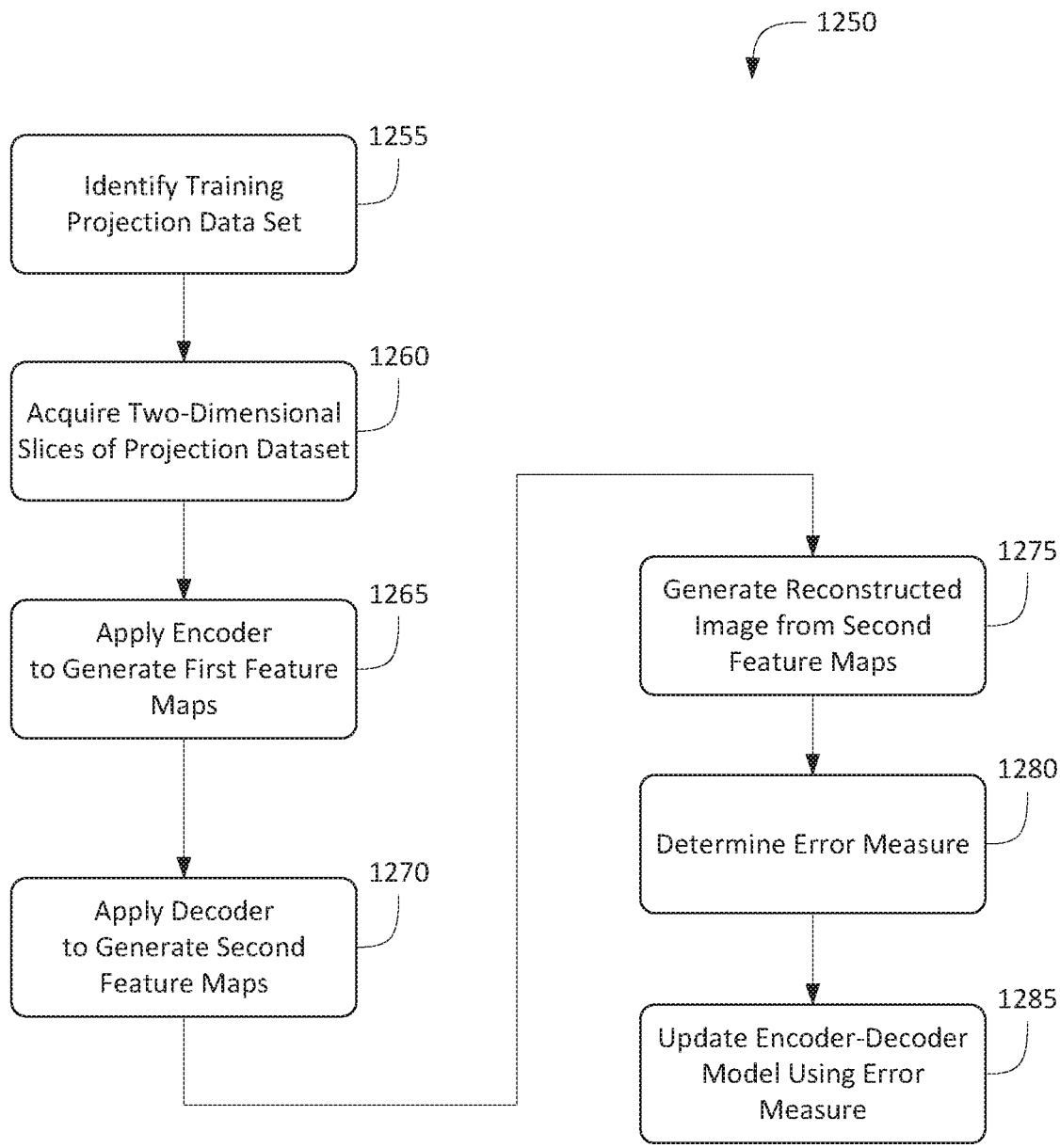
FIG. 12B depicts a flow diagram of a method of training encoder-decoder models for reconstructing biomedical images.

Referring to FIG. 12B, depicted is a flow diagram of a method 1250 of training models for reconstructing biomedical images. The method 1250 may be implemented or performed using the schema 100 as detailed in conjunction with FIGS. 1A and 1B, the system 200 as detailed in conjunction with FIGS. 2A-2C, the schema 1000 detailed in conjunction with FIGS. 10A and 10B, the system 1100 as detailed herein in conjunction with FIG. 11, or the computing system 1600 described below in conjunction with FIG. 16A-D. In brief overview, an image reconstructor may identify a training projection dataset (1255). The image reconstructor may acquire two-dimensional slices of the projection dataset (1260). The image reconstructor may apply an encoder to generate first feature maps (1265). The image reconstructor may apply a decoder to generate second feature maps (1270). The image reconstructor may generate a reconstructed image from second feature maps (1275). The image reconstructor may determine an error measure (1280). The image reconstructor may update an encoder-decoder model using an error measure (1285).

In further detail, an image reconstructor may identify a training projection dataset (1255). The image reconstructor may retrieve the projection dataset from a training database. The projection dataset may include one or more data counts defined in three-dimensions. The one or more data counts may correspond to a cross-sectional area or a volume of a subject, including the internal anatomical and physiological structure of the subject. The one or more data counts may be of a predefined size. The image reconstructor may modify the number of data counts in the projection dataset. In some embodiments, the image reconstructor may up-sample or down-sample the projection dataset to modify the number of data counts.

The image reconstructor may acquire two-dimensional slices of the projection dataset (1260). The image reconstructor may identify one or more two-dimensional projection datasets from the three-dimensional projection dataset. Each two-dimensional projection dataset may correspond to one of the planes in the three-dimensional projection dataset. The image reconstructor may also perform an interpolation procedure in acquiring the two-dimensional projection datasets.

The image reconstructor may apply an encoder to generate first feature maps (1265). The encoder may be of an encoder-decoder model. The encoder may contract the size of the projection data to generate the first feature maps using the two-dimensional projection dataset. The encoder may include a set of transform layers with a non-linear input-to-output characteristic. The set of transform layers may include one or more convolution layers, one or more normalization layers, and one or more activation layers. The size the transform layer may increase relative to the size of the previous transform layer. With each successive application of the transform layers in series, the number of feature maps may increase while the size of each individual feature map may decrease. Each feature map may be of a predefined size based on the size of the input and the size of the transform layer.

The image reconstructor may apply a decoder to generate second feature maps (1270). The decoder may be of the encoder-decoder model. The image reconstructor may apply the output of the encoder as the input of the decoder. The decoder may use the projection dataset to generate the reconstructed image. The decoder may also include a set of transform layers. The set of transform layers may include one or more upsampling layers, one or more convolution layers, one or more normalization layers, and one or more activation layers. Each transform layer may be of a predefined size. The set of feature maps outputted by the encoder may be applied to the decoder. The output of one transform layer at the decoder may successively be applied to next transform layer of the decoder. Each feature map may correspond to the transform layer. Each feature map may be of a predefined size based on the size of the input and the size of the filter. With each successive application of the transform layer (including the upsampling layer, the convolution layer, normalization layer, and the activation layer), the number of feature maps may decrease while the size of each individual feature map may increase. The image reconstructor may generate a reconstructed image from second feature maps (1275). Using the feature maps generated by the last transform layer of the decoder, the image reconstructor may generate the reconstructed image. The The image reconstructor may determine an error measure (1280). The model reconstructed image may be generated from the encoder-decoder model. The training reconstructed image, on the other hand, may be generated using the training projection dataset and a simulation model. The image reconstructor may calculate a mean square error (MSE) between the training reconstructed image and the model reconstructed image as the error measure. The image reconstructor may also calculate the root mean square error as the error measure as the error measure. The image reconstructor can calculate a pixel-by-pixel difference between the training reconstructed image and the model reconstructed image. Using the differences, the image reconstructor may calculate the error measure.

The image reconstructor may update an encoder-decoder model using an error measure (1285). The image reconstructor may apply the error measure to the encoder of the encoder-decoder model. The image reconstructor may modify the convolutional layers, the normalization layers, and the activation layers of the encoder. The image reconstructor may change or set the one or more parameters of the transform layers of the encoder in accordance with the error measure. The image reconstructor may modify the convolutional layers, the normalization layers, and the activation layers of the decoder. The image reconstructor may change or set the one or more parameters of the transform layers of the decoder in accordance with the error measure. The image reconstructor may repeatedly update the encoder-decoder model until the encoder-decoder model reaches convergence.

6. Results

Figure 13A:
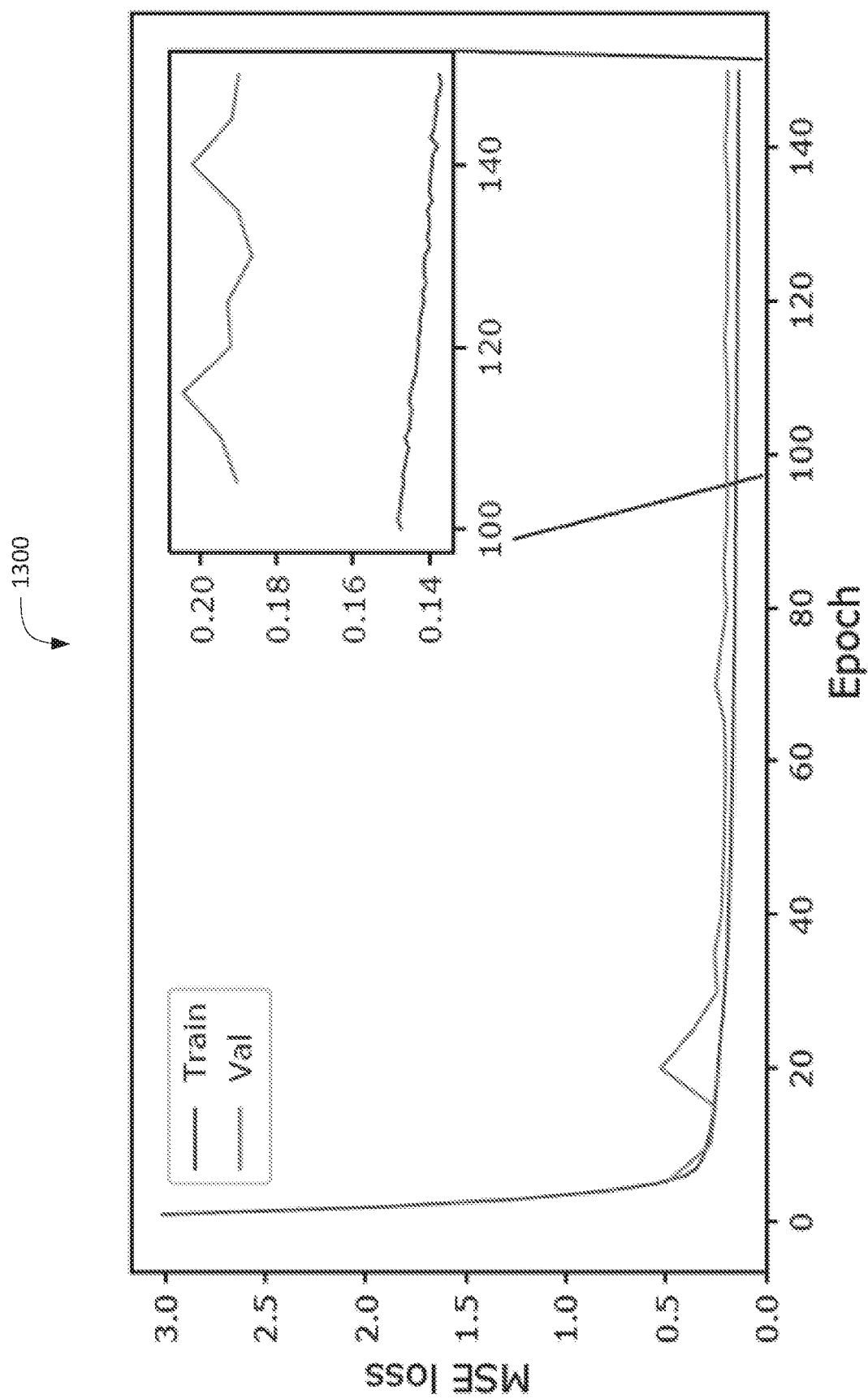
FIG. 13A depicts a graph of convergence behavior of average mean square error (MSE) of the convolutional encoder-decoder (CED) architecture.

Referring now to FIG. 13A, depicted is a graph of convergence behavior of average mean square error (MSE) of the convolutional encoder-decoder (CED) architecture. The graph shows the average loss of the training and validation sets as a function of training epoch. As shown, the loss decreases as a result of the network learning to better represent the features of the data.

Figure 13B:
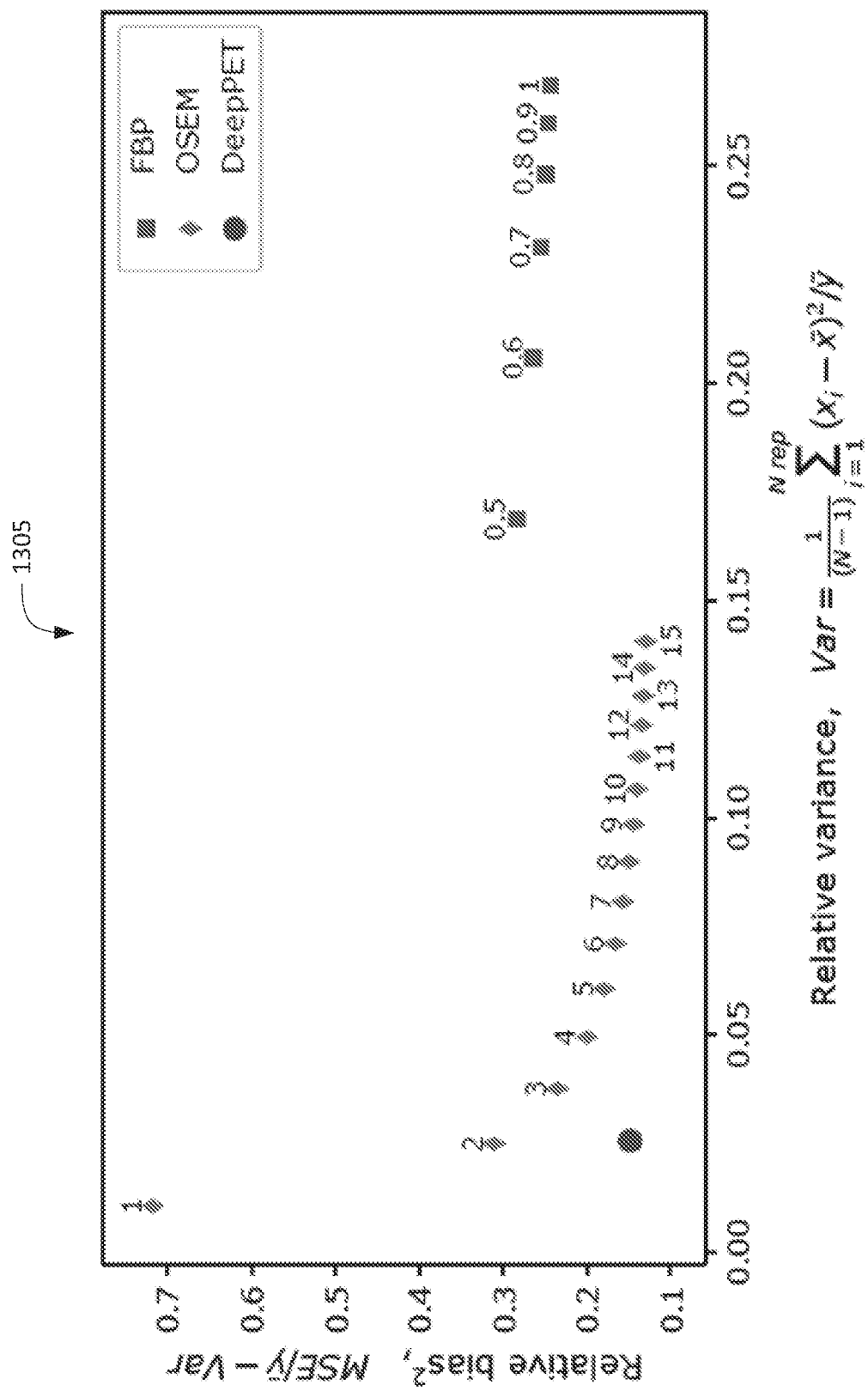
FIG. 13B depicts a graph of relative mean squared error (MSE) versus variance in reconstructed images generated using various models.
Figure 14:
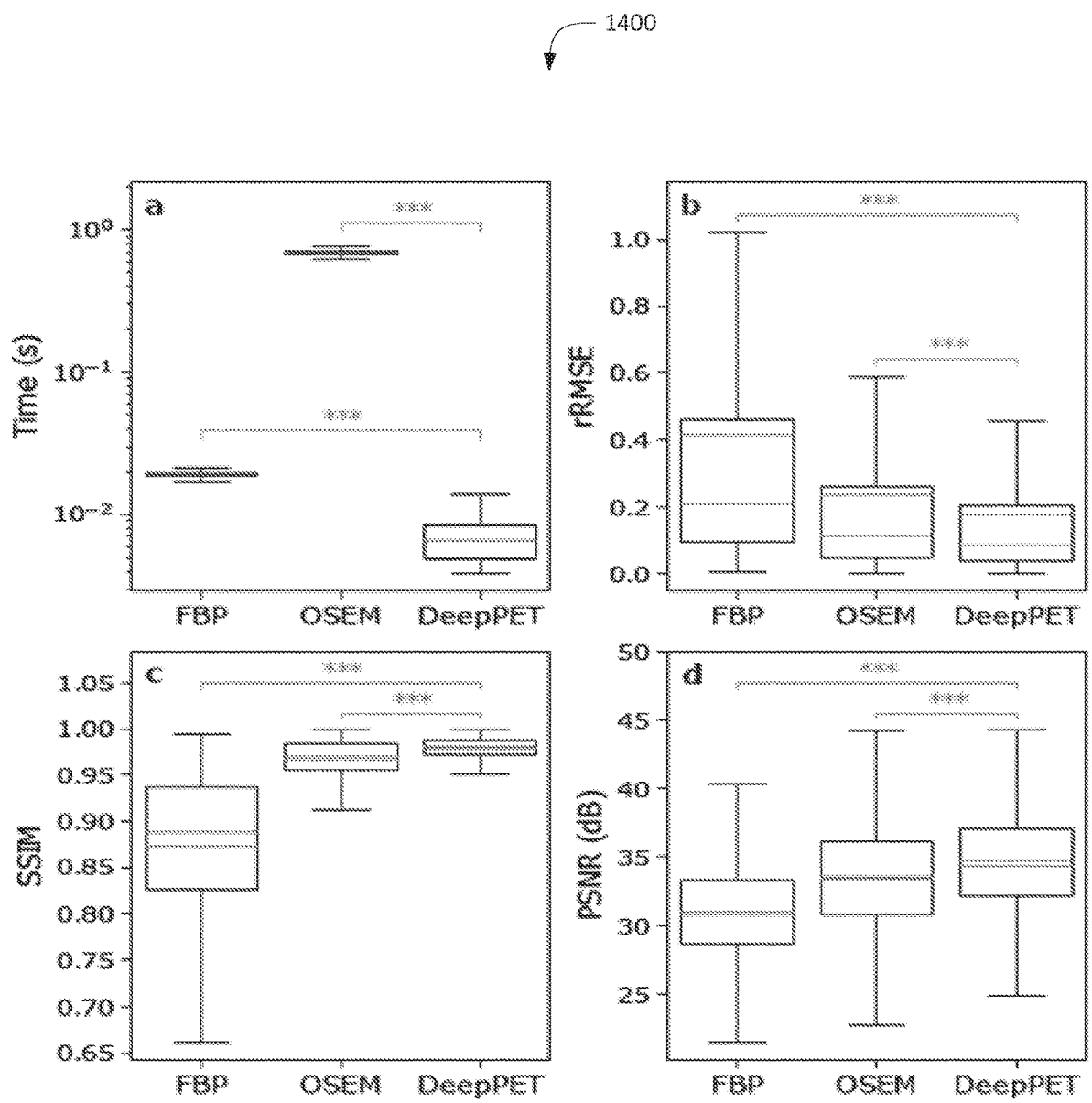
FIG. 14 depicts a graph of average time for generating reconstructed images using various models.

Referring now to FIG. 13B, depicted is a graph of relative mean squared error (MSE) versus variance in reconstructed images generated using various models. The graph shows the average bias (MSE minus variance) versus noise (variance between noise replicates) for the 100×10 images of the different OSEM iteration numbers, and FBP frequency scales for the optimal postfilter FWHM of 9 mm, in comparison to DeepPET. As seen, DeepPET places superior to both FBP and OSEM with comparatively lesser noise and bias. The average (n=44,256) reconstruction time per image in the test set, together with the average SSIM and rRMSE using FBP, OSEM, and DeepPET are found. With an average execution speed of 6.47±0.01 ms per image, DeepPET compared favorably to the conventional methods of FBP at 19.9±0.2 ms (3 times slower), and OSEM at 697.0±0.2 ms (108 times slower). Furthermore, the resulting image quality of DeepPET also out-performed the conventional methods in terms of SSIM, being 0.97958±0.00005 for DeepPET, compared to 0.8729±0.0004 for FBP (11% lower), and 0.9667±0.0001 for OSEM (1% lower). In addition, the average rRMSE of DeepPET was the lowest at 0.6012±0.0009, with values of 0.922±0.001 for FBP (53% higher), and 0.6669±0.0007 for OSEM (11% higher). The PSNR was highest for DeepPET at 34.69(2) dB, while 30.85±0.02 dB for FBP (3.84 dB lower), and 33.59±0.02 dB for OSEM (1.09 dB lower). Standard errors of the means are noted in parentheses. Comparing the 44,256 test set images one-by-one, DeepPET had a higher SSIM than FBP and OSEM for 100% and 80% of the images, respectively. Equivalently, DeepPET had a lower rRMSE than FBP and OSEM for 100% and 75% of the images (same numbers for PSNR). In terms of reconstruction speed, DeepPET was faster than both FBP and OSEM for 100% of the images.

Since the same sinogram data was reconstructed using different methods, a repeated measures one-way ANOVA test with Bonferroni correction was used to confirm that the improvements observed using DeepPET over both FBP and OSEM, in terms of reconstruction speed, SSIM, rRMSE, and PSNR were statistically significant ($p<10^{-10}$).

The SSIM values for the images are high (close to 1) for OSEM and DeepPET since each value is calculated as the average over the entire image, and there is a lot of background in the images that is correctly reconstructed for these methods. Masked SSIM values, i.e. the SSIM over only those pixels with non-background ground truth, were 0.8816±0.0002 for DeepPET, 0.8729±0.0004 for FBP (1% lower), and 0.8136±0.0004 for OSEM (8% lower). Corresponding values for rRMSE are 0.2163±0.0003, 0.3019±0.0005 (40% higher), and 0.2441±0.0003 (13% higher) for DeepPET, FBP and OSEM, respectively. The superior performance of DeepPET over FBP and OSEM thus still holds for masked SSIM (ANOVA p<10-10). As expected, the performance of FBP relative the other methods increase when masking off the background, which for FBP contains notorious streak artifacts.

Figure 15A:
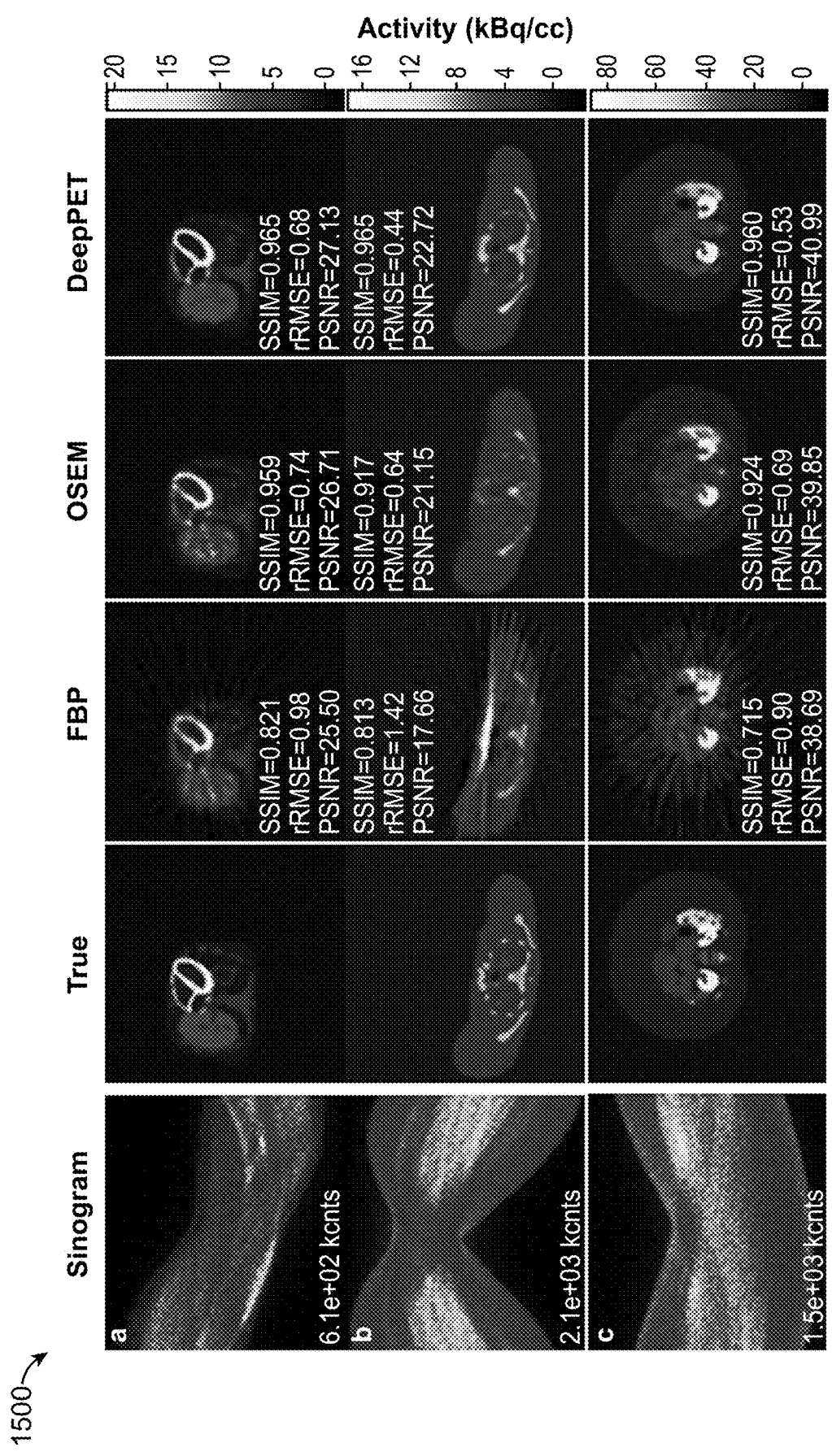
FIG. 15A-C each depicts example reconstructed images using various models.
Figure 15A:
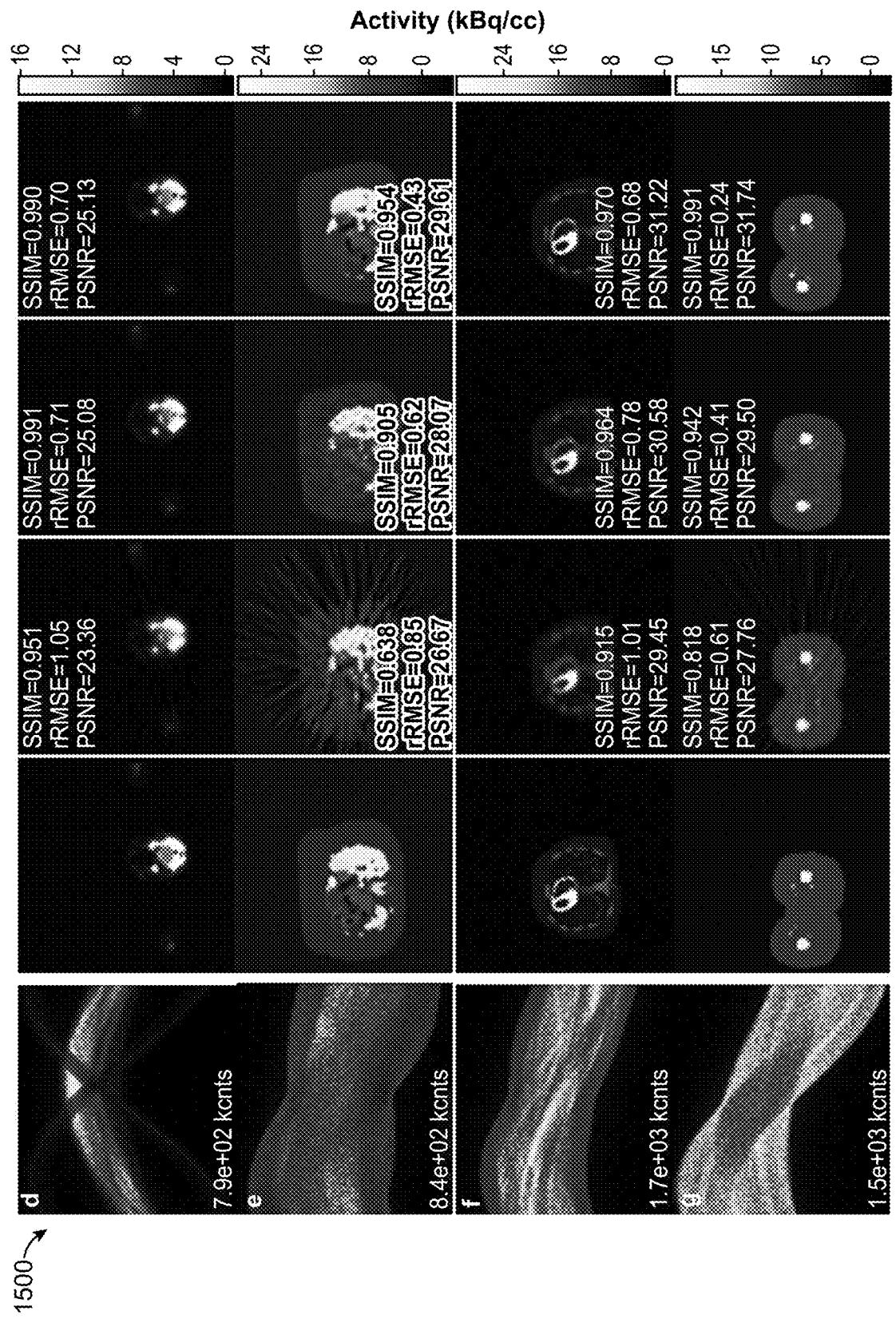
Figure 15B:
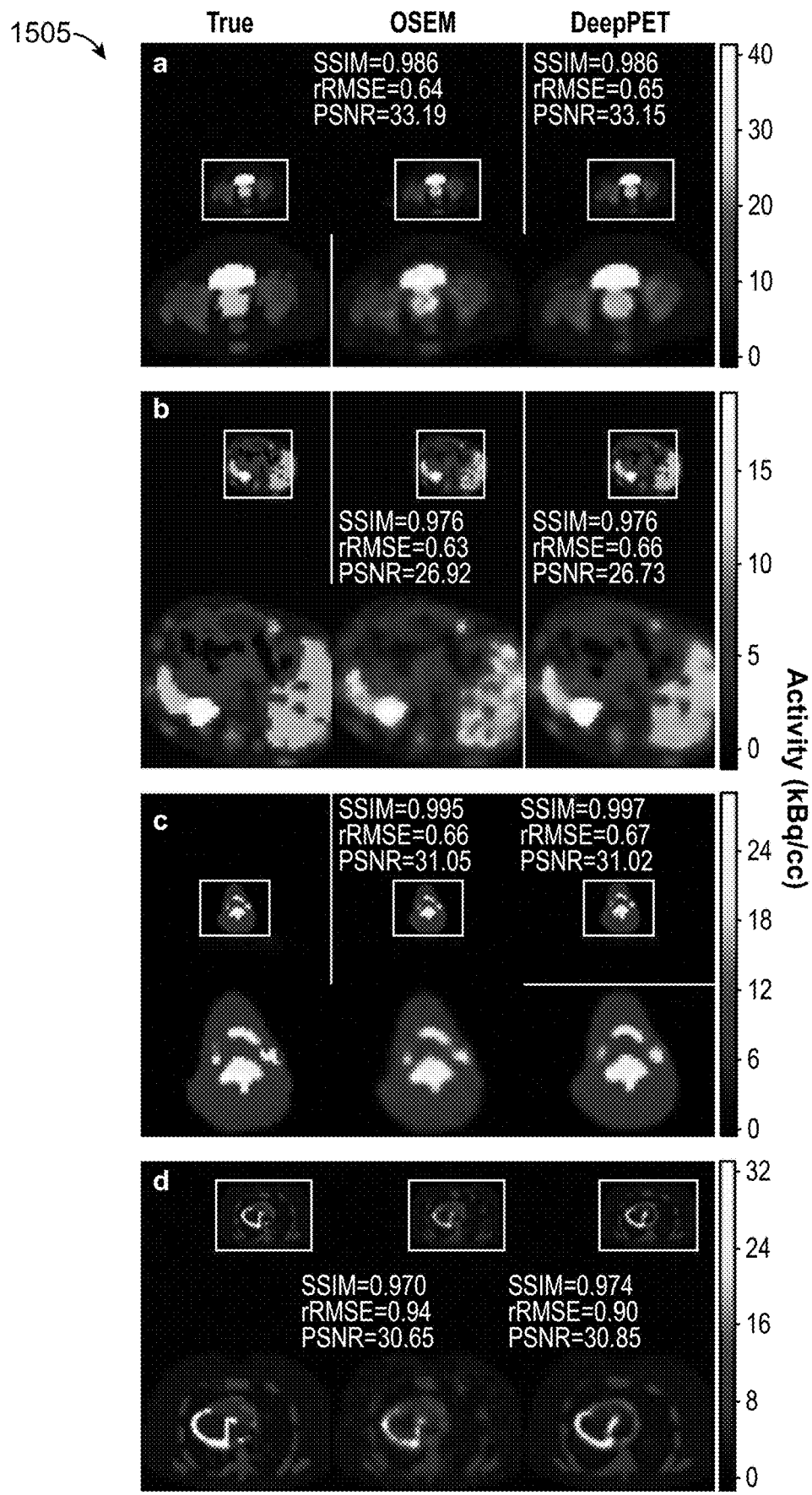

Referring now to FIGS. 15A and 15B, depicted are example reconstructed images using various models. Example FBP, OSEM, and DeepPET reconstructions from the test set are shown in FIG. 15A. The images were randomly chosen with constraints on body location to obtain diverse images. As shown, DeepPET generated less noisy images while preserving edges, which is especially apparent in large homogeneous areas (e.g. FIG. 15A (a) and (g)). Qualitative differences between OSEM and DeepPET are more discernible in FIG. 15B. This figure show cases where OSEM has similar image quality to DeepPET based on the rRMSE and/or SSIM measures to show that even in these cases, the OSEM images appear noisier, less detailed, and having less sharp edges. The same or better performance of OSEM with these metrics appears incongruous with the visual quality of the images wherein fine details appear to be better preserved with less noise with this DeepPET-based method.

Figure 15C:
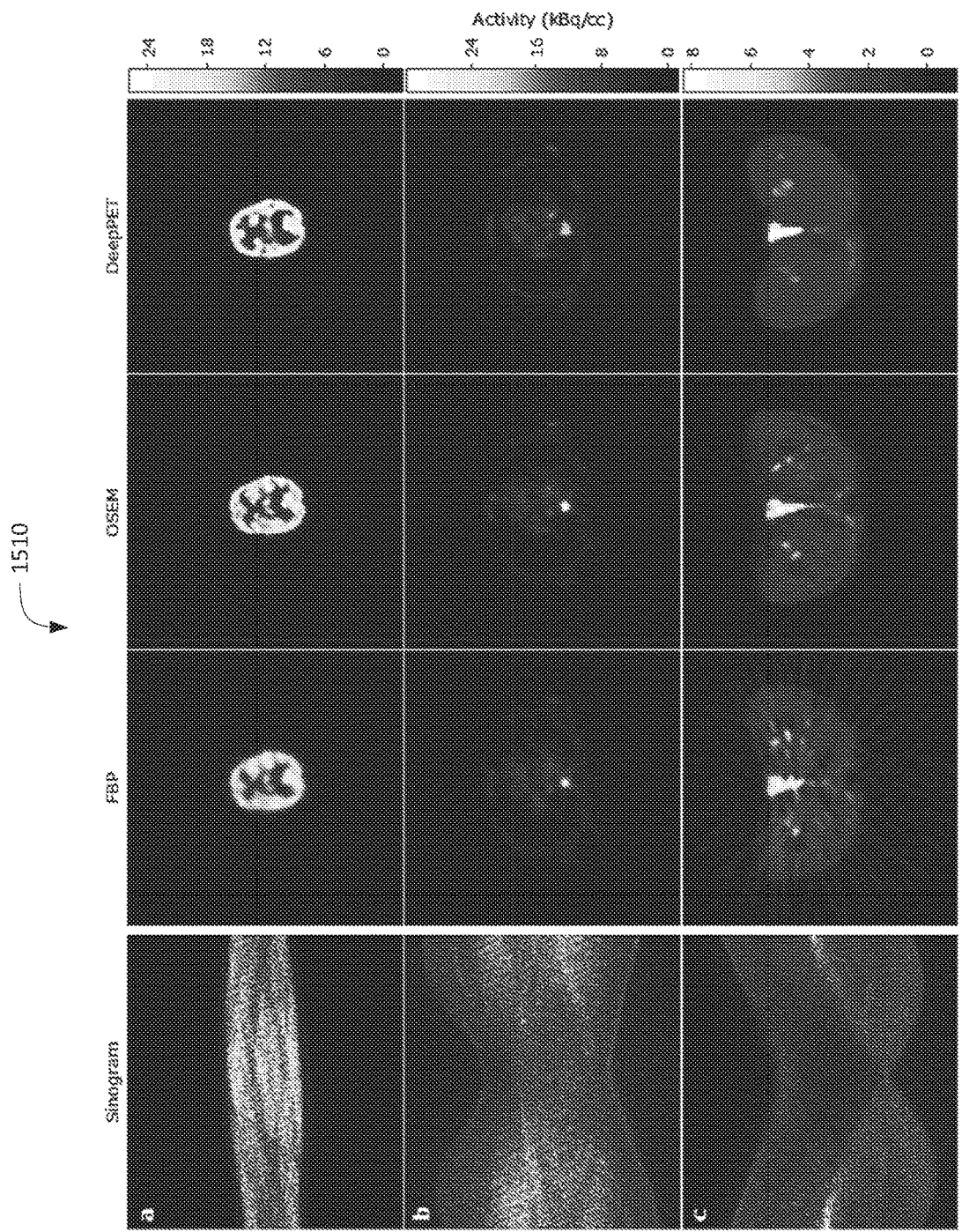

Referring now to FIG. 15C, depicted are example reconstructed images using various models with clinical data. As a proof of concept, shows DeepPET reconstructions using the clinical data. Because this was real patient data, there was no ground truth for comparison. Despite the fact that DeepPET was trained using simulated data, when using real patient data, it produced perceptually smoother and more detailed images compared to either OSEM or FBP. It should be noted that the patient sinogram data was noisy due to the extraction of 2D slices from the 3D data.

7. Discussion

The use of deep learning methods for medical imaging applications is rapidly increasing, and tomographic medical image reconstruction is no exception, with new approaches being proposed on an accelerated time line. However, the vast majority of these approaches are post-processing approaches, where a noisy initial image is denoised and restored. In addition, other approaches using CT sinogram data employ iterative schemes where deep learning methods augment the iterative process. Such approaches may use a tomographic projection operator, increasing their computational effort. Instead, an end-to-end deep learning image reconstruction here may directly use the sinogram data to create images without the application of a projection operator. In fact, it is precisely for these reasons, that there are no forward- or back-projection operations, nor any iterations, that make DeepPET's reconstructions so fast.

As shown in the results, DeepPET was 108 times faster than standard OSEM and 3 times faster than FBP. DeepPET may involve one pass to reconstruct an image from sinogram data, whereas other techniques may take multiple iterations. Regularized iterative reconstruction methods were not compared, but the speed gain is expected to be far greater due to the larger number of iterations typically used to ensure more uniform image convergence, and likely longer computations per iteration for regularized methods. On a clinical system (here a GE D690/710), with the vendor algorithms implemented on a dedicated reconstruction computer, a typical clinically used OSEM reconstruction takes approximately 90 s for a 3D sinogram (553 times more data than 2D), roughly equivalent to 163 ms for 2D, which is 25 times longer than DeepPET. Furthermore, although the network was trained on state-of-the-art Volta GPUs on NVIDIA DGX-1 compute nodes, testing was done on a common NVIDIA GTX 1080Ti GPU. For clinical practice, single forward passes are used for image reconstruction, limiting the demand for large memory and computational power, enabling the use of a simple GPU. For full 3D reconstruction, due to oblique projections, the sinogram data size increases by a factor of more than 500, which limits the use of some GPUs due to memory issues.

The bias versus variance trade-off depicted in FIG. 13B shows that neither FBP nor OSEM are capable of producing images that simultaneously have the same low bias and variance as DeepPET. Hence, according to the results, images of the same quality as those produced by DeepPET are unobtainable using conventional, unregularized image reconstruction methods (i.e., FBP and OSEM). DeepPET reconstructions (FIGS. 15A and 15B), especially in comparison with FBP and OSEM, are consistent with the conjecture that the DeepPET model learns not only the mapping from sinogram to image, but also the appropriate noise model, effectively regularizing the ill-posedness of the inverse problem. This is important because it allows the use of precorrected data, which results in a simpler CED architecture and a smaller memory footprint, both contributing to improved reconstruction speed. Additionally, this may also improve images from acquisitions with a lot of deadtime, where the Poisson noise model is less accurate. As a result, the projection data noise is suppressed during the forward pass, producing smooth images while preserving resolution.

The application of the trained model on real patient data (as depicted in FIG. 15C) shows the potential for clinical use of the DeepPET system, where it can reconstruct smooth images while preserving edges. However, without ground truth it is difficult to make quantitative claims, or judge the authenticity of structures that are made apparent with DeepPET. Furthermore, since PET data is acquired in 3D, individual 2D slices were extracted to use in DeepPET, and no time-of-flight information was used. The clinical data thus had higher noise, and the resulting images were likely of lesser quality than those resulting from full 3D data.

One major benefit with PET over many other modalities is that it is inherently quantitative. Hence, the network input and output, though differing in size and structure (as they come from different data domains: sinogram vs. image), are related to one another, where pixel units go from sinogram counts (registered photon pairs) on the input side, to image pixels in activity concentration (Bq/cc) as output. In addition, the spatial correlation between neighboring bins (pixels) in the sinograms (related via system model) are not the same as those in the reconstructed image. The use of a convolutional encoder is therefore not as intuitive as when working with ordinary image input. Due to memory, time, and over-fitting limitations, a fully connected network on the other hand is difficult or even infeasible for large 2D (and 3D) data due to the huge number of network weights. As an example, a single fully connected layer taking one sinogram of 288×381 to a 128×128 image may include about 2 billion weights.

Furthermore, although focused on PET, the methodology presented is also valid for other types of tomographic data, such as SPECT and CT. SPECT data is even noisier than PET data and has poorer intrinsic resolution making a prime candidate for the approach detailed herein. CT data is much less noisy than PET, and has higher spatial resolution, also making it a suitable candidate for the approach detailed herein.

8. Observations

Synthetic data may be used instead of real patient data. This may provide ground truth for the training data. In particular, the simulations use a forward projection operator and noise models and source distributions defined by the XCAT model. While the use of PETSTEP provides the benefit of allowing us to rapidly generate ground truth images and simulated projection data, it implicitly introduce both system and noise models into the training data. Furthermore, it is possible that the network will learn the simplifications and assumptions used in the simulations, which may not be accurately reflected in real patient data.

These issues can be alleviated by using a full MC simulation model such as GATE, which can provide a more accurate representation of the sinogram data. However, the use of MC can be computationally expensive, where such simulations can take days, weeks, or even months to produce the projection data for one realization. Using hundreds of thousands of images, however, may be impractical. It is noted that PETSTEP has been validated against GATE MC and proven to provide realistic results, which gives confidence that this approach is reasonable.

With regard to the synthetic patient source distributions, the XCAT phantom was used. Although this phantom is realistic, and we randomly set its adjustable geometry, shape, material and activity parameters, such population is not quite the same as real patient population. Nevertheless, the training, testing, and validation data used here that are based on XCAT do have a wide range of appearances and contrasts, containing everything from highly detailed regions to smooth homogeneous ones, as well as large, small, hot, and cold structures. Furthermore, application on real patient data (FIG. 15C) shows that DeepPET performs well in clinical scenarios after training on XCAT.

Although comparisons to regularized iterative techniques have not been included, it is enough to only compare DeepPET to reconstruction methods that are widely available in the clinic, namely OSEM. Another reason that DeepPET is not compared to regularized image reconstruction is that regularization weights are often difficult to automate, especially when the underlying source distribution varies both in and between patients, and often entail user oversight and input. For tens of thousands of images, this makes this approach challenging or even infeasible. DeepPET on the other hand has an inherent regularizer learned from the training data that utilized many diverse anatomies and noise levels.

Finally, end-to-end networks for tomographic image reconstruction can have generalization errors that do not have a well-defined bound. As a result, there is no guarantee that any particular data used in this type of network will produce artifact free images. However, because of the nature of this approach, using large and diverse test data sets, one can statistically quantify the probability distribution of large local errors (e.g., the l∞-norm) and giving the frequency and size of the reconstruction errors. It is conjectured that this type of approach, when outliers can be shown to be acceptably rare, will provide clinicians with confidence in the resulting images.

8. Conclusions

The present disclosure provides the first systematic study of an end-to-end deep learning model that is capable of directly reconstructing quantitative PET images from sinogram data without the use of system and noise models. There are four advantages may include: (i) a novel encoder-decoder architecture for PET sinogram data, (ii) that does not rely on any assumptions with respect to the physical system, noise distributions nor regularization model, (iii)

which on average increases the reconstruction speed over the conventional OSEM image reconstruction by a factor of 108, (iv) while also improving image quality by on average 1% (SSIM), 11% (rRMSE), and 1.1 dB (PSNR) respectively. This approach shows the potential of deep learning in this domain and is part of a new branch in tomographic image reconstruction. Ultimately the gain in quality and speed should lead to higher patient throughput, as well as more reliable and faster diagnoses and treatment decisions, and thus better care for cancer patients.

C. Computing and Network Environment

Figure 16A:
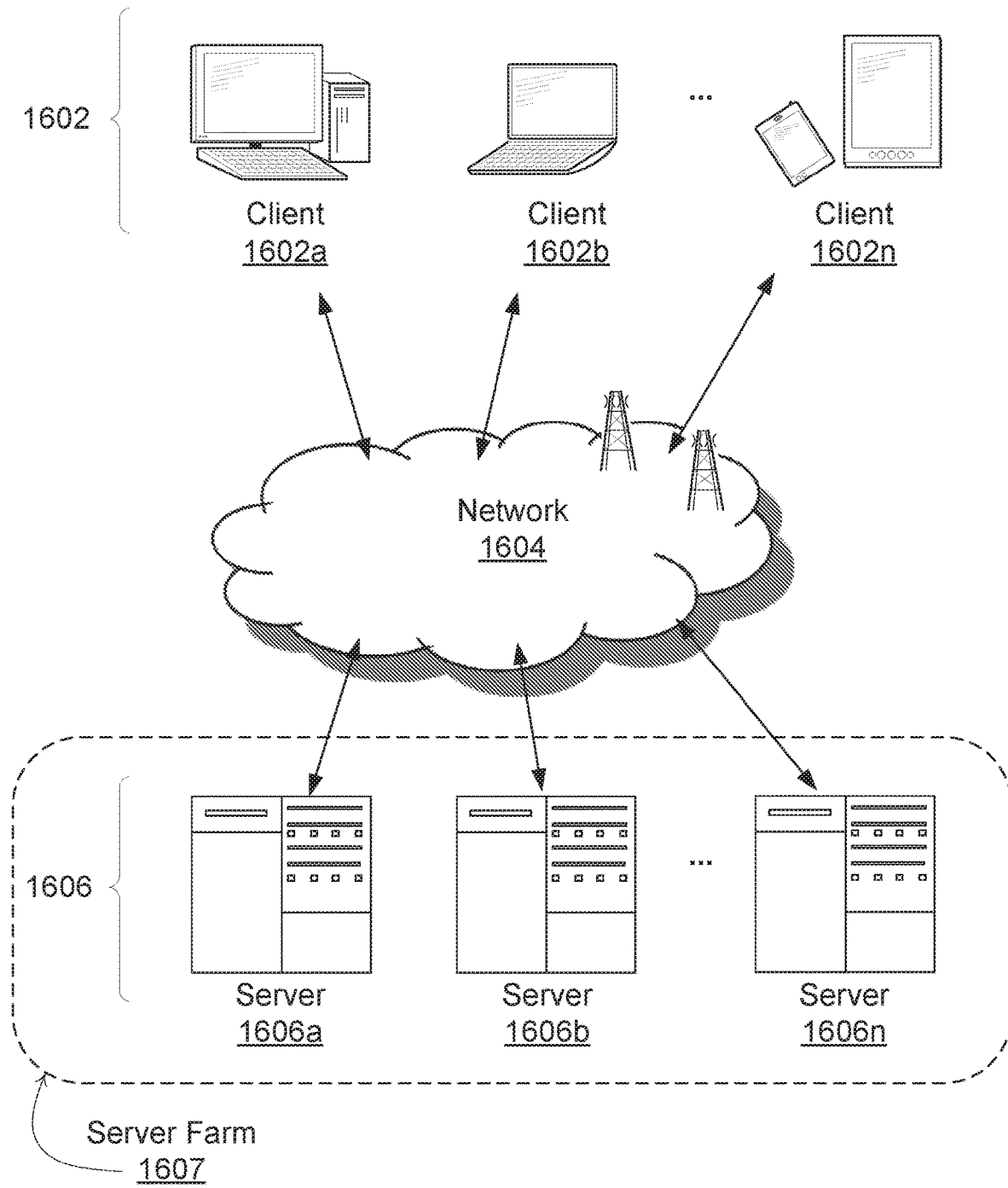
FIG. 16A is a block diagram depicting an embodiment of a network environment comprising client devices in communication with server devices.

It may be helpful to describe aspects of the operating environment as well as associated system components (e.g., hardware elements) in connection with the methods and systems described in Sections A and B. Referring to FIG. 16A, an embodiment of a network environment is depicted. In brief overview, the illustrated exploring network environment includes one or more clients $1602a$-$1602n$ (also generally referred to as local machine(s) 1602, client(s) 1602, client node(s) 1602, client machine(s) 1602, client computer(s) 1602, client device(s) 1602, endpoint(s) 1602, or endpoint node(s) 1602) in communication with one or more servers $1606a$-$1506n$ (also generally referred to as server(s) 1606, node 1606, or remote machine(s) 1606) via one or more networks 1604. In some embodiments, a client 1602 has the capacity to function as both a client node seeking access to resources provided by a server and as a server providing access to hosted resources for other clients $1602a$-$1602n$.

Although FIG. 16A shows a network 1604 between the clients 1602 and the servers 1606, the clients 1602 and the servers 1606 may be on the same network 1604. In some embodiments, there are multiple networks 1604 between the clients 1602 and the servers 1606. In one of these embodiments, a network 1604' (not shown) may be a private network and a network 1604 may be a public network. In another of these embodiments, a network 1604 may be a private network and a network 1604' a public network. In still another of these embodiments, networks 1604 and 1604' may both be private networks.

The network 1604 may be connected via wired or wireless links. Wired links may include Digital Subscriber Line (DSL), coaxial cable lines, or optical fiber lines. The wireless links may include BLUETOOTH, Wi-Fi, NFC, RFID Worldwide Interoperability for Microwave Access (WiMAX), an infrared channel or satellite band. The wireless links may also include any cellular network standards used to communicate among mobile devices, including standards that qualify as 1G, 2G, 3G, or 4G. The network standards may qualify as one or more generation of mobile telecommunication standards by fulfilling a specification or standards such as the specifications maintained by International Telecommunication Union. The 3G standards, for example, may correspond to the International Mobile Telecommunications-2000 (IMT-2000) specification, and the 4G standards may correspond to the International Mobile Telecommunications Advanced (IMT-Advanced) specification. Examples of cellular network standards include AMPS, GSM, GPRS, UMTS, LTE, LTE Advanced, Mobile WiMAX, and WiMAX-Advanced. Cellular network standards may use various channel access methods e.g. FDMA, TDMA, CDMA, or SDMA. In some embodiments, different types of data may be transmitted via different links and standards. In other embodiments, the same types of data may be transmitted via different links and standards.

The network 1604 may be any type and/or form of network. The geographical scope of the network 1604 may vary widely and the network 1604 can be a body area network (BAN), a personal area network (PAN), a local-area network (LAN), e.g. Intranet, a metropolitan area network (MAN), a wide area network (WAN), or the Internet. The topology of the network 1604 may be of any form and may include, e.g., any of the following: point-to-point, bus, star, ring, mesh, or tree. The network 1604 may be an overlay network, which is virtual and sits on top of one or more layers of other networks 1604'. The network 1604 may be of any such network topology as known to those ordinarily skilled in the art capable of supporting the operations described herein. The network 1604 may utilize different techniques and layers or stacks of protocols, including, e.g., the Ethernet protocol, the internet protocol suite (TCP/IP), the ATM (Asynchronous Transfer Mode) technique, the SONET (Synchronous Optical Networking) protocol, or the SDH (Synchronous Digital Hierarchy) protocol. The TCP/IP internet protocol suite may include application layer, transport layer, internet layer (including, e.g., IPv6), or the link layer. The network 1604 may be a type of a broadcast network, a telecommunications network, a data communication network, or a computer network.

In some embodiments, the system may include multiple, logically-grouped servers 1606. In one of these embodiments, the logical group of servers may be referred to as a server farm 1607 or a machine farm 1607. In another of these embodiments, the servers 1606 may be geographically dispersed. In other embodiments, a machine farm 1607 may be administered as a single entity. In still other embodiments, the machine farm 1607 includes a plurality of machine farms 38. The servers 1606 within each machine farm 1607 can be heterogeneous—one or more of the servers 1606 or machines 1606 can operate according to one type of operating system platform (e.g., WINDOWS NT, manufactured by Microsoft Corp. of Redmond, Washington), while one or more of the other servers 1606 can operate on according to another type of operating system platform (e.g., Unix, Linux, or Mac OS X).

In one embodiment, servers 1606 in the machine farm 1607 may be stored in high-density rack systems, along with associated storage systems, and located in an enterprise data center. In this embodiment, consolidating the servers 1606 in this way may improve system manageability, data security, the physical security of the system, and system performance by locating servers 1606 and high performance storage systems on localized high performance networks. Centralizing the servers 1606 and storage systems and coupling them with advanced system management tools allows more efficient use of server resources.

The servers 1606 of each machine farm 1607 do not need to be physically proximate to another server 1606 in the same machine farm 1607. Thus, the group of servers 1606 logically grouped as a machine farm 1607 may be interconnected using a wide-area network (WAN) connection or a metropolitan-area network (MAN) connection. For example, a machine farm 1607 may include servers 1606 physically located in different continents or different regions of a continent, country, state, city, campus, or room. Data transmission speeds between servers 1606 in the machine farm 1607 can be increased if the servers 1606 are connected using a local-area network (LAN) connection or some form of direct connection. Additionally, a heterogeneous machine farm 1607 may include one or more servers 1606 operating according to a type of operating system, while one or more other servers 1606 execute one or more types of hypervisors rather than operating systems. In these embodiments, hypervisors may be used to emulate virtual hardware, partition physical hardware, virtualized physical hardware, and execute virtual machines that provide access to computing environments, allowing multiple operating systems to run concurrently on a host computer. Native hypervisors may run directly on the host computer. Hypervisors may include VMware ESX/ESXi, manufactured by VMWare, Inc., of Palo Alto, California; the Xen hypervisor, an open source product whose development is overseen by Citrix Systems, Inc.; the HYPER-V hypervisors provided by Microsoft or others. Hosted hypervisors may run within an operating system on a second software level. Examples of hosted hypervisors may include VMware Workstation and VIRTU-ALBOX.

Management of the machine farm 1607 may be decentralized. For example, one or more servers 1606 may comprise components, subsystems and modules to support one or more management services for the machine farm 1607. In one of these embodiments, one or more servers 1606 provide functionality for management of dynamic data, including techniques for handling failover, data replication, and increasing the robustness of the machine farm 1607. Each server 1606 may communicate with a persistent store and, in some embodiments, with a dynamic store.

Server 1606 may be a file server, application server, web server, proxy server, appliance, network appliance, gateway, gateway server, virtualization server, deployment server, SSL VPN server, or firewall. In one embodiment, the server 1606 may be referred to as a remote machine or a node. In another embodiment, a plurality of nodes may be in the path between any two communicating servers.

Figure 16B:
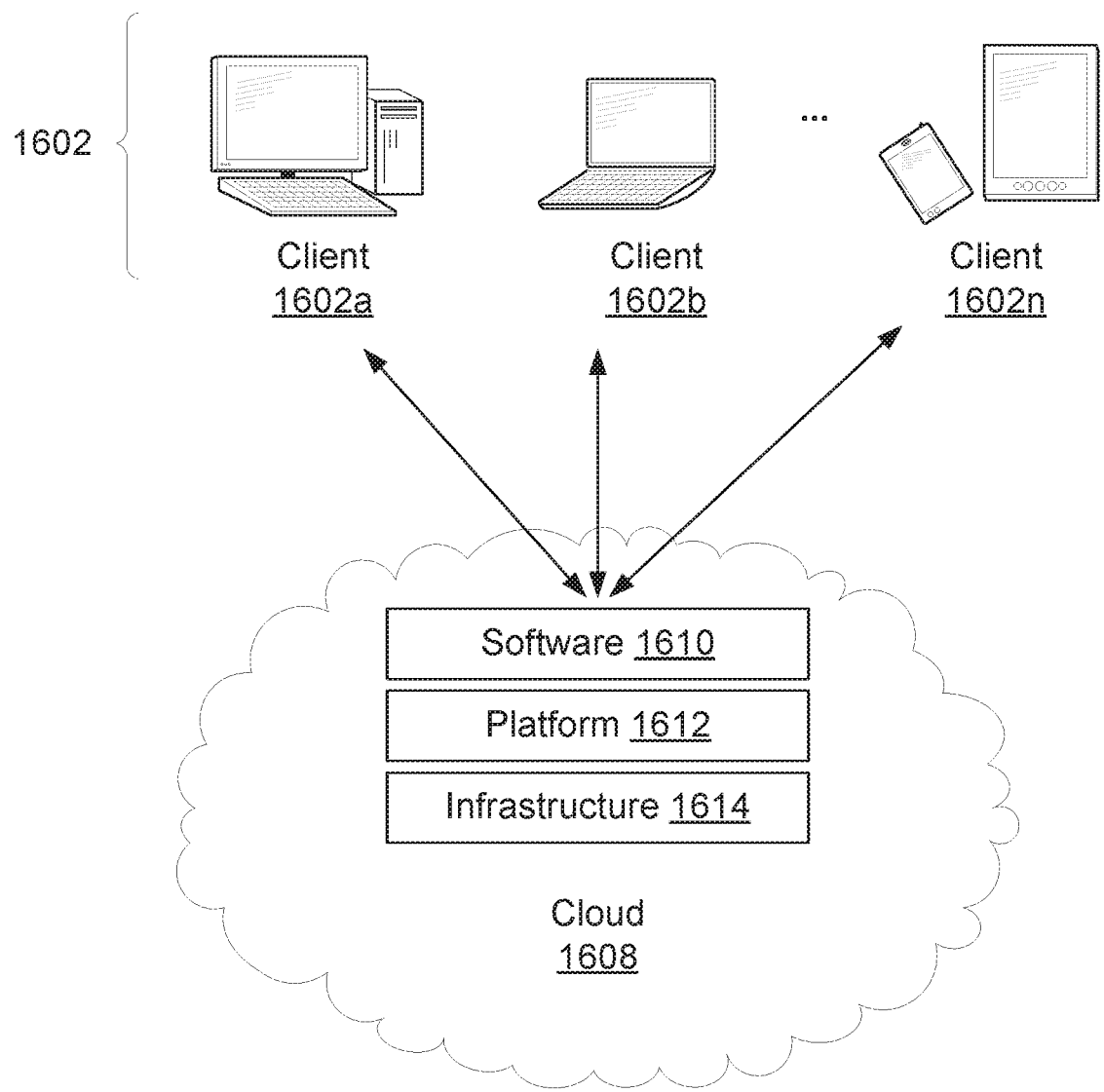
FIG. 16B is a block diagram depicting a cloud computing environment comprising client devices in communication with a cloud service provider.

Referring to FIG. 16B, a cloud computing environment is depicted. A cloud computing environment may provide client 1602 with one or more resources provided by a network environment. The cloud computing environment may include one or more clients 1602*a*-1602*n*, in communication with the cloud 1608 over one or more networks 1604. Clients 1602 may include, e.g., thick clients, thin clients, and zero clients. A thick client may provide at least some functionality even when disconnected from the cloud 1608 or servers 1606. A thin client or a zero client may depend on the connection to the cloud 1608 or server 1606 to provide functionality A zero client may depend on the cloud 1608 or other networks 1604 or servers 1606 to retrieve operating system data for the client device. The cloud 1608 may include back end platforms, e.g., servers 1606, storage, server farms or data centers.

The cloud 1608 may be public, private, or hybrid. Public clouds may include public servers 1606 that are maintained by third parties to the clients 1602 or the owners of the clients. The servers 1606 may be located off-site in remote geographical locations as disclosed above or otherwise. Public clouds may be connected to the servers 1606 over a public network. Private clouds may include private servers 1606 that are physically maintained by clients 1602 or owners of clients. Private clouds may be connected to the servers 1606 over a private network 1604. Hybrid clouds 1608 may include both the private and public networks 1604 and servers 1606.

The cloud 1608 may also include a cloud based delivery, e.g. Software as a Service (SaaS) 1610, Platform as a Service (PaaS) 1612, and Infrastructure as a Service (IaaS) 1614. IaaS may refer to a user renting the use of infrastructure resources that are needed during a specified time period. IaaS providers may offer storage, networking, servers or virtualization resources from large pools, allowing the users to quickly scale up by accessing more resources as needed. PaaS providers may offer functionality provided by IaaS, including, e.g., storage, networking, servers or virtualization, as well as additional resources such as, e.g., the operating system, middleware, or runtime resources. Examples of PaaS include WINDOWS AZURE provided by Microsoft Corporation of Redmond, Washington, Google App Engine provided by Google Inc., and HEROKU provided by Heroku, Inc. of San Francisco, California SaaS providers may offer the resources that PaaS provides, including storage, networking, servers, virtualization, operating system, middleware, or runtime resources. In some embodiments, SaaS providers may offer additional resources including, e.g., data and application resources.

Clients 1602 may access IaaS resources with one or more IaaS standards, including, e.g., Amazon Elastic Compute Cloud (EC2), Open Cloud Computing Interface (OCCI), Cloud Infrastructure Management Interface (CIMI), or OpenStack standards. Some IaaS standards may allow clients access to resources over HTTP, and may use Representational State Transfer (REST) protocol or Simple Object Access Protocol (SOAP). Clients 1602 may access PaaS resources with different PaaS interfaces. Some PaaS interfaces use HTTP packages, standard Java APIs, JavaMail API, Java Data Objects (JDO), Java Persistence API (JPA), Python APIs, web integration APIs for different programming languages including, e.g., Rack for Ruby, WSGI for Python, or PSGI for Perl, or other APIs that may be built on REST, HTTP, XML, or other protocols. Clients 1602 may access SaaS resources through the use of web-based user interfaces, provided by a web browser. Clients 1602 may also access SaaS resources through smartphone or tablet applications, including. Clients 1602 may also access SaaS resources through the client operating system.

In some embodiments, access to IaaS, PaaS, or SaaS resources may be authenticated. For example, a server or authentication server may authenticate a user via security certificates, HTTPS, or API keys. API keys may include various encryption standards such as, e.g., Advanced Encryption Standard (AES). Data resources may be sent over Transport Layer Security (TLS) or Secure Sockets Layer (SSL).

Figure 16C:
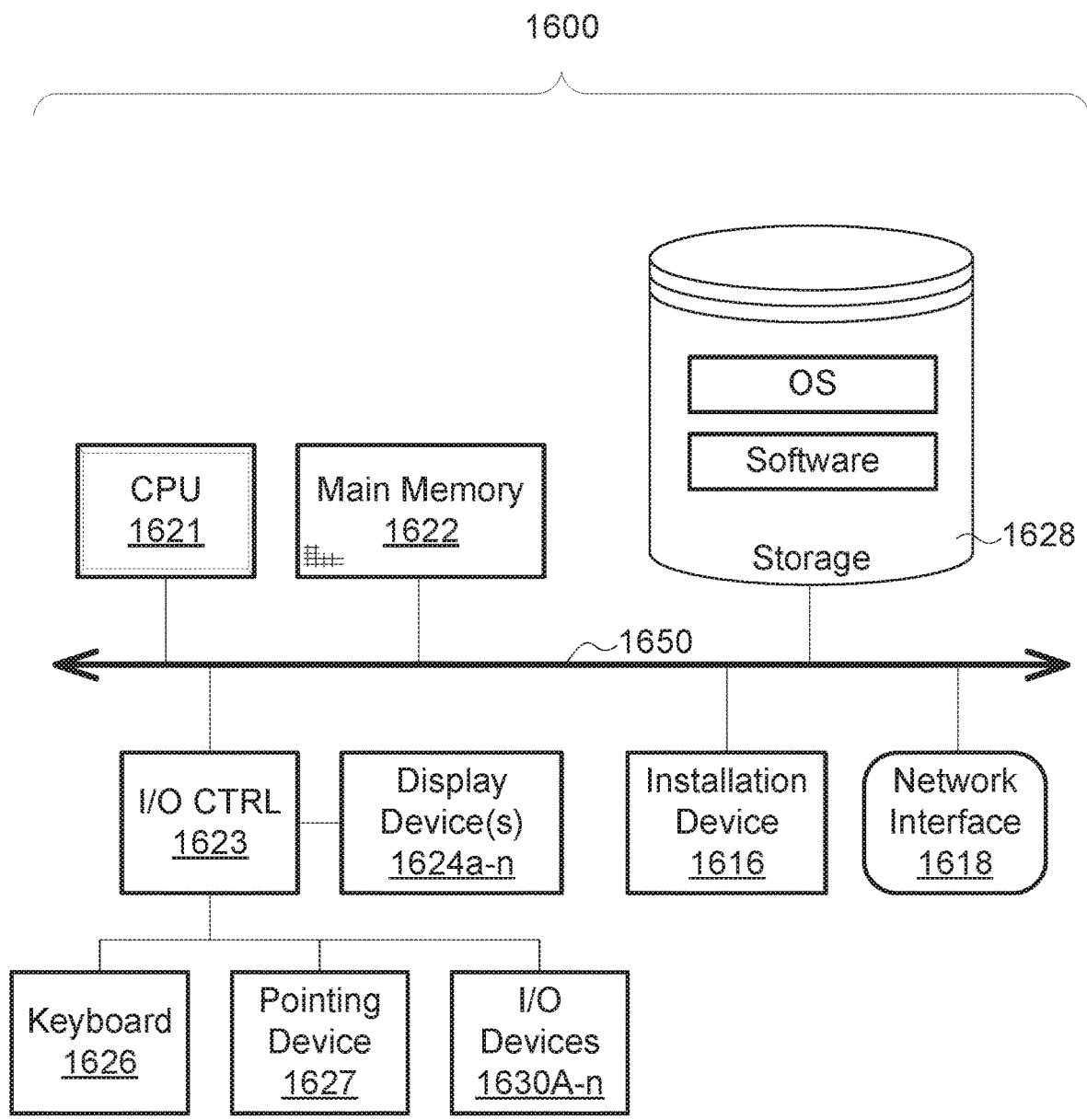
FIGS. 16C and 16D are block diagrams depicting embodiments of computing devices useful in connection with the methods and systems described herein.
Figure 16D:
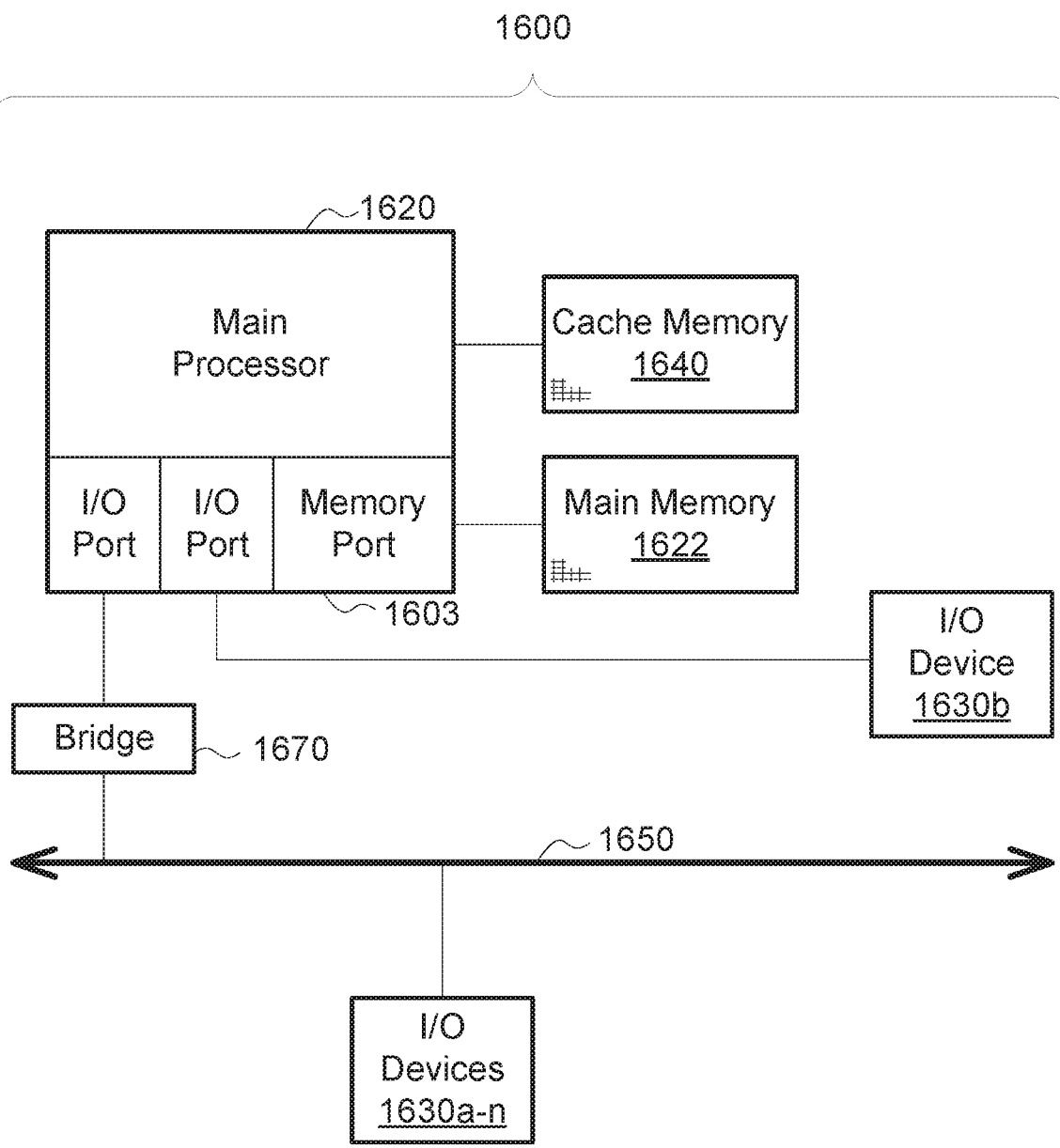

The client 1602 and server 1606 may be deployed as and/or executed on any type and form of computing device, e.g. a computer, network device or appliance capable of communicating on any type and form of network and performing the operations described herein. FIGS. 16C and 16D depict block diagrams of a computing device 1600 useful for practicing an embodiment of the client 1602 or a server 1606. As shown in FIGS. 16C and 16D, each computing device 1600 includes a central processing unit 1621, and a main memory unit 1622. As shown in FIG. 16C, a computing device 1600 may include a storage device 1628, an installation device 1616, a network interface 1618, an I/O controller 1623, display devices 1624*a*-1624*n*, a keyboard 1626 and a pointing device 1627, e.g. a mouse. The storage device 1628 may include, without limitation, an operating system, and/or software 1620. As shown in FIG. 16D, each computing device 1600 may also include additional optional elements, e.g. a memory port 1603, a bridge 1670, one or more input/output devices 1630*a*-1630*n* (generally referred to using reference numeral 1630), and a cache memory 1640 in communication with the central processing unit 1621.

The central processing unit 1621 is any logic circuitry that responds to and processes instructions fetched from the main memory unit 1622. In many embodiments, the central processing unit 1621 is provided by a microprocessor unit. The computing device 1600 may be based on any of these processors, or any other processor capable of operating as described herein. The central processing unit 1621 may utilize instruction level parallelism, thread level parallelism, different levels of cache, and multi-core processors. A multi-core processor may include two or more processing units on a single computing component.

Main memory unit 1622 may include one or more memory chips capable of storing data and allowing any storage location to be directly accessed by the microprocessor 1621. Main memory unit 1622 may be volatile and faster than storage 1628 memory. Main memory units 1622 may be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 1622 or the storage 1628 may be non-volatile; e.g., non-volatile read access memory (NVRAM), flash memory non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 1622 may be based on any of the above described memory chips, or any other available memory chips capable of operating as described herein. In the embodiment shown in FIG. 16C, the processor 1621 communicates with main memory 1622 via a system bus 1650 (described in more detail below). FIG. 16D depicts an embodiment of a computing device 1600 in which the processor communicates directly with main memory 1622 via a memory port 1603. For example, in FIG. 16D the main memory 1622 may be DRDRAM.

FIG. 16D depicts an embodiment in which the main processor 1621 communicates directly with cache memory 1640 via a secondary bus, sometimes referred to as a backside bus. In other embodiments, the main processor 1621 communicates with cache memory 1640 using the system bus 1650. Cache memory 1640 typically has a faster response time than main memory 1622 and is typically provided by SRAM, BSRAM, or EDRAM. In the embodiment shown in FIG. 16D, the processor 1621 communicates with various I/O devices 1630 via a local system bus 1650. Various buses may be used to connect the central processing unit 1621 to any of the I/O devices 1630, including a PCI bus, a PCI-X bus, or a PCI-Express bus, or a NuBus. For embodiments in which the I/O device is a video display 1624, the processor 1621 may use an Advanced Graphics Port (AGP) to communicate with the display 1624 or the I/O controller 1623 for the display 1624. FIG. 16D depicts an embodiment of a computer 1600 in which the main processor 1621 communicates directly with I/O device 1630*b* or other processors 1621' via HYPERTRANSPORT, RAPIDIO, or INFINIBAND communications technology. FIG. 16D also depicts an embodiment in which local busses and direct communication are mixed: the processor 1621 communicates with I/O device 1630*a* using a local interconnect bus while communicating with I/O device 1630*b* directly.

A wide variety of I/O devices 1630*a*-1630*n* may be present in the computing device 1600. Input devices may include keyboards, mice, trackpads, trackballs, touchpads, touch mice, multi-touch touchpads and touch mice, microphones, multi-array microphones, drawing tablets, cameras, single-lens reflex camera (SLR), digital SLR (DSLR), CMOS sensors, accelerometers, infrared optical sensors, pressure sensors, magnetometer sensors, angular rate sensors, depth sensors, proximity sensors, ambient light sensors, gyroscopic sensors, or other sensors. Output devices may include video displays, graphical displays, speakers, headphones, inkjet printers, laser printers, and 3D printers.

Devices 1630*a*-1630*n* may include a combination of multiple input or output devices, including. Some devices 1630*a*-1630*n* allow gesture recognition inputs through combining some of the inputs and outputs. Some devices 1630*a*-1630*n* provides for facial recognition which may be utilized as an input for different purposes including authentication and other commands Some devices 1630*a*-1630*n* provides for voice recognition and inputs. Additional devices 1630*a*-1630*n* have both input and output capabilities, including, e.g., haptic feedback devices, touchscreen displays, or multi-touch displays. Touchscreen, multi-touch displays, touchpads, touch mice, or other touch sensing devices may use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices may allow two or more contact points with the surface, allowing advanced functionality including, e.g., pinch, spread, rotate, scroll, or other gestures. Some touchscreen devices, including, such as on a table-top or on a wall, and may also interact with other electronic devices. Some I/O devices 1630*a*-1630*n*, display devices 1624*a*-1624*n* or group of devices may be augment reality devices. The I/O devices may be controlled by an I/O controller 1623 as shown in FIG. 16C. The I/O controller may control one or more I/O devices, such as, e.g., a keyboard 1626 and a pointing device 1627, e.g., a mouse or optical pen. Furthermore, an I/O device may also provide storage and/or an installation medium 1616 for the computing device 1600. In still other embodiments, the computing device 1600 may provide USB connections (not shown) to receive handheld USB storage devices. In further embodiments, an I/O device 1630 may be a bridge between the system bus 1650 and an external communication bus, e.g. a USB bus, a SCSI bus, a FireWire bus, an Ethernet bus, a Gigabit Ethernet bus, a Fibre Channel bus, or a Thunderbolt bus.

In some embodiments, display devices 1624*a*-1624*n* may be connected to I/O controller 1623. Display devices may include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays may use, e.g. stereoscopy, polarization filters, active shutters, or autostereoscopy. Display devices 1624*a*-1624*n* may also be a head-mounted display (HMD). In some embodiments, display devices 1624*a*-1624*n* or the corresponding I/O controllers 1623 may be controlled through or have hardware support for OPENGL or DIRECTX API or other graphics libraries.

In some embodiments, the computing device 1600 may include or connect to multiple display devices 1624*a*-1624*n*, which each may be of the same or different type and/or form. As such, any of the I/O devices 1630*a*-1630*n* and/or the I/O controller 1623 may include any type and/or form of suitable hardware, software, or combination of hardware and software to support, enable or provide for the connection and use of multiple display devices 1624a-1624n by the computing device 1600. For example, the computing device 1600 may include any type and/or form of video adapter, video card, driver, and/or library to interface, communicate, connect or otherwise use the display devices 1624a-1624n. In one embodiment, a video adapter may include multiple connectors to interface to multiple display devices 1624a-1624n. In other embodiments, the computing device 1600 may include multiple video adapters, with each video adapter connected to one or more of the display devices 1624a-1624n. In some embodiments, any portion of the operating system of the computing device 1600 may be configured for using multiple displays 1624a-1624n. In other embodiments, one or more of the display devices 1624a-1624n may be provided by one or more other computing devices 1600a or 1600b connected to the computing device 1600, via the network 1604. In some embodiments software may be designed and constructed to use another computer's display device as a second display device 1624a for the computing device 1600.

Referring again to FIG. 16C, the computing device 1600 may comprise a storage device 1628 (e.g. one or more hard disk drives or redundant arrays of independent disks) for storing an operating system or other related software, and for storing application software programs such as any program related to the software 1620. Examples of storage device 1628 include, e.g., hard disk drive (HDD); optical drive; solid-state drive (SSD); USB flash drive; or any other device suitable for storing data. Some storage devices may include multiple volatile and non-volatile memories, including, e.g., solid state hybrid drives that combine hard disks with solid state cache. Some storage device 1628 may be non-volatile, mutable, or read-only. Some storage device 1628 may be internal and connect to the computing device 1600 via a bus 1650. Some storage device 1628 may be external and connect to the computing device 1600 via an I/O device 1630 that provides an external bus. Some storage device 1628 may connect to the computing device 1600 via the network interface 1618 over a network 1604. Some client devices 1600 may not require a non-volatile storage device 1628 and may be thin clients or zero clients 1602. Some storage device 1628 may also be used as an installation device 1616, and may be suitable for installing software and programs.

Client device 1600 may also install software or application from an application distribution platform. An application distribution platform may facilitate installation of software on a client device 1602. An application distribution platform may include a repository of applications on a server 1606 or a cloud 1608, which the clients 1602a-1602n may access over a network 1604. An application distribution platform may include application developed and provided by various developers. A user of a client device 1602 may select, purchase and/or download an application via the application distribution platform.

Furthermore, the computing device 1600 may include a network interface 1618 to interface to the network 1604 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections). In one embodiment, the computing device 1600 communicates with other computing devices 1600' via any type and/or form of gateway or tunneling protocol e.g. Secure Socket Layer (SSL) or Transport Layer Security (TLS). The network interface 1618 may comprise a built-in network adapter, network interface card, PCMCIA network card, EXPRESSCARD network card, card bus network adapter, wireless network adapter, USB network adapter, modem or any other device suitable for interfacing the computing device 1600 to any type of network capable of communication and performing the operations described herein.

A computing device 1600 of the sort depicted in FIGS. 16B and 16C may operate under the control of an operating system, which controls scheduling of tasks and access to system resources. The computing device 1600 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 2000, WINDOWS Server 2012, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Washington; MAC OS and iOS, manufactured by Apple, Inc. of Cupertino, California; and Linux, a freely-available operating system, e.g. Linux Mint distribution ("distro") or Ubuntu, distributed by Canonical Ltd. of London, United Kingdom; or Unix or other Unix-like derivative operating systems; and Android, designed by Google, of Mountain View, California, among others. Some operating systems, including, e.g., the CHROME OS by Google, may be used on zero clients or thin clients, including, e.g., CHROMEBOOKS.

The computer system 1600 can be any workstation, telephone, desktop computer, laptop or notebook computer, netbook, tablet, server, handheld computer, mobile telephone, smartphone or other portable telecommunications device, media playing device, a gaming system, mobile computing device, or any other type and/or form of computing, telecommunications or media device that is capable of communication. The computer system 1600 has sufficient processor power and memory capacity to perform the operations described herein. In some embodiments, the computing device 1600 may have different processors, operating systems, and input devices consistent with the device.

In some embodiments, the computing device 1600 is a gaming system. In some embodiments, the computing device 1600 is a digital audio player. Some digital audio players may have other functionality, including, e.g., a gaming system or any functionality made available by an application from a digital application distribution platform. In some embodiments, the computing device 1600 is a portable media player or digital audio player supporting file formats including. In some embodiments, the computing device 1600 is a tablet. In other embodiments, the computing device 1600 is an eBook reader. In some embodiments, the communications device 1602 includes a combination of devices, e.g. a smartphone combined with a digital audio player or portable media player. For example, one of these embodiments is a smartphone. In yet another embodiment, the communications device 1602 is a laptop or desktop computer equipped with a web browser and a microphone and speaker system, e.g. a telephony headset. In these embodiments, the communications devices 1602 are web-enabled and can receive and initiate phone calls. In some embodiments, a laptop or desktop computer is also equipped with a webcam or other video capture device that enables video chat and video call. In some embodiments, the communication device 1602 is a wearable mobile computing device.

In some embodiments, the status of one or more machines 1602, 1606 in the network 1604 is monitored, generally as part of network management. In one of these embodiments, the status of a machine may include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information may be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

The description herein including modules emphasizes the structural independence of the aspects of the image reconstructor, and illustrates one grouping of operations and responsibilities of the image reconstructor. Other groupings that execute similar overall operations are understood within the scope of the present application. Modules may be implemented in hardware and/or as computer instructions on a non-transient computer readable storage medium, and modules may be distributed across various hardware or computer based components.

Example and non-limiting module implementation elements include sensors providing any value determined herein, sensors providing any value that is a precursor to a value determined herein, datalink and/or network hardware including communication chips, oscillating crystals, communication links, cables, twisted pair wiring, coaxial wiring, shielded wiring, transmitters, receivers, and/or transceivers, logic circuits, hard-wired logic circuits, reconfigurable logic circuits in a particular non-transient state configured according to the module specification, any actuator including at least an electrical, hydraulic, or pneumatic actuator, a solenoid, an op-amp, analog control elements (springs, filters, integrators, adders, dividers, gain elements), and/or digital control elements.

Non-limiting examples of various embodiments are disclosed herein. Features from one embodiments disclosed herein may be combined with features of another embodiment disclosed herein as someone of ordinary skill in the art would understand.

As utilized herein, the terms "approximately," "about," "substantially" and similar terms are intended to have a broad meaning in harmony with the common and accepted usage by those of ordinary skill in the art to which this disclosure pertains. It should be understood by those of skill in the art who review this disclosure that these terms are intended to allow a description of certain features described without restricting the scope of these features to the precise numerical ranges provided. Accordingly, these terms should be interpreted as indicating that insubstantial or inconsequential modifications or alterations of the subject matter described and are considered to be within the scope of the disclosure.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary embodiments, and that such variations are intended to be encompassed by the present disclosure. It is recognized that features of the disclosed embodiments can be incorporated into other disclosed embodiments.

It is important to note that the constructions and arrangements of apparatuses or the components thereof as shown in the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present disclosure.

While various inventive embodiments have been described and illustrated herein, those of ordinary skill in the art will readily envision a variety of other mechanisms and/or structures for performing the function and/or obtaining the results and/or one or more of the advantages described herein, and each of such variations and/or modifications is deemed to be within the scope of the inventive embodiments described herein. More generally, those skilled in the art will readily appreciate that, unless otherwise noted, any parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be embodied as a method, of which at least one example has been provided. The acts performed as part of the method may be ordered in any suitable way unless otherwise specifically noted. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification and in the claims, unless clearly indicated to the contrary, should be understood to mean "at least one." As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

What is claimed is:

1. A method of reconstructing biomedical images, comprising:
    identifying, by a computing system, a first projection dataset acquired from a first tomographic biomedical imaging scan in a first image modality;
    applying, by the computing system, to the first projection dataset, an encoder-decoder model for reconstructing tomographic biomedical images from projection data, the encoder-decoder model comprising:
        an encoder comprising a first series of transform layers having an input size, to generate a feature map of a first size using the first projection dataset; and
        a decoder comprising a second series of transform layers and at least one up-sampler, the decoder having an output size different from the input size of the first series of transform layers of the encoder, the decoder to generate a first tomographic biomedical image of a second size using the feature map of the first size from the encoder, the second size larger than the first size via application the at least one up-sampler, the first tomographic biomedical image being in the first image modality;
    wherein the encoder-decoder model is trained using (i) a second projection dataset acquired using a second tomographic biomedical imaging scan in a second image modality and (ii) a second tomographic biomedical image in the second image modality derived from the second projection dataset, the second image modality different from the first image modality of the first tomographic biomedical image, and
    providing, by the computing system, the generated first tomographic biomedical image.

2. The method of claim 1, wherein identifying the first projection dataset further comprises identifying the first projection dataset by acquiring a two-dimensional slice of a third projection dataset generated from the first tomographic biomedical imaging scan, the first projection dataset corresponding to the two-dimensional slice of the third projection dataset.

3. The method of claim 1, wherein identifying the first projection dataset further comprises applying an interpolation onto a third projection dataset having a plurality of data counts generated from the first tomographic biomedical imaging scan to generate the first projection dataset corresponding to a subset of the plurality of data counts.

4. The method of claim 1, wherein identifying the first projection dataset further comprises:
    identifying a third projection dataset generated from the first tomographic biomedical imaging scan, the third projection dataset including a plurality of data counts defined in three-dimensions; and
    identifying, in accordance with an interpolation function, a data plane from the third projection dataset corresponding to one dimension of the plurality of data counts as the first projection dataset.

5. The method of claim 1, wherein:
    the encoder comprises the first series of transform layers having the input size corresponding to a plurality of data counts of the first projection dataset, to generate the feature map in a latent space representation having the first size; and
    the decoder comprises the second series of transform layers having the input size corresponding to the first size of the latent space representation and the output size corresponding to a plurality of pixels of the first tomographic biomedical image.

6. The method of claim 1, wherein applying the encoder-decoder model further comprises applying the encoder-decoder model, to the first projection dataset to generate the first tomographic biomedical image, without a plurality of iterations.

7. The method of claim 1, wherein the second projection dataset is simulated using effects comprising at least one of: (i) noise, (ii) scattered and random coincidences, (iii) photon attenuation, or (iv) blurring.

8. The method of claim 1, wherein the encoder comprises the first series of transform layers having a non-linear characteristic to generate the feature map comprising a plurality of features, each feature of the plurality of features corresponding to a trace in a domain of the first projection dataset.

9. A method of training models to reconstruct biomedical images, comprising:

identifying, by a computing system, training data including (i) a projection dataset acquired via a first tomographic biomedical imaging scan in a first image modality and (ii) a first tomographic biomedical image in the first image modality derived from the projection dataset;

applying, by the computing system, to the projection dataset, an encoder-decoder model for reconstructing tomographic biomedical images in a second image modality from projection data acquired via second tomographic biomedical imaging scan in the second image modality, the encoder-decoder model having:

an encoder comprising a first series of transform layers having an input size, to generate a feature map of a first size using the projection dataset; and a decoder comprising a second series of transform layers and at least one up-sampler, the decoder having an output size different from the input size of the first series of transform layers of the encoder, the decoder to generate a second tomographic biomedical image of a second size using the feature map of the first size from the encoder, the second size larger than the first size via application the at least one up-sampler, the second tomographic biomedical image being in the first image modality different from the second image modality; and identifying, by the computing system, the second tomographic biomedical image in the first image modality;

determining, by the computing system, an error measure between the first tomographic biomedical image in the first image modality from the training data and the second tomographic biomedical image generated in the first image modality from the encoder-decoder model; and modifying, by the computing system, at least one parameter of the first series of transform layers or the second series of transform layers in the encoder-decoder model for reconstructing tomographic biomedical images in the second image modality based on the error measure between the first tomographic biomedical image and the second tomographic biomedical image in the first image modality.

10. The method of claim 9, wherein identifying the training data further comprises identifying the training data by acquiring a two-dimensional slice of a second projection dataset derived from the first tomographic biomedical image, the projection dataset corresponding to the two-dimensional slice.

11. The method of claim 9, wherein identifying the projection dataset further comprises applying an interpolation onto the projection dataset having a plurality of data counts generated from the first tomographic biomedical imaging scan to generate the projection dataset corresponding to a subset of the plurality of data counts.

12. The method of claim 9, wherein:

the encoder comprises the first series of transform layers having the input size corresponding to a plurality of data counts of the projection dataset, to generate the feature map in a latent space representation having the first size; and the decoder comprises the second series of transform layers having the input size corresponding to the first size of the latent space representation and the output size corresponding to a plurality of pixels of the second tomographic biomedical image.

13. The method of claim 9, wherein the projection dataset is simulated using effects comprising at least one of: (i) noise, (ii) scattered and random coincidences, (iii) photon attenuation, or (iv) blurring.

14. The method of claim 9, wherein the encoder comprises the first series of transform layers having a non-linear characteristic to generate the feature map comprising a plurality of features, each feature of the plurality of features corresponding to a trace in a domain of the projection dataset.

15. A system for reconstructing biomedical images, comprising:

a computing system having one or more processors coupled with memory, configured to:

identify a first projection dataset acquired from a first tomographic biomedical imaging scan in a first image modality;

apply, to the first projection dataset, an encoder-decoder model for reconstructing tomographic biomedical images from projection data, the encoder-decoder model comprising:

an encoder comprising a first series of transform layers having an input size, to generate a feature map of a first size using the first projection dataset; and a decoder comprising a second series of transform layers and at least one up-sampler, the decoder having an output size different from the input size of the first series of transform layers of the encoder, the decoder to generate a first tomographic biomedical image of a second size using the feature map of the first size from the encoder, the second size larger than the first size via application the at least one up-sampler, the first tomographic biomedical image being in the first image modality, wherein the encoder-decoder model is trained using (i) a second projection dataset acquired using a second tomographic biomedical imaging scan in a second image modality and (ii) a second tomographic biomedical image in the second image modality derived from the second projection dataset, the second image modality different from the first image modality of the first tomographic biomedical image; and provide the generated first tomographic biomedical image.

16. The system of claim 15, wherein the computing system is further configured to identify the first projection dataset by acquiring two-dimensional slice of a third projection dataset generated from the first tomographic biomedical imaging scan, the first projection dataset corresponding to the two-dimensional slice of the third projection dataset.

17. The system of claim 15, wherein the computing system is further configured to apply an interpolation onto a third projection dataset having a plurality of data counts generated from the first tomographic biomedical imaging scan to generate the first projection dataset corresponding to a subset of the plurality of data counts.

18. The system of claim 15, wherein:
the encoder comprises the first series of transform layers having the input size corresponding to a plurality of data counts of the first projection dataset, to generate the feature map in a latent space representation having the first size; and
the decoder comprises the second series of transform layers having the input size corresponding to the first size of the latent space representation and the output size corresponding to a plurality of pixels of the first tomographic biomedical image.

19. The system of claim 15, wherein the computing system is further configured to apply the encoder-decoder model to the first projection dataset, to generate the first tomographic biomedical image without a plurality of iterations.

20. The system of claim 15, wherein the projection dataset is simulated using effects comprising at least one of: (i) noise, (ii) scattered and random coincidences, (iii) photon attenuation, or (iv) blurring.

\* \* \* \* \*